(12) United States Patent
King et al.

(10) Patent No.: US 9,498,622 B2
(45) Date of Patent: Nov. 22, 2016

(54) PROGRAMMING TECHNIQUES FOR PERIPHERAL NERVE FIELD STIMULATION

(75) Inventors: Gary W. King, Fridley, MN (US); Steven M. Goetz, North Oaks, MN (US); Andrew H. Houchins, Lino Lakes, MN (US); Jeffrey T. Keacher, Stanford, CA (US); Jordan J. Greenberg, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 2103 days.

(21) Appl. No.: 12/359,656

(22) Filed: Jan. 26, 2009

(65) Prior Publication Data

US 2009/0281595 A1  Nov. 12, 2009

Related U.S. Application Data

(60) Provisional application No. 61/051,942, filed on May 9, 2008.

(51) Int. Cl.
| | | |
|---|---|---|
| *A61N 1/00* | (2006.01) |
| *A61N 1/05* | (2006.01) |
| *A61N 1/372* | (2006.01) |
| *A61N 1/36* | (2006.01) |

(52) U.S. Cl.
CPC ......... *A61N 1/0553* (2013.01); *A61N 1/36071* (2013.01); *A61N 1/36185* (2013.01); *A61N 1/37247* (2013.01); *A61N 1/36021* (2013.01)

(58) Field of Classification Search
CPC .......................... A61N 1/0553; A61N 1/36071
USPC ......................................................... 607/46
See application file for complete search history.

(56) References Cited

U.S. PATENT DOCUMENTS

| 6,609,032 B1 * | 8/2003 | Woods et al. .................... 607/46 |
| 6,909,917 B2 | 6/2005 | Woods et al. |
| 7,035,690 B2 | 4/2006 | Goetz |
| 7,519,431 B2 | 4/2009 | Goetz et al. |
| 7,848,818 B2 | 12/2010 | Barolat et al. |
| 8,588,914 B2 | 11/2013 | Rooney et al. |
| 8,620,435 B2 | 12/2013 | Rooney et al. |
| 8,855,777 B2 | 10/2014 | King et al. |
| 2004/0098063 A1 * | 5/2004 | Goetz ............................ 607/48 |
| 2005/0143789 A1 | 6/2005 | Whitehurst et al. |
| 2006/0155333 A1 | 7/2006 | Goetz |
| 2006/0241720 A1 | 10/2006 | Woods |
| 2006/0259099 A1 | 11/2006 | Goetz et al. |

(Continued)

OTHER PUBLICATIONS

Notification Concerning Transmittal of International Preliminary Report on Patentability, dated Nov. 18, 2010 for corresponding PCT/US2009/031983, 8 pgs.

(Continued)

*Primary Examiner* — Edward Moran
*Assistant Examiner* — Nadia A Mahmood
(74) *Attorney, Agent, or Firm* — Shumaker & Sieffert, P.A.

(57) ABSTRACT

Peripheral nerve field stimulation (PNFS) delivered by medical device to a patient may be programmed by specifying one or more characteristics of a stimulation field generated by the IMD to provide the PNFS. The characteristics of the stimulation field may include, for example, a direction of stimulation within the field, a breadth of the stimulation field, a focus of stimulation within the stimulation field, a depth of the stimulation field relative to a reference point, such as the epidermis of the patient, or a nerve fiber diameter selection.

27 Claims, 20 Drawing Sheets

(56) References Cited

U.S. PATENT DOCUMENTS

2007/0073353 A1* 3/2007 Rooney et al. ............ 607/36
2007/0073356 A1   3/2007 Rooney et al.
2007/0203545 A1   8/2007 Stone et al.
2007/0225768 A1   9/2007 Dobak
2009/0281595 A1  11/2009 King et al.

OTHER PUBLICATIONS

U.S. Appl. No. 61/051,942, filed May 9, 2008, entitled "Programming Techniques for Peripheral Nerve Field Stimulation", by King et al.
U.S. Appl. No. 61/051,947, filed May 9, 2008, entitled "Programming Techniques for Peripheral Nerve Field Stimulation", by King et al.
U.S. Appl. No. 12/359,712, filed Jan. 26, 2009, entitled "Programming Techniques for Peripheral Nerve Field Stimulation", by King et al.
Notification of Transmittal of the International Search Report and the Written Opinion of the International Searching Authority, or the Declaration dated Mar. 27, 2009 for corresponding PCT Application No. PCT/US2009/031983 (12 pgs.).

* cited by examiner

PROGRAMMING TECHNIQUES FOR PERIPHERAL NERVE FIELD STIMULATION

This application claims the benefit of U.S. Provisional Application No. 61/051,942 to King et al., entitled, "PROGRAMMING TECHNIQUES FOR PERIPHERAL NERVE FIELD STIMULATION" and filed on May 9, 2008. The entire content of U.S. Provisional Application No. 61/051,942 is incorporated herein by reference.

TECHNICAL FIELD

The disclosure relates to medical devices, and more particularly, to control of therapy delivery by medical devices.

BACKGROUND

A variety of therapies, such as neurostimulation and pharmaceutical therapies, e.g., drugs, may be delivered to a patient to treat chronic or episodic pain. Examples of neurostimulation therapies used to treat pain are transcutaneous electrical nerve stimulation (TENS), percutaneous electrical nerve stimulation (PENS), peripheral nerve stimulation (PNS), spinal cord stimulation (SCS), deep brain stimulation (DBS), cortical stimulation (CS), and peripheral nerve field stimulation (PNFS). Examples of drugs used to treat pain are opioids, cannabinoids, local anesthetics, baclofen, adenosine and alpha-blockers.

PNS, SCS, DBS, CS, and PNFS are typically delivered by an implantable medical device (IMD). An IMD delivers neurostimulation therapy via electrodes, which are typically coupled to the IMD by one or more leads. The number and positions of the leads and electrodes is largely dependent on the type or cause of the pain, and the type of neurostimulation delivered to treat the pain.

SUMMARY

In general, the disclosure is directed to programming peripheral nerve field stimulation (PNFS) that is delivered by a medical device to a region of a body of a patient in which the patient experiences pain via electrodes implanted in the region. In PNFS, a medical device may deliver stimulation pulses or continuous stimulation waveforms to one or more tissue areas via electrodes to, for example, reduce the sensation of pain in a tissue area proximate to an implantation site of the electrodes without targeting a specific nerve.

A user, such as a clinician or patient, may program PNFS delivered by a medical device, such as an implantable medical device (IMD), by selecting one or more characteristics of a stimulation field generated by the medical device to provide the PNFS. The stimulation field may extend in a two dimensional region of the body of the patient (e.g., a plane defined by two orthogonal axes) or a three dimensional region of the body of the patient (e.g., defined by three orthogonal axes). The characteristics of the stimulation field may include, for example, a direction of stimulation within the field, a breadth of the stimulation field, a focus of stimulation within the stimulation field, and a depth of the stimulation field relative to a reference point, such as the epidermis of the patient. The characteristics, such as, for example, the direction of stimulation field or breadth of the stimulation field, may be defined or measured in any direction within the two or three dimensional region. In another example, PNFS may be programmed based on user input indicating a desired therapeutic effect for a specific therapy region in which the patient feels pain. Similarly, a computing device may provide a user interface that allows a user to select at least one region from among a plurality of regions in which the patient experiences pain and adjust the PNFS of the selected region(s).

In some examples, a configuration of electrodes electrically coupled to an IMD may be determined based on a stimulation field vector input, which may be specified by a user, e.g., by providing input via a user interface of a computing device. The vector input may indicate a desired direction of current flow, a direction of electric field lines for the electrical field resulting from the PNFS, or a direction of a voltage gradient. The configuration of electrodes may include, for example, a first electrode and a second electrode selected from an electrode array. In some examples, a first active electrode, which may be an anode electrode, may be selected from the electrode array based on a vector beginning point of the stimulation vector input and a second active electrode, which may be a cathode electrode, may be selected based on a vector end point. In this way, an electric current flowing from the at least one anode to the at least one cathode may produce a stimulation direction corresponding to the stimulation field vector input.

In addition to programming PNFS based on a user-specified stimulation field vector, a user may also specify other characteristics of the stimulation field. For example, the user may specify a breadth of the stimulation field by providing a stimulation breadth input. The breadth of the stimulation field may be, for example, a width of the stimulation field in a linear dimension, which may be taken at any point along the stimulation field (which typically defines a field in three dimensions, thereby defining a volume). As another example, the user may specify a size of a stimulation focus of the stimulation field by providing a stimulation focus input. The stimulation focus may affect the shape of the stimulation field, for example more circular or more oblong. As yet another example, the user may specify a depth of stimulation relative to a reference point by providing a stimulation depth input.

In other examples described herein, with the aid of a computing device, a user, such as the patient or clinician, may select at least one region from among a plurality of regions in which the patient experiences pain and adjust the PNFS therapy delivered to the selected region(s). The user may also provide a therapy input, which defines an aspect of PNFS for the at least one region. The therapy input may include, for example, activating or deactivating PNFS in the at least one region, indicating a size or focus of PNFS in the at least one region, adjusting the relative intensity of PNFS between at least a first region and a second region, balancing PNFS between at least two regions, shifting PNFS from a first region to a second region, and adjusting the extent to which a first stimulation field produced by delivering PNFS to a first region overlaps a second stimulation field produced by delivering PNFS to a second region. Therapy parameter values of a therapy program for the PNFS may be selected based on a therapy input, e.g., specifying the region of pain as well as the aspect of the PNFS for the selected region.

In another example of a programming technique, a user may directly reference a pain region and provide input specifying a desired therapeutic effect of the PNFS for the pain region. The therapeutic effects may be achieved by modifying a stimulation frequency of PNFS delivered to the region in which a patient experiences pain. Different stimulation frequencies may elicit different patient responses. For example, a relatively low frequency stimulation may activate muscle tissue and/or reduce pain by stimulating the production of endogenous endorphins, and a relatively high frequency stimulation may produce paresthesia. In some examples, the user may indicate more than one desired therapeutic effect for the same pain region. A processor may determine a therapy program based on the desired therapeutic effect input.

In one aspect, the disclosure is directed to a method comprising receiving a stimulation field vector input from a user via a user interface, wherein the stimulation field vector input indicates a direction of electrical stimulation within a stimulation field that provides electrical stimulation in a region of a body of a patient, and determining an electrode configuration for generating the stimulation field based on the stimulation field vector input, wherein the electrode configuration comprises a selection of at least two active electrodes from an electrode array and a polarity of each of the selected electrodes. In some examples, the electrical stimulation comprises peripheral nerve field stimulation in the region of the body of the patient in which the patient experiences pain.

In another aspect, the disclosure is directed to a system comprising a user interface, and a processor that receives a stimulation field vector input from a user via the user interface, where the stimulation field vector input indicates a direction of electrical stimulation in a stimulation field that provides electrical stimulation in a region of a body of a patient, and determines an electrode configuration for generating the stimulation field based on the stimulation field vector input, wherein the electrode configuration comprises a selection of at least two active electrodes from an electrode array and a polarity of each of the selected electrodes. In some examples, the electrical stimulation comprises peripheral nerve field stimulation in the region of the body of the patient in which the patient experiences pain.

In another aspect, the disclosure is directed to a system comprising means for receiving a stimulation field vector input from a user via a user interface, wherein the stimulation field vector input indicates a direction of electrical stimulation within a stimulation field that provides electrical stimulation in a region of a body of a patient, and means for determining an electrode configuration for generating the stimulation field based on the stimulation field vector input, wherein the electrode configuration comprises a selection of at least two active electrodes from an electrode array and a polarity of each of the selected electrodes. In some examples, the electrical stimulation comprises peripheral nerve field stimulation in the region of the body of the patient in which the patient experiences pain.

In another aspect, the disclosure is directed to a computer-readable medium comprising instructions. The instructions cause a programmable processor to receive a stimulation field vector input from a user, wherein the stimulation field vector input indicates a direction of electrical stimulation within a stimulation field that provides electrical stimulation in a region of a body of a patient, and determine an electrode configuration for generating the stimulation field in the region based on the stimulation field vector input, wherein the electrode configuration comprises a selection of at least two active electrodes from an electrode array and a polarity of each of the selected electrodes. In some examples, the electrical stimulation comprises peripheral nerve field stimulation in the region of the body of the patient in which the patient experiences pain.

In another aspect, the disclosure is directed to a computer-readable medium containing instructions. The instructions cause a programmable processor to perform any of the techniques described herein.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
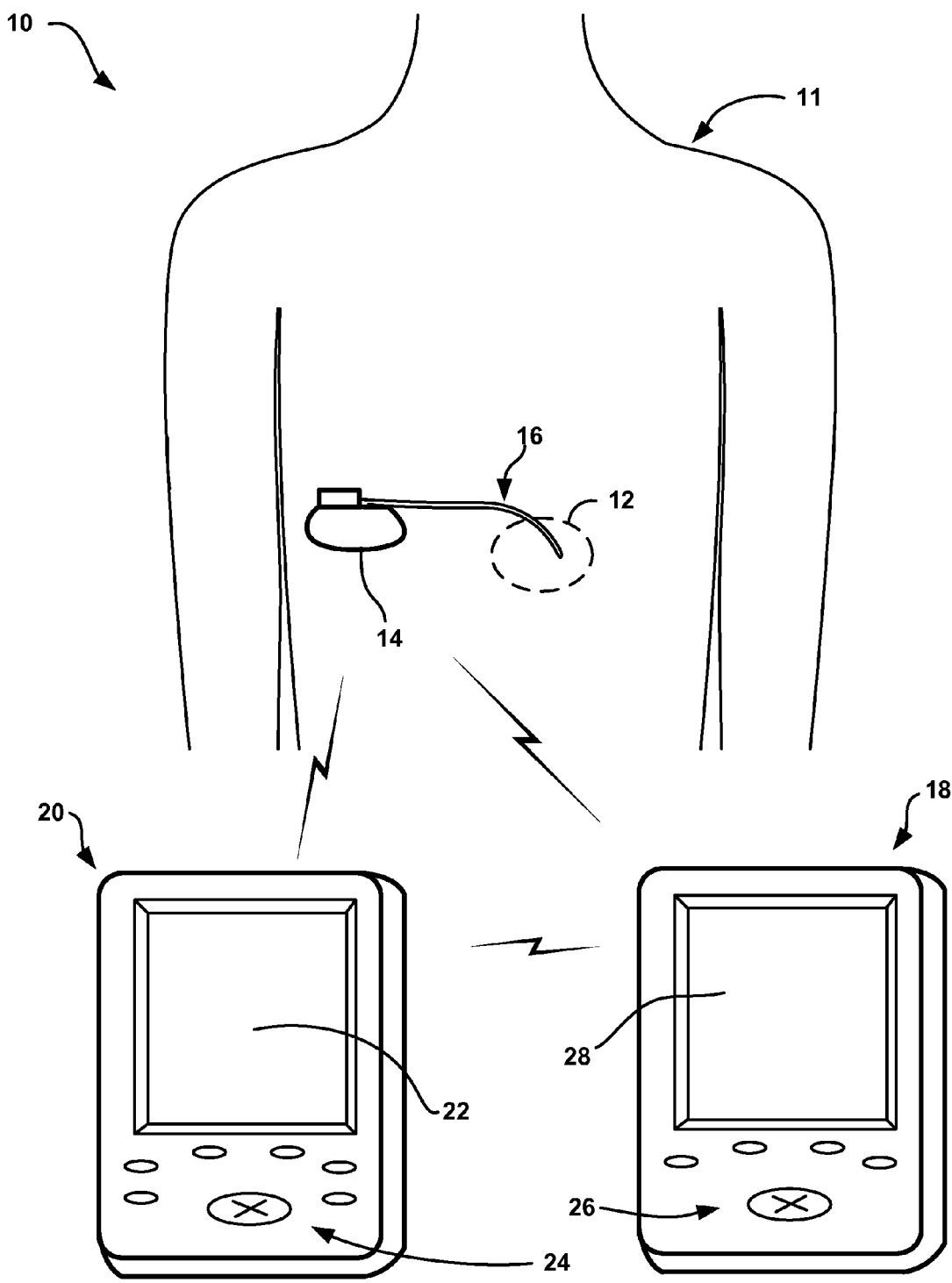
FIG. 1 is a conceptual diagram illustrating an example system for programming a medical device to deliver peripheral nerve field stimulation (PNFS).

In general, the disclosure is directed to programming a medical device to deliver electrical stimulation therapy to a region of a body of a patient in which the patient experiences pain. In some examples, the electrical stimulation therapy includes peripheral nerve field stimulation (PNFS). PNFS is delivered by a medical device via electrodes implanted in the region where the patient experiences pain. Some examples of programming techniques described herein allow a user, such as a clinician or patient, to determine a therapy program for the PNFS based on user input that specifies one or more characteristics of the stimulation field that is delivered to the region in which the patient experiences pain. The characteristics of the stimulation field may include, for example, a direction of stimulation within the field, a breadth of the stimulation field, a focus of stimulation within the stimulation field, a fiber diameter selectivity, and a depth of the stimulation field relative to a reference point, such as the epidermis of the patient.

Accordingly, in one aspect, the present disclosure is directed to determining an electrode configuration based on a stimulation field vector input provided by a user. The stimulation field vector input may indicate a stimulation direction for PNFS in the region of a body of a patient in which the patient experiences pain. The electrode configuration may include a selection of one or more electrodes from an electrode array and a polarity of the selected electrodes. In some examples, the size (e.g., magnitude) of the stimulation vector may also be used to indicate the desired stimulation amplitude or breadth. For example, a particular dimension (e.g., one millimeter) of the stimulation vector magnitude may correspond to a specific increment of stimulation amplitude (current or voltage) or breadth. In some examples, the greater the magnitude or other size of the stimulation vector input by the user, the greater the amplitude or stimulation breadth of the resulting therapy delivered by a medical device.

In some examples, a computing device, such as a clinician programmer or patient programmer, includes a user interface that receives the stimulation field vector input from the user and a processor that determines an electrode configuration, and, in some cases, stimulation amplitude or breadth, based on the stimulation field vector input. In other examples, the computing device includes the user interface, and a medical device includes the processor that determines the electrode configuration and other stimulation parameter values based on the stimulation field vector input. While programmers are primarily referred to herein, in other embodiments, other types of computing devices may be used, such as a general purpose computer running a medical device programming application, a clinician workstation, and the like.

In some examples, determining an electrode configuration comprises selecting an electrode configuration from a plurality of predetermined electrode configurations stored in a memory of a device, such as the programmer or the IMD, based on the stimulation field vector input. In other examples, determining an electrode configuration comprises generating an electrode configuration based on the stimulation field vector input.

In other examples of programming PNFS therapy described herein, a user may program PNFS with the aid of a programmer by selecting at least one region from among a plurality of regions in which the patient experiences pain and control the PNFS therapy delivered to the selected region(s). The selection input may be input by the user via a user interface of a programmer, such as a patient programmer or a clinician programmer.

The user may also provide a therapy input that defines an aspect of PNFS for the at least one region selected by the user. The therapy input may include, for example, activating or deactivating PNFS in the at least one region, indicating a size or focus of PNFS in the at least one region, adjusting the relative intensity of PNFS between at a first region and a second region, balancing the PNFS between at least two regions, shifting PNFS from a first region to a second region, and adjusting the extent to which a first stimulation field produced by delivering PNFS to a first region overlaps a second stimulation field produced by delivering PNFS to a second region. A therapy program for providing the PNFS to the at least one user-selected region may be determined based on the user-provided therapy input. In some examples, the therapy program may be selected from a plurality of therapy programs stored in a memory of a device, such as the programmer or the medical device, based on the therapy input. In other examples, a therapy program may be generated based on the therapy input.

In other examples of programming PNFS therapy described herein, a user may directly reference a region of a body in which a patient experiences pain and provide input specifying the desired therapeutic effect for PNFS therapy in this region. The desired therapeutic effect may be, for example, a physiological effect perceived by the patient. The desired therapeutic effect may be achieved by, for example, modifying a stimulation frequency of PNFS delivered to the region in which a patient experiences pain. Different stimulation frequencies may elicit different responses. For example, relatively low frequency stimulation (e.g., less than about 10 Hertz (Hz)), may activate muscle tissue, low frequency stimulation (e.g., about 10 Hz to about 30 Hz) may stimulate production of endogenous endorphins, and relatively high frequency stimulation (e.g., greater than about 30 Hz) may produce paresthesia. In some examples, more than one desired therapeutic effect may be indicated for a common region within the patient. If the user inputs more than one desired effect, the processor of the programmer (or another computing device) may control the medical device to deliver interleaving stimulation signals (e.g., pulses) having different frequencies or other stimulation parameters.

In some examples, the stimulation frequency ranges suitable for eliciting the desired responses may be determined by a clinician on a patient-specific basis via in-clinic testing or another calibration procedure. For example, test PNFS may be delivered to the patient in a plurality of different frequency ranges to determine the patient's response to the PNFS. A frequency of stimulation may be changed until a desired therapeutic effect is perceived by the patient. The clinician may also determine the range of stimulation frequencies that produce the desired therapeutic effects for the patient. The process may be repeated for any suitable number of desired therapeutic effects. In other examples, the stimulation frequency ranges suitable for eliciting the desired responses may be determined based on information that is not specific to the patient. For example, trial stimulation may be delivered to a group of patients and the frequency ranges may be determined based on the responses of the patients within the group.

A therapy program defining the PNFS may be determined based on the therapeutic effect input. In some examples, a therapy program may be selected from a plurality of predetermined therapy programs stored in a memory of a device, such as the programmer or the IMD, based on the therapeutic effect input. In other examples, a therapy program may be generated based on the therapeutic effect input.

FIG. 1 is a conceptual diagram illustrating an example system 10 for programming an implantable medical device (IMD) 14 for treating pain of a patient 11 by delivering peripheral nerve field stimulation (PNFS) to a region in which patient 11 feels pain. While patient 11 is generally referred to as a human patient, other mammalian or non-mammalian patients are also contemplated.

System 10 includes IMD 14, which delivers the PNFS therapy to patient 11. IMD 14 may include circuitry for the generation of electrical pulses, and may deliver PNFS in the form of electrical pulses. In other examples, IMD 14 includes circuitry for the generation of continuous electrical waveforms, and may deliver PNFS in the form of continuous electrical waveforms. While electrical pulses are primarily referred to herein, the disclosure also applies to PNFS that includes the delivery of continuous waveform stimulation signals. In the illustrated example, IMD 14 delivers PNFS via an electrode array (not shown in FIG. 1) carried by a lead 16, and, in some cases, one or more electrodes coupled to an outer housing of IMD 14.

As used herein, an electrode array includes a set of at least two electrodes. For example, an electrode array may comprise at least two electrodes coupled to a common lead body, or may comprise at least one electrode coupled to each of at least two leads. As other examples, an electrode array may include one or more electrodes coupled to at least one lead and a housing of IMD 14 or any number of electrodes coupled to the housing, or may include at least two electrodes coupled to the housing of IMD 14. In some examples, the electrode array includes electrodes coupled to two leads or a single side or the housing, and characteristics of the stimulation field may be defined in a plane characterized by the two leads or the surface of the housing. In other examples, the electrode array may include a more complex three-dimensional structure, as described in further detail below, and characteristics of the stimulation field may be defined in three dimensions.

In the illustrated example, system 10 includes a single IMD 14 to deliver PNFS to a single region 12 in patient 11. In other examples, IMD 14 may be configured to deliver therapy to one or more regions of tissue in which patient 11 feels pain with the aid of lead 16 or more than one lead. Further, some example systems may include more than one IMD 14 for delivery of PNFS to one or more regions in which patient 11 experiences pain. In some examples, PNFS may be delivered alone, or in combination with other therapies, such as spinal cord stimulation (SCS), deep brain stimulation (DBS), cortical stimulation (CS), drug therapy, and the like, as described in U.S. patent application Ser. No. 11/450,133 to Rooney et al., entitled, "COMBINATION THERAPY INCLUDING PERIPHERAL NERVE FIELD STIMULATION," which was filed on Jun. 9, 2006. U.S. patent application Ser. No. 11/450,133 to Rooney et al. is incorporated herein by reference in its entirety.

In the example shown in FIG. 1, lead 16 delivers PNFS to the tissue of patient 11 within a region 12 where patient 11 experiences pain. Lead 16 may be implanted within or between, for example, intra-dermal, deep dermal, or subcutaneous tissues of patient 11 at the region 12 where patient 11 experiences pain to deliver PNFS. These tissues may include skin and associated nerves and muscles and associated nerves or muscle fibers. In the illustrated example, region 12 is an axial region of the lower back of patient 11, but the invention is not limited as such. Rather, lead 16 may be implanted in any region where patient 11 experiences pain. Lead 16 may deliver PNFS to one layer of tissue or multiple layers of a tissue as determined necessary by a clinician.

In some examples, lead 16 extends from IMD 14 to any localized area or dermatome in which patient 11 experiences pain. For example, lead 16 may extend from IMD 14 to position an electrode array at various regions of the back, the back of the head, above the eyebrow, and either over the eye or under the eye, and may be used to treat failed back surgery syndrome (FBSS), cervical pain (shoulder and neck pain), facial pain, headaches, supra-orbital pain, inguinal and pelvic pain, chest and intercostal pain, mixed pain (nociceptive and neuropathic), visceral pain, neuralgia, peroneal pain, phantom limb pain, and arthritis. PNFS may ameliorate pain within the region of implantation by stimulating axons or small nerve fibers in the nearby dermal, subcutaneous, or muscular tissues, or the tissues themselves. The stimulation of these axons or fibers may cause orthodromic action potentials that propagate toward a spinal cord of patient 11, and modulate larger peripheral nerves and dorsal horn cells and/or synapses within the dermatomes that include the pain region, which may reduce pain experienced by patient 11 in that region. The stimulation of these axons or fibers may also cause antidromic action potentials that propagate toward the skin and modulate sympathetic outflow, which may reduce pain mediated by the sympathetic system, such as with some forms of complex regional pain syndrome. Lead 16 is not implanted proximate to larger, peripheral nerves in order to avoid delivery of stimulation to smaller fibers in the nerve, e.g., A-delta fibers, which may result in patient 11 experiencing unpleasant sensations.

Lead 16 may comprise, as examples, a substantially cylindrical lead with ring electrodes, a paddle lead, or a lead with a more complex, three-dimensional electrode array geometry, such as a cylindrical lead with electrodes disposed at various circumferential positions around the cylinder (e.g., with the aid of partial ring electrodes or segmented electrodes disposed at various circumferential positions around a lead having a generally round cross-section). In some examples, as discussed in greater detail below, lead 16 may include electrodes, such as pad electrodes or segmented electrodes, on more than one surface. For example, lead 16 may be a paddle-type lead with electrodes on multiple surfaces, or a multiple level lead, as will be described in greater detail below. In general, the disclosure may be used with a system 10 including any type of lead, and is not limited to the leads described herein, or any particular type of implantable lead.

In some examples, electrodes of therapy system 10, such as electrodes of leads 16 and/or housing of IMD 14, may be partially activated. The illustration of a single lead 16 in FIG. 1 is one example of a configuration of system 10. In other examples, two or more leads 16 may extend to each location that receives stimulation from IMD 14, and each lead 16 may include one or more electrodes. For example, four leads 16, each with two electrodes, may extend to a particular region 12 where patient 11 experiences pain. Leads 16 may be bifurcated, particularly if the number of interfaces that IMD 14 includes for electrically coupling to leads is limited. Although not shown in FIG. 1, in some examples, lead 16 may be indirectly coupled to IMD 14 by one or more extensions.

In addition to or instead of lead 16 comprising electrodes, in other examples, IMD 14 may comprise a housing that includes at least one electrode located on the housing to define an electrode array. IMD 14 may deliver electrical stimulation via combinations of the electrode and the housing surfaces, combinations of two or more electrodes on one or more of the housing surfaces, and, in some cases, via combinations of electrodes on one or more leads 16 and on the IMD housing. In these examples, IMD 14 may have a miniaturized form factor and a low profile that permits implantation within inter-dermal, deep dermal, or subcutaneous tissue of patient 11. For example, IMD 14 may be implanted under a flap of skin in the region 12 where patient 11 experiences pain. These tissues include skin and associated nerves and muscles associated nerves or muscle fibers. IMD 14 may be thin and flat and, in some examples, may be angled or curved to better conform to the tissues at locations where the IMD 14 is implanted.

System 10 also includes a clinician programmer 20. Clinician programmer 20 may, as shown in FIG. 1, be a handheld computing device. In other examples, clinician programmer 20 may be a workstation, a general purpose computer, or the like. Clinician programmer 20 includes a user interface, such as, for example a display 22 and a keypad 24. The display 22 may include, for example a liquid crystal display (LCD) or light emitting diode (LED) display, and may be used to present information relating to PNFS to a user. Keypad 24 may be used by a user, such as a clinician, to interact with clinician programmer 20. Clinician programmer 20 may also include, for example, a joystick or rotational control. In some examples, display 22 includes a touch screen display, and a user may interact with clinician programmer 20 via display 22. A user may also interact with clinician programmer 20 using peripheral pointing devices, such as a stylus or mouse. In some examples, keypad 24 may take the form of an alphanumeric keypad or a reduced set of keys associated with particular functions.

System 10 further includes a patient programmer 18, which also may, as shown in FIG. 1, be a handheld computing device. Patient programmer 18 may include a user interface, such as a keypad 26 and display 28, to allow patient 11 to interact with patient programmer 18. In some examples, display 28 includes a touch screen display, and patient 11 may interact with patient programmer 18 via display 28. Patient 11 may also interact with patient programmer 18 using peripheral pointing devices, such as a stylus or mouse. Further, in some examples, patient programmer 18 may include, for example, a joystick or rotational control.

As will be described in further detail below, patient programmer 18 and/or clinician programmer 20 may allow a user, such as a clinician or patient 11, to provide various inputs that specify a characteristic of a stimulation field for the PNFS ("PNFS field") via the respective user interfaces of the programmers 18, 20 (e.g., keypad 24 or 26, a touch screen, or the like), respectively, according to the techniques described herein. The characteristics of a PNFS field may include, for example, a direction of the current flow within the PNFS field, a breadth of the PNFS field (e.g., a linear dimension of the PNFS field), a size of a focus of the PNFS field, a fiber diameter selectivity of the PNFS, or the depth of the PNFS field relative to a reference point, such as the epidermis of patient 11. Patient programmer 18 and/or clinician programmer 20 may also present user interfaces that enable a user to specify a desired therapeutic effect of the PNFS, as well as to select a desired region within patient 11 for the PNFS from a plurality of selectable regions.

For example, in order to provide a stimulation field vector input that indicates a desired direction of stimulation within the PNFS field, the clinician may use a stylus to draw one or more stimulation field vectors on a touch screen. A user may utilize a reference point to indicate the desired direction of stimulation within the PNFS field. Multiple stimulation field vectors may, for example, share a starting point or an end point. That is, the stimulation vector input may indicate a desired direction of stimulation relative to a reference point. In some examples, the user may provide more than one stimulation vector input. For example, the user may draw two or more stimulation vectors within a user interface provided by programmers 18, 20, where the vectors either share a single starting point or an end point.

In some examples, one or more lead icons may be provided on a display of the programmer 18 or 20, and the user-provided stimulation vector may indicate a direction of stimulation relative to a longitudinal axis of one or more of the leads. In other examples, a user may reference an axis indicated by a single axis accelerometer or an axis of a two-axis or three-axis accelerometer in order to indicate the desired direction of stimulation within a PNFS field. In other examples, the user may provide a stimulation field vector input that indicates a desired direction of stimulation within a PNFS field, where the user references an anatomical reference point to orient the stimulation field vector (e.g., a particular bone or anatomical landmark such as a named nerve fiber).

Programmers 18, 20 may provide an interface that provides different reference points for the user to reference when providing the stimulation field vector input. In other examples, programmers 18, 20 (or another computing device) may not provide a reference point, but may instead provide a representation of region 12 and the user may provide a stimulation field vector input that indicates a desired direction of stimulation within region 12 of the patient's body. In this way, in some examples, the outer border of region 12 may provide a reference point for the stimulation vector input.

For example, the programmer 18, 20 may present an image of the anatomical region of patient near region 12 to which PNFS is delivered, and the user may draw one or more stimulation vectors over the image. The image may include, for example, any one or more of an X-ray image, computer tomography (CT), magnetic resonance image (MRI), diffusion tensor image (DTI), or a fluoroscopic image. The medical image of region 12 may be useful in guiding the user to provide stimulation input that captures a desired anatomical region or nerve of patient 11. For example, the DTI maybe useful in some cases because it illustrates the nerve fibers, and the user may draw the stimulation vector to stimulate particular nerve fibers illustrating in the DTI. In this way, the user may utilize a medical image presented by the programmer 18, 20 to select different nerve fibers (e.g., different sized nerve fibers).

The clinician may use a stylus to draw a stimulation field vector on a touch screen. The programmer 18 or 20 may determine an electrode combination based on the stimulation field vector input, as described in further detail below with reference to FIGS. 7-10B. The electrode combination may include, for example, selection of active electrodes from an array of electrodes for delivering PNFS to region 12, as well as the polarities of the selected electrodes (e.g., an identification of whether an electrode is an anode or cathode). As another example, the clinician may input a vector beginning point and a vector end point using keypad 24 to define a stimulation field vector. The stimulation field vector may indicate a stimulation direction in a region of a body of patient 11 in which patient 11 experiences pain, and a desired direction of PNFS delivery. The stimulation direction may be, for example, a direction of current flow, a direction of electric field lines in the electrical field generated by the PNFS, or a direction of a voltage gradient. As another example, the clinician may manipulate a stimulation field vector displayed via display 22 of programmer 20, e.g., by rotating the stimulation field vector using a rotational control, to be disposed in a desired direction. In some examples, the stimulation field vector may be limited to a finite number of orientations, based on, for example, the ability of possible electrode configurations within an electrode array to produce a stimulation field corresponding to the stimulation field vector.

In some examples, patient programmer 18 or clinician programmer 20 may include a processor, described in further detail below, which receives the stimulation field vector input from the user and determines an electrode configuration including a selection of a first electrode and a second electrode from an electrode array based on the stimulation field vector input by the clinician. The processor may determine the electrode configuration that corresponds to the stimulation field vector input, e.g., the electrode configuration that may produce a stimulation field having a direction of stimulation ("stimulation direction") that corresponds to the stimulation field vector input. The programmer 18 or 20 may communicate the determined electrode configuration, an indication of the determined electrode configuration, or instructions regarding how to modify a current electrode configuration to produce the determined electrode configuration to the IMD 14, which may deliver PNFS to patient 11 according to the determined electrode configuration. In other examples, programmer 18 or 20 may communicate the stimulation field vector input to IMD 14, and IMD 14 may include a processor that determines an electrode configuration based on the stimulation field vector input.

In some examples, the processor may determine the electrode configuration by selecting an electrode configuration from a plurality of electrode configurations stored in a memory of a device, such as patient programmer 18, clinician programmer 20, or IMD 14, based on the stimulation field vector input and any other user input. For example, the processor may select an electrode configuration that produces an electric field most similar to the stimulation field vector input entered by patient 11.

In other examples, the processor may determine a therapy program for PNFS based on the stimulation vector input by generating a therapy program, e.g., by selecting an electrode configuration based on the stimulation field vector input. In other words, in some examples, a user may provide a stimulation field vector input and a processor may generate an electrode configuration that produces a stimulation field having a direction of stimulation that corresponds to the user-provided stimulation field vector.

In some examples, the resultant direction of stimulation may be influenced by other factors in addition to an electrode configuration. For example, the direction of stimulation may be influenced by the dominant direction of current flow from a first electrode to at least one other electrode, the direction of electric field lines within the stimulation field, or the direction of a voltage gradient caused by stimulation signals (e.g., pulses or continuous wave signals) applied to the selected electrodes. Each of these factors may in turn be influenced by, for example, tissue which the stimulation field is applied to. For example, tissue variation (e.g., tissue density or conductivity, which may vary with the type of tissue, such as muscle tissue or nerve tissue) within the region of PNFS (e.g., region 12 in FIG. 1) may change the electrical current propagation from lead 16 in some directions. The processor may implement an algorithm that applies electrical field model equations that define how the electrical field propagates away from an origin location in order to generate an electrode configuration that may be used to achieve a stimulation directed indicated by a vector input.

In some examples, tissue variation within region 12 near electrodes of leads 16 and/or electrodes of a housing of IMD 14 may be determined by an impedance map of electrode to electrode impedances. IMD 14 may determine the impedance of electrical paths including each electrode of therapy system 10 in order to generate such an impedance map. An impedance map may be useful for determining the most energy efficient stimulation paths, e.g., the paths including the electrodes having the lowest relative impedance. In addition, in some examples, the impedance map is useful for using the electrical field model equations that define how the electrical field propagates away from an origin location.

In other examples, for nerves or nerve fields that themselves have directionality, the vector may be influenced by the dominant or most probable direction of action potentials ensuing from PNFS stimulation. As one example, one vector may lie in the direction of orthodromic potentials and another vector might specify antidromic potentials. The processor of programmer 18 or 20 may be use DTI imaging to determine actual fiber alignment, which may be useful for determining the directions of action potentials, such as orthodromic and antidromic potentials, within the tissue of patient 12. In some examples, other factors, such as the action potential of tissue within region 12, the directionality of nerve or nerve fields, and the like, may be considered by the processor when determining the electrode configuration to produce a stimulation field having a direction of stimulation that corresponds to the user-provided stimulation field vector.

In some examples, the stimulation field vector input provided by a user that indicates a desired direction of stimulation within the PNFS field also indicates a desired amplitude or breadth (e.g., linear dimension of a stimulation field) of the PNFS. The magnitude (e.g., as indicated by length or girth) of the stimulation vector input may correspond to a desired amplitude or breadth of stimulation. For example, a particular unit of length (e.g., 1 millimeter) may correspond to a particular unit of amplitude (e.g., 5 volts). The user may input a stimulation vector having a predefined magnitude into programmer 18 or 20 to indicate not only a direction of stimulation within patient 11, but also a stimulation amplitude or breadth. A processor of programmer 18 or 20 may determine the stimulation amplitude or breadth (which may be a function of amplitude as well as other stimulation parameter values) based on the vector input provided by the user.

Again, the programmer 18 or 20 may communicate the determined stimulation amplitude or other parameter values corresponding to the stimulation field vector input, an indication of the determined amplitude or other stimulation parameter values, or instructions regarding how to modify current therapy parameters values to produce the determined parameter values to the IMD 14, which may deliver PNFS to patient 11 according to the determined parameter values. In other examples, programmer 18 or 20 may communicate the stimulation field vector input to IMD 14, and IMD 14 may include a processor that determines stimulation amplitude or other parameter values based on the stimulation field vector input.

In some examples, the processor may also receive other inputs from a user via the user interface of at least one of the programmers 18 or 20 to further define the desired stimulation field. For example, the clinician may provide input indicating a desired focus size of a stimulation field ("stimulation focus"), a stimulation breadth, a nerve fiber diameter selectivity, or a stimulation depth to further define the desired stimulation field, as described in further detail below. The processor may then determine an electrode configuration based on the stimulation field vector input and the other clinician inputs. The nerve fiber diameter selectivity input may indicate the nerve fiber sizes that the PNFS may stimulate. A processor of the programmer 18 or 20 that is used to select nerve fiber diameter may select one or more stimulation parameter values that recruit the user-specified nerve fiber sizes. Examples of stimulation parameters that may affect the nerve fiber sizes that are recruited by the delivery of PNFS to region 12 include, but are not limited to, pulse width or pulse rate. For example, if a user select relative smaller diameter fibers for activating by PNFS, the amplitude of the PNFS may be relatively lower and the pulse width of the PNFS may be relatively high compared to examples in which the user selects relatively large diameter fibers for the target of PNFS.

The clinician may also use clinician programmer 20 to select values for therapy parameters, such as, in the case of PNFS by electrical stimulation pulses, a voltage or current pulse amplitude, pulse width, and a pulse rate or frequency, for the delivery of PNFS by IMD 14. IMD 14 may deliver the PNFS according to one or more therapy programs, where each program includes respective values for each of a plurality of such therapy parameters. In some examples, varying the pulse frequency may allow PNFS to capture target tissues, such as muscle tissue and nerve fibers, or may stimulate the production of endorphins. These physiologic effects of varying the stimulation frequency may be useful for generating a desired therapeutic effect. In some examples, IMD 14 may deliver PNFS according to two or more therapy programs substantially continuously or in an interleaved or alternating fashion.

In some examples, patient 11 may use patient programmer 18 to control other aspects of the delivery of PNFS by IMD 14. For example, patient 11 may use patient programmer 18 to activate or deactivate PNFS, and may use patient programmer to make adjustments to programs, such as adjusting a stimulation intensity. Additionally, the clinician or patient 11 may use programmers 18, 20 to create or adjust schedules for delivery of PNFS.

In some examples, the user interface of patient programmer 18 may also allow a user to select a desired therapeutic effect of PNFS delivery by IMD 14 for a region in a body of patient 11 in which patient 11 experiences pain. Example therapeutic effects include muscle relaxation, muscle activation, pain reduction, or paresthesia. IMD 14 may achieve these therapeutic effects by delivering PNFS at different stimulation frequencies. For example, PNFS delivered with a stimulation pulse frequency of less than about 10 Hz may activate muscle tissue and lead to muscle relaxation. As another example, PNFS delivered with a stimulation pulse frequency of about 10 Hz to about 30 Hz may activate the production of endogenous endorphins, which may reduce pain. As yet another example, PNFS delivered with a stimulation pulse frequency of greater than about 30 Hz may produce paresthesia.

In some examples, the stimulation frequency ranges for producing the listed therapeutic effects may be different than those listed above, and may be determined by a clinician on a patient-specific basis via in-clinic testing or another calibration procedure. The stimulation frequency ranges may also be non-specific to patient 11, and may be based on more general information, such as information from a plurality of patients and the general trend in responses to the different stimulation frequency ranges. In other examples, the therapeutic effect input may directly indicate the stimulation pulse frequency or stimulation pulse frequency range corresponding to the desired therapeutic effect. Regardless of whether patient 11 provides input indicating a desired therapeutic effect by selecting the effect or a stimulation pulse frequency, a processor in patient programmer 18, clinician programmer 20 or IMD 14 may determine a therapy program for delivering PNFS to the region based on the therapeutic effect input.

In some examples, patient 11 may indicate more than one therapeutic effect for a common region of pain, and the processor may select more than one therapy program for the PNFS to the region. IMD 14 may deliver therapy to the region according to the therapy programs substantially simultaneously or on an interleaved or alternating basis. In some examples, a processor of IMD 14 may control IMD 14 to interleave stimulation pulses of different frequencies, which are determined based on the more than one therapeutic effect selected by patient 11. For example, patient 11 may indicate muscle relaxation and pain reduction are desired therapeutic effects, and the processor may determine a first therapy program that defines a first set of stimulation pulses having a frequency of less than about 10 Hz and a second therapy program that defines stimulation pulses delivered at a frequency of about 10 Hz to about 30 Hz. IMD 14 may deliver the stimulation pulses according to the first and second therapy programs substantially simultaneously, or the stimulation pulses defined by the first therapy program may be interleaved with the stimulation pulses defined by the second therapy program.

The user interface of clinician programmer 20 or patient programmer 18 may also allow a user to select at least one region from among a plurality of regions in which patient 11 experiences pain (and to which PNFS can be delivered by IMD 14 via electrodes). The user interface may also allow the user to provide a therapy input that defines an aspect of PNFS for the selected region. In some examples, the therapy input may activate or deactivate PNFS at the selected region. In other examples, the therapy input may indicate a size or focus of PNFS in the at least one region. In other examples, the user may select at least two regions and the therapy input may adjust a relative intensity of the PNFS delivered to the at least two regions. In other examples, the user may select at least two regions, and the therapy input may adjust a balance between the PNFS delivered to the at least two regions. In yet other examples, the user may select a first region and a second region, and the therapy input may shift the PNFS from the first region to the second region, or may adjust the extent to which a first stimulation field produced by delivering PNFS to the first region overlaps the a second stimulation field produced by delivering PNFS to the second region. A processor, e.g., of clinician programmer 20, patient programmer 18, or IMD 14, may determine a PNFS program for providing peripheral nerve field stimulation to the at least one region based on the therapy input.

Each of these programming techniques may be used alone or in combination with one or more of the other programming techniques. For example, clinician programmer 20 may include a user interface that allows a clinician to select at least one region in which patient 11 experiences pain (and to which PNFS can be delivered), input a stimulation field vector for the selected region(s), and adjust the relative intensity of PNFS delivered to the selected region(s) with respect to another region. As another example, patient programmer 18 may include a user interface that allows patient 11 to input a stimulation field vector to select between predetermined electrode configurations, which may be selected by a clinician and stored in a memory of programmer 18 of IMD 14, and input a desired therapeutic effect according to which the IMD 14 delivers PNFS using the electrode configuration. Other combinations of programming techniques are also contemplated.

IMD 14, patient programmer 18, and clinician programmer 20 may, as shown in FIG. 1, communicate via wireless communication. Patient programmer 18 and clinician programmer 20 may, for example, communicate via wireless communication with IMD 14 using any telemetry techniques known in the art. Such techniques may include low frequency or radiofrequency (RF) telemetry, but other techniques are also contemplated. Patient programmer 18 and clinician programmer 20 may communicate with each other using any of a variety of local wireless communication techniques, such as RF communication according to the 802.11 or Bluetooth specification sets, infrared communication according to the IRDA specification set, or other standard or proprietary telemetry protocols.

Patient programmer 18 and clinician programmer 20 need not communicate wirelessly, however. For example, programmers 18, 20 may communicate via a wired connection, such as via a serial communication cable, or via exchange of removable media, such as magnetic or optical disks, or memory cards or sticks. Further, clinician programmer 20 may communicate with one or both of IMD 14 and patient programmer 18 via remote telemetry techniques known in the art, communicating via a local area network (LAN), wide area network (WAN), public switched telephone network (PSTN), or cellular telephone network, for example.

Figure 2:
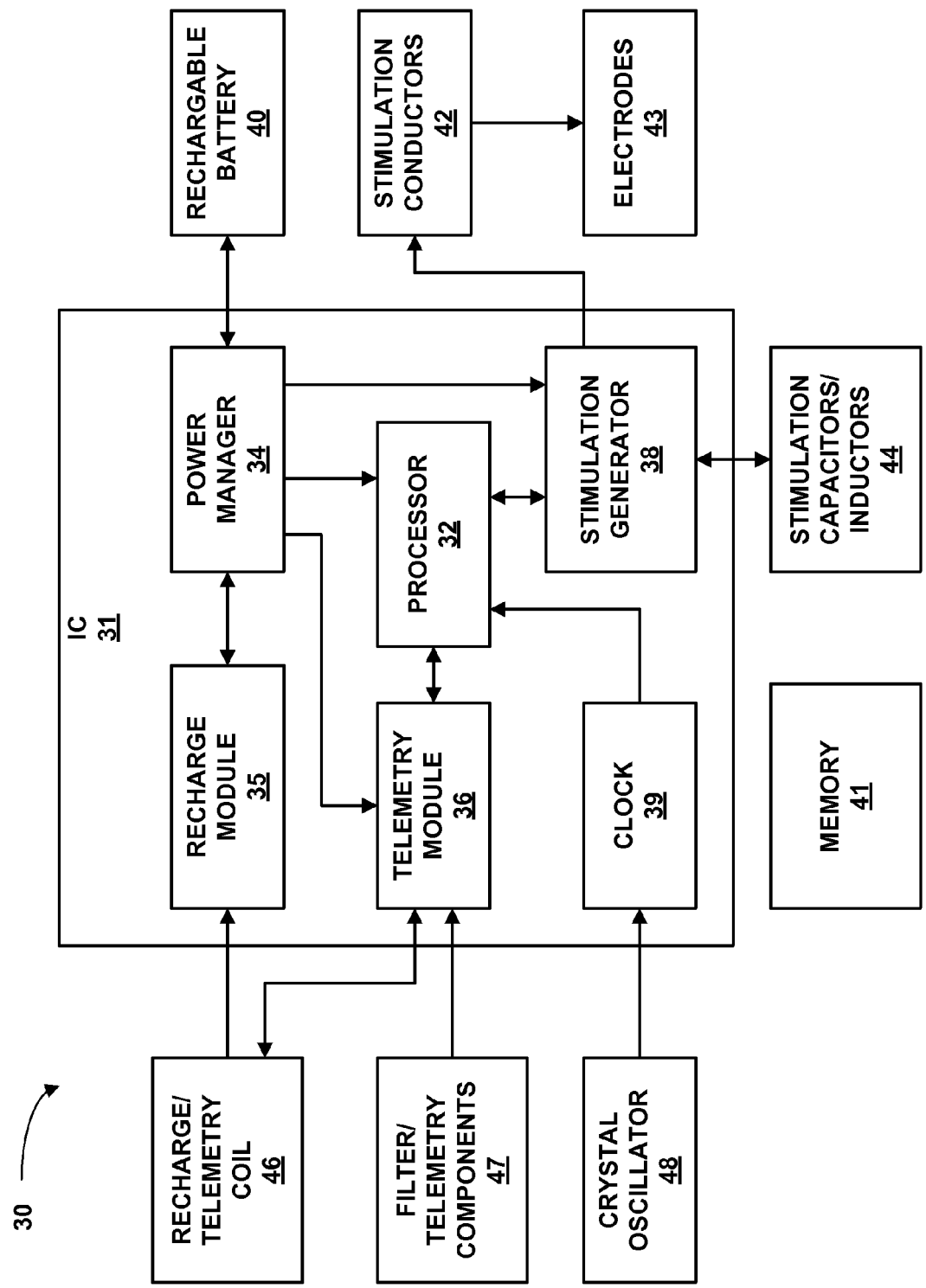
FIG. 2 is a functional block diagram illustrating an example configuration of an implantable medical device.

FIG. 2 is a block diagram illustrating an example control module 30 that may be included in an IMD, such as IMD 14. Control module 30 comprises an integrated circuit (IC) 31, stimulation capacitors and inductors 44, filter and telemetry components 47, and a crystal oscillator 48 that may be positioned on a substrate board. Control module 30 is also coupled to a rechargeable battery 40, stimulation conductors 42 that connect to one or more stimulation electrodes 43 coupled to at least one lead body (e.g., lead 16), and a recharge and telemetry coil 46.

In some examples, IC 31 may comprise one or more of a microprocessor, digital signal processor (DSP), field programmable gate array (FPGA), application specific IC (ASIC), and may include hardware, firmware and/or software for implementing the techniques described herein. Further, in some embodiments, IC 31 may include more than one IC. If implemented in software, a computer-readable medium, e.g., memory 41, may store instructions, e.g., program code, that can be executed by IC 31 to carry out one or more of the techniques described herein. For example the computer-readable medium may comprise magnetic media, optical media, random access memory (RAM), read-only memory (ROM), non-volatile random access memory (NVRAM), electrically erasable programmable read-only memory (EEPROM), flash memory, or other media suitable for storing program code.

IC 31 functionally includes a processor 32, a power manager 34, a recharge module 35, a telemetry module 36, a stimulation generator 38, and a clock 39. In the example shown in FIG. 2, power manager 34 couples to rechargeable battery 40 to provide power to processor 32, recharge module 35, telemetry module 36, and stimulation generator 38. In addition, recharge module 35 couples to recharge and telemetry coil 46 and receives power via the coil to recharge battery 40. Telemetry module 36 also couples to recharge and telemetry coil 46 and may receive stimulation programs and other instructions from a separate device, such as patient programmer 18 or clinician programmer 20, via coil 46.

Filter and telemetry components 47 and power manager 34 couple to telemetry module 36 to help support reliable wireless communication. Examples of filter, power management and telemetry components include a telemetry tank capacitor, voltage regulation filters, power supply filters, and battery bypass capacitors. Telemetry module 36 provides stimulation programs and other information received from programmers 18, 20 to processor 32, which stores the programs in a memory 41. Telemetry module 36, as well as the other telemetry modules described herein, may include, for example, any suitable telemetry circuitry. The memory 41 may also store program instructions that, when executed by processor 32, cause processor 32 to provide the functionality generally ascribed to processors, control modules and IMDs herein.

Crystal oscillator 48 is coupled to clock 39, which clocks processor 32 to run the therapy programs. Processor 32 directs stimulation generator 38 to provide stimulation to the electrodes 43 of lead 16 or housing of IMD 14 via stimulation conductors 42. Processor 32 may direct stimulation generator 38 according to the clock cycle received from clock 39 and the therapy programs received from telemetry module 36 and/or stored in memory 41. In some examples, memory 41 may stored a plurality of therapy programs, and processor 32 may select one or more of the stored therapy programs based on a schedule stored in memory or a signal received from a programmer 18, 20 via coil 46 and telemetry module 36.

Stimulation generator 38 may be a voltage or current pulse generator, and may be coupled to stimulation capacitors and inductors 44, which include capacitors to store energy for stimulation pulses. Stimulation generator 38 may control a switching matrix (not shown) to couple stimulation capacitors and inductors 44 to selected electrodes 43 via their corresponding stimulation conductors 42, as directed by a PNFS program. However, in some cases, IMD 14 may not include a switching matrix.

In some examples, control module 30 may include a greater or fewer number of components. For example, in some cases, multiple memories may be utilized in control module 30. As an example, one memory may be used to store operational protocols, one memory may be used to save any error data, and another memory may store therapy programs for treating the patient. Control module 30 may be configured to conserve energy whenever possible.

As described in further detail below, in some examples, processor 32 of IMD 14 may determine one or more therapy programs for controlling PNFS delivered by IMD 14 based on inputs received from clinician programmer 20 or patient programmer 18 via telemetry module 36. For example, processor 32 may determine an electrode configuration or stimulation amplitude or breadth based on a stimulation vector input received from a clinician programmer 20 or patient programmer 18 via telemetry module 36. In some examples, processor 32 may also determine a therapy program based on input from a user selecting at least one region within patient 11 for delivering the PNFS and based on a therapy input. Again, the inputs may be received from clinician programmer 20 or patient programmer 18 via telemetry module 36. As described in further detail below, the therapy input may comprise an activate or deactivate PNFS command, an indication of a relative intensity of PNFS therapy in at least two regions within patient 11, an indication of size or focus of PNFS therapy in at least one region within patient 11, a balance of PNFS between at least two regions, a shift of PNFS from a first region to a second region, or an extent to which a first stimulation field produced by delivering PNFS to a first region overlaps a second stimulation field produced by delivering PNFS to a second region.

In some examples, processor 32 may also determine a therapy program based on a therapeutic effect input received from one of programmers 18, 20 via telemetry module 36. As described in further detail below, the indicated therapeutic effect may correspond to a stimulation frequency with which IMD 14 delivers PNFS to the region in which patient 11 experiences pain. In some examples, determining a therapy program may comprise selecting a therapy program stored in memory 41 of IMD 14 or a memory 54, 74 of one of programmers 18, 20 based on the therapeutic effect input. In other examples, determining a therapy program may comprise generating a therapy program based on the therapeutic effect input.

Figure 3:
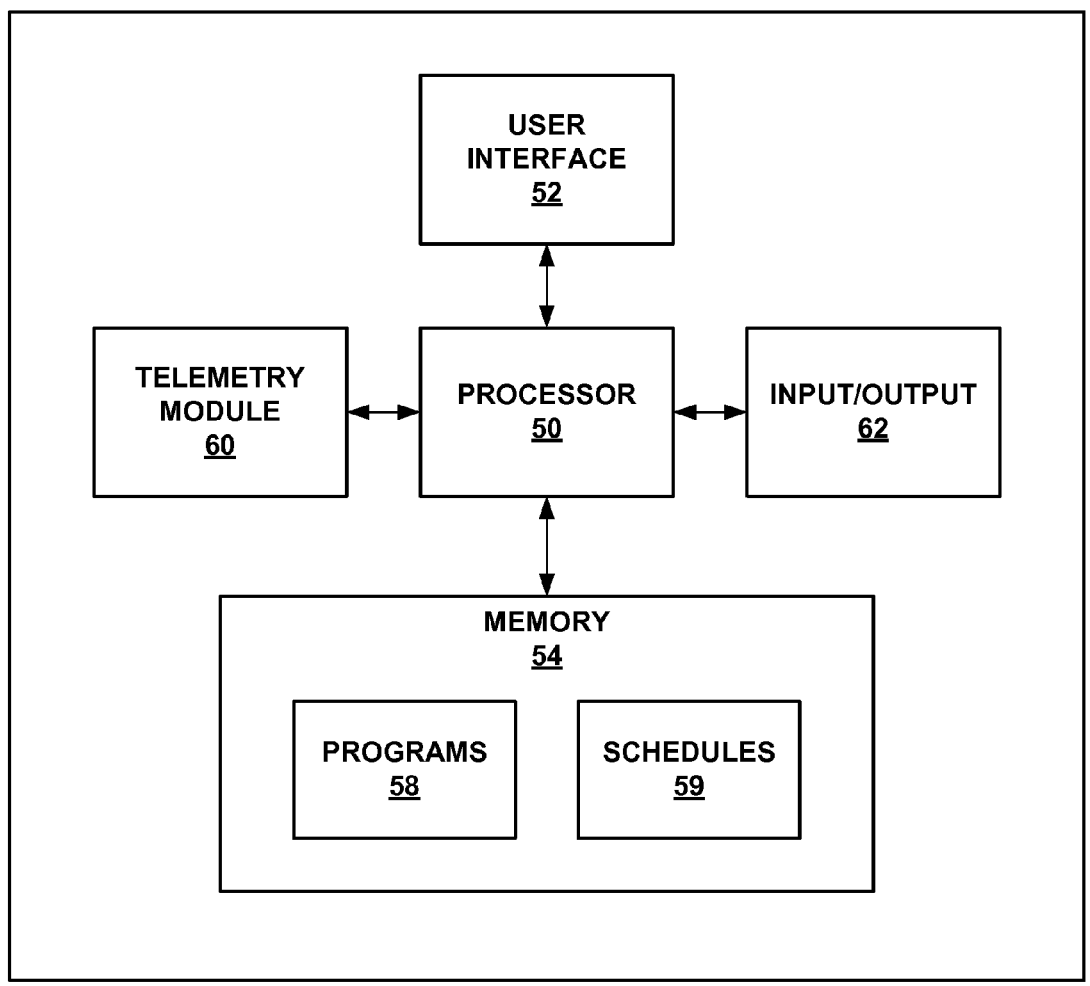
FIG. 3 is a functional block diagram illustrating an example configuration of a patient programmer.

FIG. 3 is a block diagram illustrating an example configuration of patient programmer 18. Patient 11 may interact with a processor 50 via a user interface 52 in order to control delivery of PNFS by an IMD, such as IMD 14. User interface 52 may include a display and a user input mechanism, such as a keypad, joystick, or rotational control, and may also include a touch screen or peripheral pointing devices, such as a stylus, mouse, or the like. Processor 50 may also provide user interface screens via the display of user interface 52 to facilitate interaction with patient 11. Processor 50 may include any one or more of a microprocessor, a controller, a DSP, an ASIC, an FPGA, discrete logic circuitry, or the like, and functions described herein may be embodied as hardware, software, firmware or any combination thereof.

Patient programmer 18 also includes a memory 54. In the example shown in FIG. 3, memory 54 stores therapy programs 58 that are available to be selected by patient 11 for delivery of stimulation. Therapy programs 58 define one or more stimulation parameter values, such as the electrodes 43 (FIG. 2) that are activated, the polarity of the selected electrodes 43, a current or voltage amplitude and, in the case of stimulation in the form of electrical pulses, pulse width and pulse rate (or frequency) for stimulation signals to be delivered to patient 11. In the example shown in FIG. 3, memory 54 also stores schedules 59, which may specify the times at which, and, in some cases, the order with which particular therapy programs 58 are to be delivered by IMD 14. Memory 54 may also include program instructions that, when executed by processor 50, cause patient programmer 18 to perform the functions ascribed to patient programmer 18 herein. Memory 54 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Figure 4:
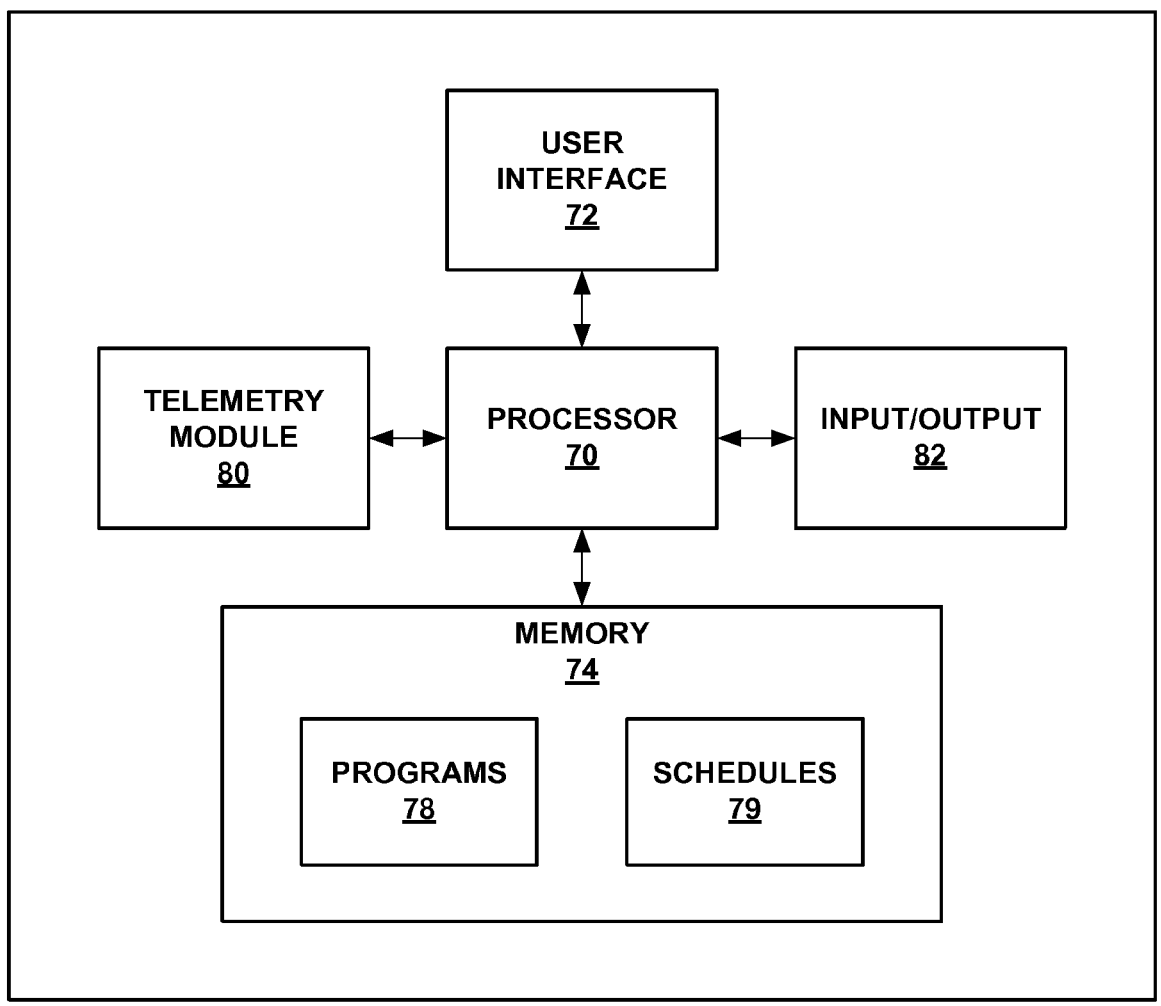
FIG. 4 is a functional block diagram illustrating an example configuration of a clinician programmer.

Patient programmer 18 also includes telemetry module 60 that allows processor 50 to communicate with IMD 14, and input/output circuitry 62 that allows processor 50 to communicate with processor 70 of clinician programmer 20 (FIG. 4). Processor 50 may receive therapy program selections made by patient 11 via user interface 52, and may either transmit the selection or the selected program to IMD 14 via telemetry module 60 for delivery of PNFS by IMD 14 according to the selected program. Further, processor 50 may select one or more therapy programs 58 according to a stored schedule 59, and may either transmit the selection or the selected program to IMD 14 via telemetry module 60 for delivery of stimulation according to the selected program. In examples in which patient programmer 18 stores programs 58 in memory 54, processor 50 receives programs 58 from clinician programmer 20 via input/output circuitry 62 during programming by a clinician. Circuitry 62 may include, for example, transceivers for wireless communication, appropriate ports for wired communication or communication via removable electrical media, or appropriate drives for communication via removable magnetic or optical media.

In some examples, processor 50 determines the one or more therapy programs for delivery of PNFS by IMD 14 based on inputs received from a user, such as a clinician or patient 11, via user interface 52. As described above, the inputs may include one or more stimulation field vector inputs that indicates a direction of current flow, a direction of electric field lines, or a direction of a voltage gradient caused by stimulation signals applied to selected electrodes in a region of a body of patient 11 in which the patient 11 experiences pain. In some examples in which the user provides more than one stimulation vector, the stimulation vectors may share a starting point or an end point. Each of the therapy programs 58 stored in memory 54 of patient programmer 18 may include a predetermined electrode configuration selected by a clinician. Processor 50 may select a therapy program from among the stored therapy programs 58 that produces a stimulation direction that is similar to the stimulation field vector. For example, in some embodiments, processor 50 may select the program from among programs 58 that produces a stimulation direction that is most similar to the stimulation field vector input by patient 11.

In other examples, processor 50 receives a stimulation field vector from patient 11 via user interface 52, and generates an electrode configuration (or other stimulation parameter values) to produce a stimulation direction corresponding to the stimulation field vector. In examples such as these, therapy programs 58 may include predetermined therapy parameter values (e.g., determined by a clinician), such as a voltage or current pulse amplitude, pulse width, and a pulse rate, while enabling changes to the electrode configuration. Accordingly, when patient 11 inputs a stimulation field vector, processor 50 may determine an electrode configuration based on the stimulation field vector, and control IMD 14 to deliver PNFS using the determined electrode configuration and the predetermined therapy parameters of the currently selected program. In some cases, processor 50 may store the determined electrode configuration within memory 54, e.g., as a part of a therapy program 58.

In other examples, processor 50 may transmit the stimulation field vector to telemetry module 36 of IMD 14 (FIG. 2) via telemetry module 60. Processor 32 of IMD may receive the stimulation field vector from telemetry module 36 and determine an electrode configuration (or other stimulation parameter values) for producing the inputted stimulation direction. In some examples, processor 32 may select a predetermined therapy program stored in memory 41 (FIG. 2) of IMD 14, where the therapy program includes an electrode configuration that produces a stimulation direction similar to the direction indicated by the stimulation field vector, while in other examples, processor 32 may generate a therapy program based on the stimulation field vector input.

In some examples, processor 50 also determines a PNFS therapy program for controlling therapy delivery by IMD 14 based on a region selection input selecting at least one region in which patient 11 experiences pain via user interface 52. Processor 50 may also receive a therapy input defining an aspect of PNFS for the selected region(s) via user interface 52, such as the activation or deactivation of PNFS, a size or focus of PNFS therapy in at least one region within patient 11, a nerve fiber diameter selection, a relative intensity of PNFS in at least two regions within patient 11, a balance of PNFS between at least two regions, a shift of PNFS from a first region to a second region or an extent to which a stimulation field produced by delivering PNFS to a first region overlaps a stimulation field produced by delivering PNFS to a second region. In some examples, processor 50 determines a therapy program based on the therapy input. For example, processor 50 may select from predetermined therapy programs 58 selected by a clinician and stored in memory 54 based on the therapy input. In other examples, processor 50 may generate a therapy program based on the therapy input.

In other examples, processor 50 of patient programmer 18 transmits the region selection input and the therapy input to processor 32 of IMD 14 via the respective telemetry modules 60, 36. Processor 32 of IMD 14 may then determine the therapy program for delivery of PNFS to patient 11 based on the therapy input or select from predetermined PNFS programs selected by a clinician and stored in memory 41 of IMD 14 based on the therapy input.

In some examples, processor 50 of patient programmer 28 may receive a therapeutic effect input from patient 11 via user interface 52 and determine a therapy program based on the therapeutic effect input. As described in further detail below, the therapeutic effect input may indicate a stimulation frequency of the PNFS delivered to the one or more regions in which patient 11 experiences pain. Processor 50 may determine a therapy program for delivering PNFS to the region based on the therapeutic effect input. In some examples, processor 50 selects from stored therapy programs 58 based on the therapeutic effect input. In other examples, processor 50 receives a therapeutic effect input from patient 11 via user interface 52 and transmits the therapeutic effect input to processor 32 of IMD 14 via the respective telemetry modules 60, 36. Processor 32 of IMD 14 may determine a therapy program based on the therapeutic effect input, which may include a selecting from therapy programs selected by a clinician and stored in memory 41 of IMD 14.

FIG. 4 is a functional block diagram illustrating an example configuration of clinician programmer 20, which includes components similar to the example of patient programmer 18 shown in FIG. 3. In the example shown in FIG. 4, clinician programmer 20 includes processor 70, user interface 72, memory 74, telemetry module 80, and input/output 82. A clinician may interact with a processor 70 via a user interface 72 in order to program delivery of stimulation by IMD 14. User interface 72 may include a display and user input mechanism, such as a keypad, and may additionally or alternatively, include a touch screen or peripheral pointing devices, such as a stylus, mouse, or the like. Processor 70 may present user interface screens to a user via the display of user interface 72 in order to facilitate interaction with a clinician, as will be described in greater detail below. Processor 70 may include any one or more of a microprocessor, a controller, a DSP, an ASIC, an FPGA, discrete logic circuitry, or the like. The functions attributed to processor 70 herein, as well as the other processor described herein, may be embodied as software, firmware, hardware or any combination thereof.

Clinician programmer 20 also includes a memory 74. Memory 74 may include program instructions that, when executed by processor 70, cause clinician programmer 20 to perform the functions ascribed to clinician programmer 20 herein. Memory 74 may include any combination of volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

In some examples, processor 70 determines therapy programs for controlling delivery of PNFS by IMD 14 based on input received from a clinician via user interface 72. For example, the clinician may provide a stimulation field vector input via user interface 72, such as by drawing, rotating, or diagramming a stimulation field vector on a touch screen display. The stimulation field vector may indicate a desirable direction of stimulation in a region of a body of patient 11 in which the patient 11 experiences pain. In some examples, processor 70 determines an electrode configuration (or other stimulation parameter values) that produces the stimulation direction when IMD 14 delivers therapy with the electrodes of the electrode configuration and the respective polarities indicated by the configuration. As an example, the electrode configuration may include a first electrode, a second electrode, and a polarity of the first and second electrodes. For example, the first electrode may include an anode electrode and the second electrode may include a cathode electrode. Processor 70 may transmit the electrode configuration to IMD 14 via telemetry module 80, and IMD 14 may deliver PNFS according this electrode configuration and the therapy parameters stored in a selected program. In other examples, processor 70 may transmit an indication of a therapy program to IMD 14, which may store the parameter values, including the electrode configuration, within memory 41. The indication may be, for example, an alphanumeric indicator or a symbol that is associated with the therapy program in memory 41.

In other examples, processor 70 may transmit the stimulation field vector indicated by the clinician to telemetry module 36 of IMD 14 (FIG. 2) via telemetry module 80 of clinician programmer 22. Processor 32 of IMD 14 may receive the stimulation field vector from telemetry module 36 and determine an electrode configuration or other stimulation parameter values (e.g., stimulation signal amplitude) for producing the stimulation field having the desired direction of stimulation.

In some examples, processor 70 may also receive a region selection input from a user via user interface 72 that indicates at least one region in which patient 11 experiences pain. Processor 70 may also receive a therapy input defining an aspect of PNFS for the selected region(s) via user interface 72. In some examples, processor 70 may determine a therapy program based on the therapy input. In other examples, processor 70 may transmit the region selection input and the therapy input to processor 32 of IMD 14 via the respective telemetry modules 80, 36, and processor 32 may determine the therapy program based on the therapy input. As described in further detail below, the therapy input may comprise an activate or deactivate PNFS command, a size or focus of PNFS therapy in the at least one region, a relative intensity of PNFS therapy in at least two regions, a balance of PNFS between at least two regions, a shift of PNFS from a first region to a second region, or an extent to which a stimulation field produced by delivering PNFS to a first region overlaps a stimulation field produced by delivering PNFS to a second region.

In some examples, processor 70 also transmits therapy parameter limits to processor 32 of IMD 14 (FIG. 2) or processor 50 of patient programmer 18 (FIG. 3), which limit the extent to which patient 11 or another user may make changes or control the PNFS therapy. For example, a clinician may determine and input a number of electrode configurations from which patient 11 may select, and input these electrode configurations into clinician programmer 20, which then transmits these preselected electrode configurations to processor 32 of IMD 14 or processor 50 of patient programmer 18. IMD 14 or programmer 18 may store the electrode configurations in memory 41, 54. Patient 11 may then be able to select from the electrode configurations by inputting a stimulation field vector, based on which processor 32 or 50 selects one of the stored electrode configurations. Similarly, the clinician may also determine limits for other therapy parameters, such as, for example, minimum or maximum stimulation breadths, minimum or maximum focus sizes, minimum or maximum relative intensities, minimum or maximum shifting rates, allowable shifts, maximum or minimum extents of stimulation field overlap, and the like. The clinician may input one or more of these limits into clinician programmer 20, and processor 70 may transmit the limits to processor 32 or 50 using telemetry module 80. Patient 11 may then select from therapy programs that include therapy parameters within the limits determined by the clinician.

The clinician may test any number of therapy programs 78 for implementation of PNFS for patient 11. Processor 70 may transmit therapy programs 78 selected by the clinician, e.g., based on patient feedback, to IMD 14 via telemetry module 80, or to patient programmer 18 via input/output circuitry 82. The clinician may also interact with processor 70 to specify therapy schedules 79 for delivery of therapy, which the processor may transmit to IMD 14 via telemetry module 80, or to patient programmer 18 via input/output circuitry 82. I/O circuitry 82 may include transceivers for wireless communication, appropriate ports for wired communication or communication via removable electrical media, or appropriate drives for communication via removable magnetic or optical media.

Figure 5:
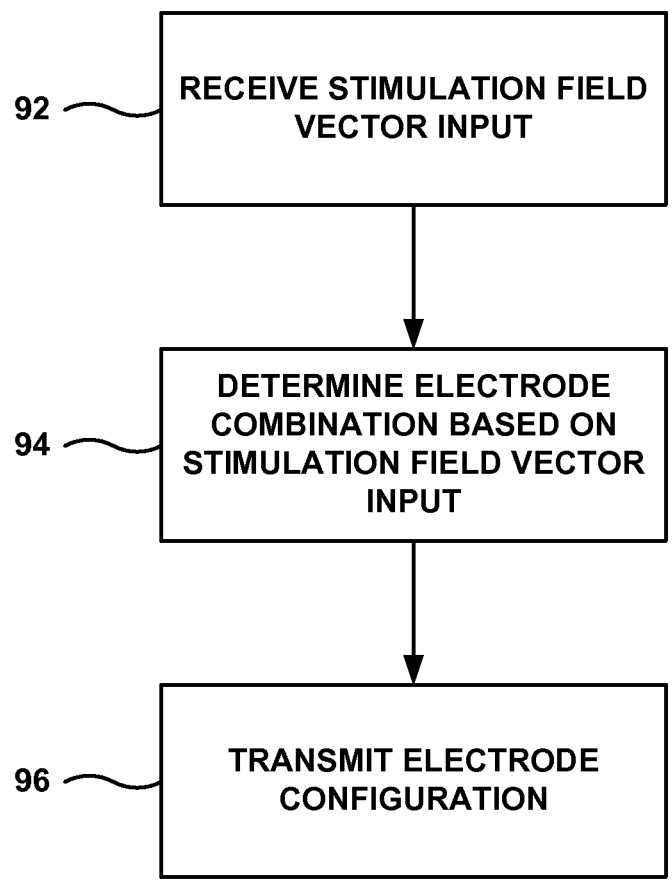
FIG. 5 is a flow diagram illustrating an example technique for programming a medical device using vector-based techniques.

FIG. 5 is a flow diagram illustrating an example technique for programming an IMD, such as IMD 14, to provide PNFS to a tissue area in a patient. The technique shown in FIG. 5 is described with reference to user interface 72 and processor 70 of clinician programmer 20. However, as described above, in some examples, user interface 52 of patient programmer 18 may also accept a stimulation field vector input, and processor 50 of patient programmer 18 or processor 32 of IMD 14 may perform the functions ascribed to processor 70 of clinician programmer 20. Accordingly, in other embodiments, processors 32 or 50 may also perform the technique shown in FIG. 5.

In accordance with the technique shown in FIG. 5, processor 70 receives a stimulation field vector input (92) from a user, such as a clinician or patient, via user interface 72. The stimulation field vector input may include one or more stimulation field vectors. As previously described, in some examples, user interface 72 may include a touch screen that may be used with or without a stylus, a mouse, a keypad, a rotational control, a joystick, or the like, with which the user may enter or manipulate the stimulation field vector. The user interface 72 may display a user interface screen, such as, for example, one or more of the screens shown in FIGS. 9A-13C, which may prompt the user to enter the stimulation field vector input and other inputs indicating attributes of the stimulation field.

The stimulation field vector input may indicate a direction of stimulation within the stimulation field generated by IMD 14 in a region of a body of a patient 11 in which patient 11 experiences pain. That is, the stimulation field vector input may specify a direction in which the user desires stimulation current to flow (or similarly, the direction which a stimulation voltage is caused by pulses applied to selected electrodes or the direction of electric field lines) between electrodes in an electrode array. The region in which the patient 11 experiences pain may include, for example, a region in a back, arm, shoulder, leg, neck, face, or the like.

In the example illustrated in FIG. 5, processor 70 determines an electrode configuration based on the stimulation field vector input (94). The electrode configuration may include a selection of electrodes for delivering PNFS, the polarity of the selected electrodes, and, in some examples, an indication of whether the electrodes are fully or partially activated. In some examples, the electrode configuration includes a selection of at least a first electrode and a second electrode from the electrode array implanted in or proximate to the region in which the patient 11 experiences pain. In some examples, the electrode array may include at least two electrodes coupled to a common lead body. In other examples, the electrode array may include at least one electrode coupled to each of at least two leads or a housing of IMD 14. The electrode array may be implanted such that a stimulation field may be produced that affects substantially the entire region in which patient 11 experiences pain. In some examples, the electrode configuration includes an arrangement of the first electrode and the second electrode within the electrode array. Further, in some examples, the first electrode may comprise one or more anode electrodes and the second electrode may comprise one or more cathode electrodes.

IMD 14 may utilize the determined electrode combination to deliver PNFS to patient 11 and generate the user-indicated stimulation field in the region in which patient 11 feels pain, or proximate to this region, via electrodes electrically coupled to IMD 14. Accordingly, once processor 70 determines the electrode configuration, processor 70 may transmit the electrode configuration (96) to IMD 14 via the respective telemetry modules 80, 36.

Processor 32 of IMD 14 may receive the electrode configuration from telemetry module 36 and controls stimulation generator 38 to deliver PNFS according to the electrode configuration and other stimulation parameters, such as stimulation voltage or current amplitude, stimulation pulse width, and the like, which may be transmitted by processor 70 along with the electrode configuration as part of a program, or may be stored in memory 41 of IMD 14. In other examples, processor 70 may transmit the determined stimulation parameter values to patient programmer 18 via the respective telemetry modules 80, 60. For example, patient programmer 18 may act as an intermediary telemetry link with IMD 14.

In other examples, rather than transmitting the determined electrode combination to IMD 14, processor 70 may merely transmit an indication of the electrode combination, which may be stored within memory 41 of IMD 14. For example, as described in further detail below, processor 70 of clinician programmer 20 may determine an electrode configuration by selecting from a set of predetermined electrode configurations stored in memory 74 (FIG. 4). Upon selecting the predetermined electrode configuration, processor 70 may transmit the configuration to IMD 14 or an indication of the configuration (e.g., an alphanumeric or symbolic indication), if IMD 14 stores a similar set of electrode configurations that are associated with similar indications.

In yet other examples, processor 70 transmits an operation to IMD 14, such as information that instructs processor 32 of IMD 14 to modify a current electrode configuration or another stored electrode configuration. For example, the operation may comprise enabling or disabling one or more electrode, configuring one or more electrodes as an anode electrode or a cathode electrode, or the like. Processor 32 may configure electrodes within the electrode array accordingly based on the existing configuration and the operation, to produce the determined electrode configuration.

In some examples, the stimulation field vector input also indicates a desired amplitude or a breadth of stimulation. For example, the user may modify a magnitude of one or more inputted stimulation vectors to indicate a desired amplitude for PNFS or a desired breadth (e.g., width of a stimulation field) for the PNFS. The relative size of the inputted stimulation vectors (e.g., the length or width) may directly correlate to a relative amplitude or breadth of stimulation e.g., from a starting point. For example, the user may increase the length of an inputted stimulation field vector to increase the amplitude from a starting amplitude, which may be, e.g., about 0 volts to about 10 volts. Each incremental length change of the stimulation field vector may correspond to an incremental increase of the stimulation amplitude. As another example, the user may increase the width or the girth (in three dimensions) of an inputted stimulation field vector in order to increase the breadth of a desired PNFS field from a starting point, e.g., a selected stimulation field size, which may be presented on a display of programmer 20. Each incremental width or girth change of the stimulation field vector may correspond to an incremental increase of the stimulation breadth.

Processor 70 may determine a stimulation amplitude or other parameters to achieve an inputted stimulation breadth and transmit the determined stimulation parameter values to IMD 14 via the respective telemetry modules 80, 36. In other examples, processor 70 may transmit the determined stimulation parameter values to patient programmer 18 via the respective telemetry modules 80, 60. For example, patient programmer 18 may act as an intermediary telemetry link with IMD 14.

Figure 6:
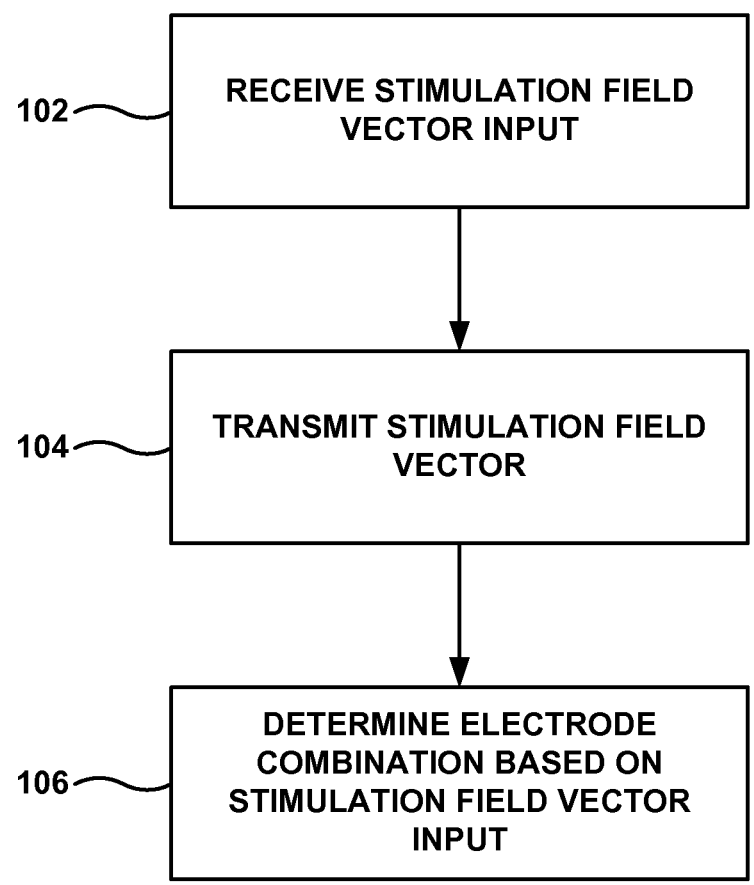
FIG. 6 is a flow diagram illustrating another example technique for programming a medical device using vector-based techniques.

In other examples of the technique shown in FIG. 5, such as in the example technique shown in FIG. 6, processor 70 of clinician programmer 20 may receive the stimulation field vector input from a user (102) via user interface 72 and transmit the stimulation field vector input to IMD 14 via the respective telemetry modules 80, 36 (104). Processor 32 of IMD 14 may receive the stimulation field vector input via telemetry module 36 and determine an electrode configuration based on the stimulation field vector (106). In examples in which the stimulation field vector input also indicates a desired stimulation amplitude of breadth, processor 32 of IMD 14 may also determine the stimulation amplitude or other stimulation parameter values based on the stimulation field vector input.

Figure 7:
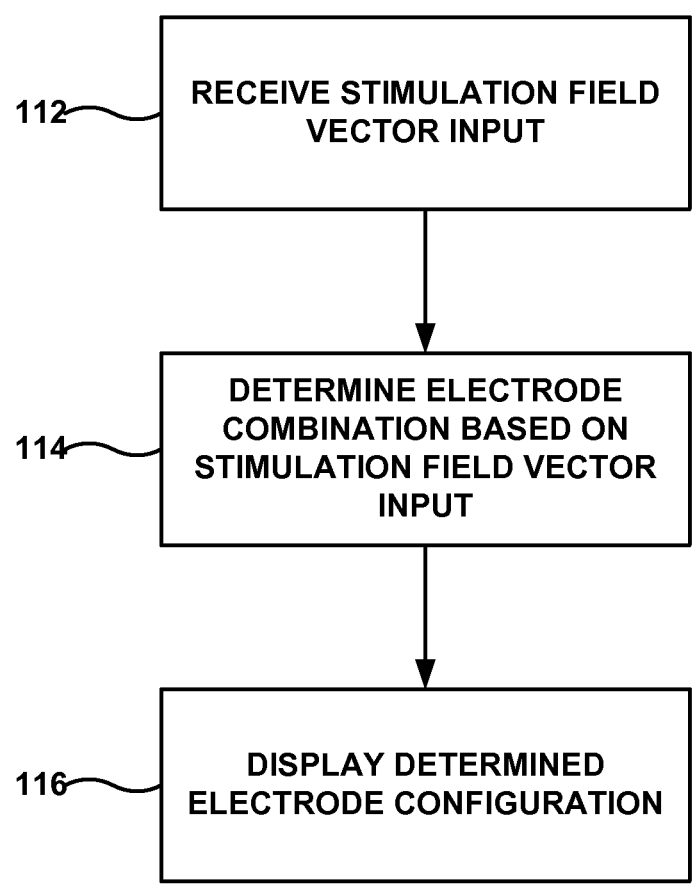
FIG. 7 is a flow diagram illustrating another example technique for programming a medical device using vector-based techniques.

As shown in FIG. 7, in some examples, processor 70 receives the stimulation field vector input from a user (112), e.g., via user interface 72. Processor 70 determines an electrode configuration (also referred to as an "electrode combination") based on the stimulation field vector (114), or processor 70 may transmit the stimulation field vector to IMD 14 or another device, which may then determine the electrode configuration based on the stimulation field vector. In the example illustrated in FIG. 7, processor 70 also displays the determined electrode configuration (116) via user interface 72 of clinician programmer 20. In examples in which processor 70 determines the electrode configuration based on the stimulation field vector, processor 70 may simply update a user interface 72 (e.g., display 22) to display the electrode configuration. In examples in which a processor of another device, such as IMD 14, determines the electrode configuration, the other device may transmit the electrode configuration to processor 70, and processor 70 may update user interface 72 (e.g., display 22) to display the received electrode configuration.

Figure 8:
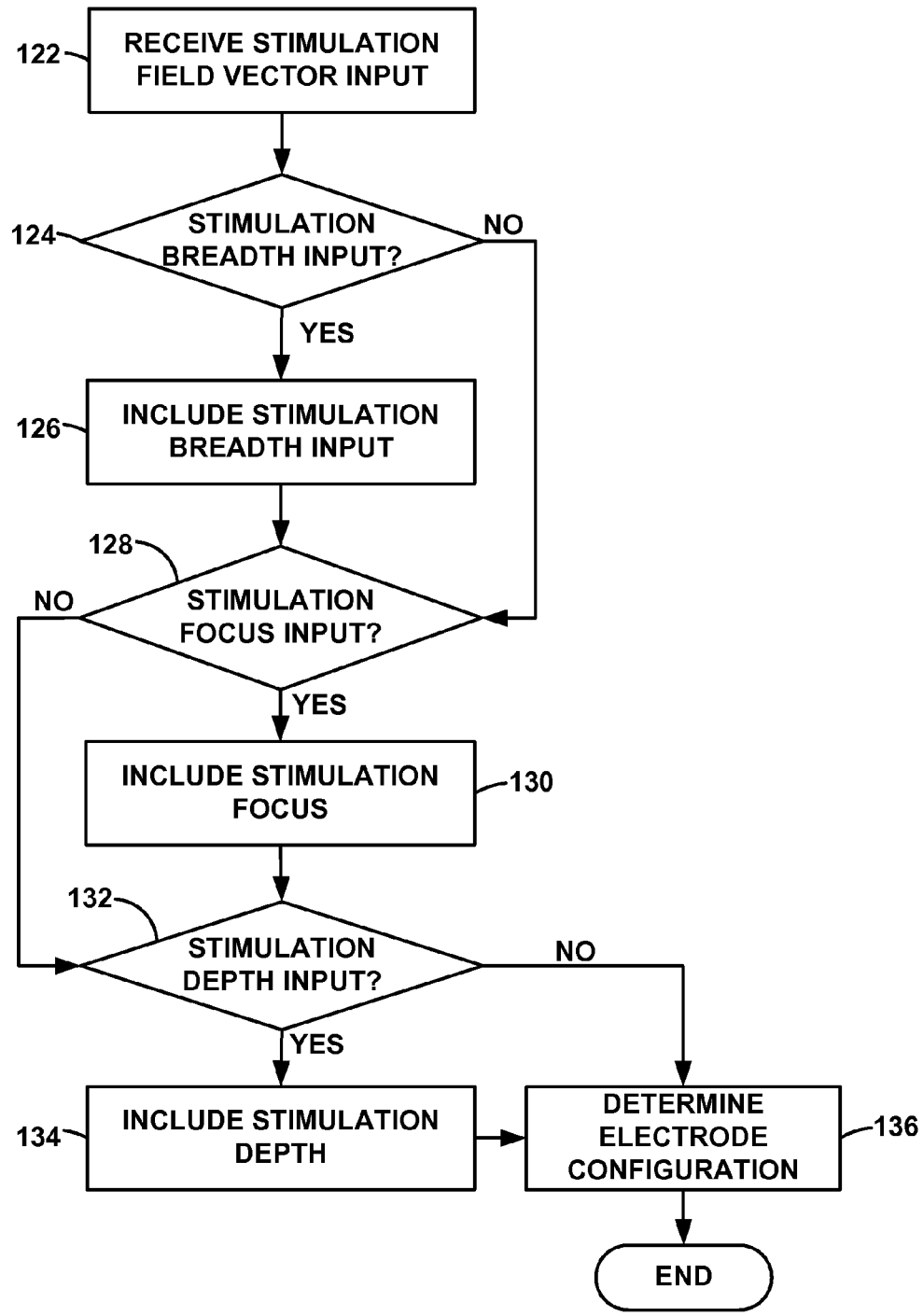
FIG. 8 is a flow diagram illustrating another example technique for programming a medical device using vector-based techniques.

FIG. 8 illustrates a flow diagram illustrating an example technique for determining an electrode configuration based on a stimulation field vector input, as well as other inputs relating to characteristics of the PNFS field. Stimulation field characteristics may generally refer to the size (e.g., volume or a cross-sectional size, such as a linear dimension), focus of stimulation, depth of stimulation relative to a reference point, and the like. While FIG. 8 is primarily described with respect to processor 70 of clinician programmer 20, in other examples, a processor of another device, such as IMD 14 or patient programmer 18, may determine an electrode configuration based on a stimulation field vector input and other stimulation field characteristic inputs using the technique shown in FIG. 8. In the example technique shown in FIG. 8, processor 70 receives a stimulation field vector (122) from a user, such as a clinician. Processor 70 presents a screen to the user via user interface 72 inquiring whether the user wishes to enter a stimulation breadth input (124).

Processor 70 may, for example, determine a relative distance between a first electrode and a second electrode based on the stimulation breadth input. The distance may be, for example, between electrodes of a single lead (e.g., a separation distance along the same lead) or a separation between electrodes on different leads or housing of IMD 14. For example, if three leads are implanted within patient 11, processor 70 may select electrodes from the leads closest together to generate a small breadth of stimulation or select electrodes from the leads furthest apart to generate a larger breadth of stimulation.

Figure 11A:
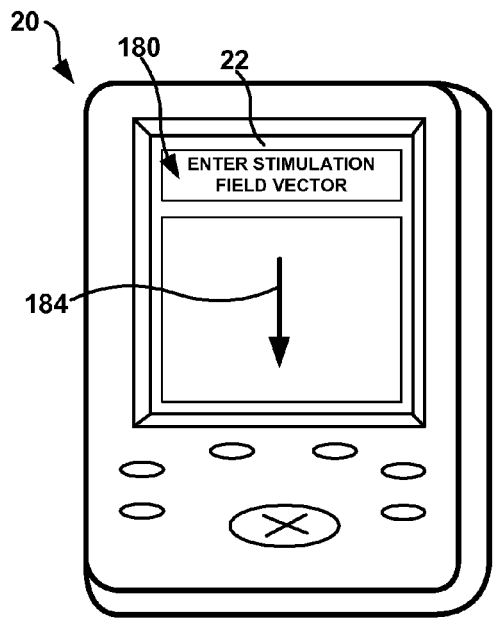
FIGS. 11A-11D illustrate example user interfaces that may be displayed by a programmer for receiving input indicating a stimulation field vector and a stimulation breadth, and displaying an electrode configuration determined based on the input.
Figure 11B:
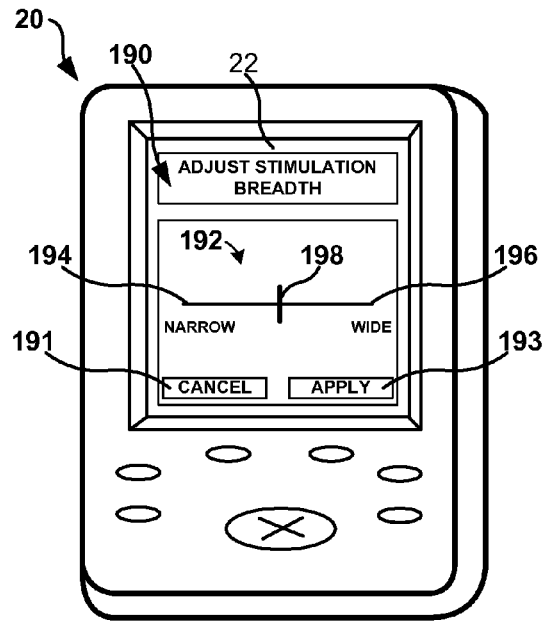

In one example, processor 70 presents a user interface screen, via user interface 72, which is similar to user interface screen 190 of FIG. 11B. If the user enters a stimulation breadth input, processor 70 may consider the stimulation breadth input when determining the electrode configuration (126), and presents a user interface screen that inquires whether the user wishes to enter a stimulation focus (128). If the user does not enter a stimulation breadth input, processor 70 presents the user interface screen that inquires whether the user wishes to enter a stimulation focus input (128).

Processor 70 may, for example, determine a number of cathode electrodes based on the stimulation focus input. For example, by including more cathode electrodes, the focus of the stimulation may decrease. That is, the stimulation may be spread over a larger area. Conversely, including fewer cathode electrodes may increase the focus of the stimulation. In other examples, processor 70 may determine a number of anode electrodes, or a number of anode electrodes and a number of cathode electrodes based on the stimulation focus input. To give focus (e.g., a field shape) more resolution, processor 70 may vary the number and placement of anodes. For example, an electrode combination including a few cathodes and anodes that are closer together may result in a more focused stimulation field. On the other hand, an electrode combination including a greater number of cathodes and anodes that are further separated from each other may result in a less focused stimulation field.

When a user enters a stimulation focus input, processor 70 may determine an electrode configuration based on the stimulation focus input (130) and prompt the user to provide a stimulation depth input (132). If the user declines to enter a stimulation focus input, processor 70 may prompt the user to provide a stimulation depth input (132). Processor 70 may determine a desired distance of the stimulation provided by IMD 14 relative to the surface of the skin of a patient 11 based on the stimulation depth input. The relative depth of stimulation may be controlled by selecting electrodes at varying depths below the skin of patient 11. An implanted electrode array that is implanted in the region 12 in which the patient experiences pain and is coupled to a stimulation generator of IMD 14 may have electrodes at different distances from the skin surface of patient, thereby enabling processor 70 to select electrodes at different depths relative to the skin surface. For example, if IMD 14 includes electrodes on an outer housing, electrodes may be located on different surfaces (e.g., opposing surface). As another example, the implanted electrode array may include at least one lead 16 that includes a three-dimensional electrode array. For example, the lead 16 may include pad electrodes on more than one surface, may include electrode disposed at various circumferential positions around a cylindrical lead body, or may be a multiple level lead. In some embodiments, the electrode array may be defined by electrodes on multiple leads that are implanted at different depths below the skin surface of patient 11.

Example leads with electrodes on multiple surfaces or multiple levels are described in commonly-assigned U.S. patent application Ser. No. 11/450,133 to Rooney et al., entitled, "COMBINATION THERAPY INCLUDING PERIPHERAL NERVE FIELD STIMULATION," which was previously incorporated by reference. Example medical devices with electrodes on at least two surfaces of the housing are described in commonly-assigned U.S. patent application Ser. No. 11/450,127 to Rooney et al., entitled, "IMPLANTABLE MEDICAL DEVICE WITH ELECTRODES ON MULTIPLE HOUSING SURFACES," which was filed on Jun. 9, 2006. U.S. patent application Ser. No. 11/450,127 to Rooney et al. is incorporated herein by reference in its entirety.

When the user enters a stimulation depth input, processor 70 may include the stimulation depth when determining the electrode configuration (134), and determine the electrode configuration (136) based on the stimulation breadth input, stimulation focus input, and stimulation depth input, if entered by the user. If the user declines to input a stimulation depth, the processor 70 may determine the electrode configuration without the stimulation depth input (136).

In some examples, processor 70 prompts the user to enter greater or fewer additional stimulation field characteristics. For example, processor 70 may prompt a user to enter a stimulation breadth input and a stimulation focus input, but not a stimulation depth input. As another example, processor 70 may prompt the user to enter a stimulation breadth input, a stimulation focus input, a stimulation depth input, and a therapeutic effect input (which will be described in further detail below). Further, although processor 70 prompts the user to enter input relating to the stimulation depth, stimulation focus, nerve fiber size, and stimulation depth in a particular order, the disclosure is not so limiting. In other examples, processor 70 may prompt and receive input from the user relating to the stimulation depth, stimulation focus, and stimulation depth in any suitable order.

FIGS. 9A-13C are example user interface screens presented by a processor of a computing device, such as patient programmer 18 or clinician programmer 20. In the following examples, the user interface screens are described with respect to two-dimensional electrode arrays, where the characteristics of the stimulation field are defined in substantially two dimensions. Similar user interface screens may allow a user to define characteristics of the stimulation field in three dimensions, and IMD 14 may deliver PNFS via a three dimensional electrode array (e.g. partial ring or segmented electrodes or paddle leads including electrodes on more than one surface), as described above. In addition, although user interfaces that present a two-dimensional environment for the user to provide different stimulation field characteristic inputs, such as a stimulation vector, stimulation focus, stimulation breadth, and stimulation depth input, in other examples, a computing device may present a three-dimensional environment that the user may interact with to provide the different stimulation field characteristics.

Figure 9A:
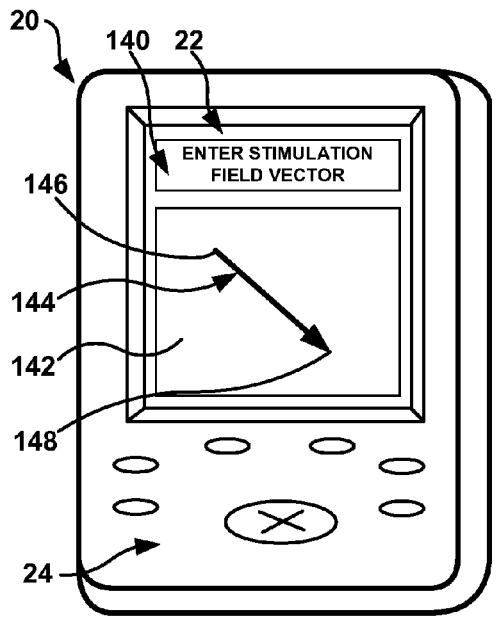
FIGS. 9A and 9B illustrate example user interfaces that may be displayed by a programmer for receiving a stimulation field vector input and an electrode configuration determined based on the stimulation field vector input.
Figure 9B:
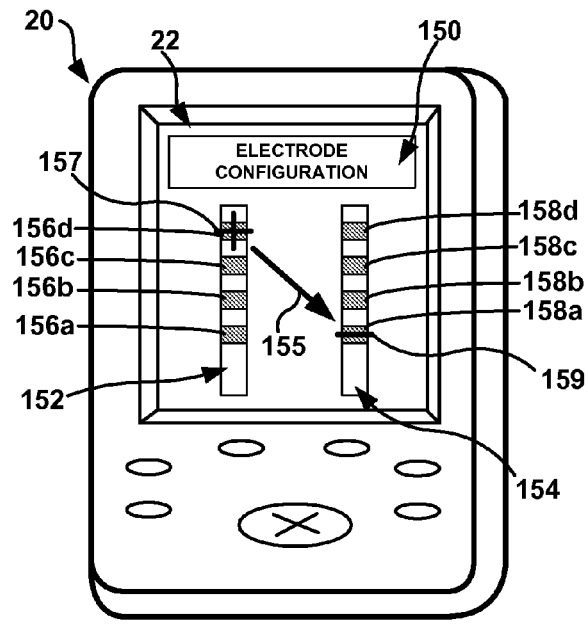

FIGS. 9A and 9B are conceptual illustrations of example user interface screens that may be presented by a processor of a computing device, such as patient programmer 18 or clinician programmer 20. The user interface screen shown in FIG. 9A may be used by a user to provide a stimulation field vector input, and the user interface screen shown in FIG. 9B presents an electrode configuration that is determined based on the stimulation field vector input. While the user interface screens in FIGS. 9A-13C are described with reference to processor 70, user interface 72, and display 22 of clinician programmer 20, in other examples, the user interface screens may be presented by other computing devices, such as processor 50 of patient programmer 18 may display similar user interface screens via user interface 52 and display 28 of patient programmer 18. In some examples, processor 70 of clinician programmer 20, processor 50 of patient programmer 18, or processor 32 of IMD 14 may receive the various inputs described below and may determine an electrode configuration based on the stimulation field vector input and any other received inputs.

As FIG. 9A illustrates, processor 70 may display a user interface screen 140 via display 22, where user interface screen 140 prompts the user to enter a stimulation field vector input 144. The user interface screens described herein may be, for example, graphical user interfaces presented by processor 70. In the example shown in FIG. 9A, display 22 may be a touch screen and may include a stimulation field vector input section 142 that accepts a stimulation field vector input 144 from the user, e.g., via a finger of the user interacting with display 22 or stylus or other pointing device.

In the example shown in FIG. 9A, stimulation field vector input 144 comprises one or more lines indicating the vector or a vector beginning point 146 and vector end point 148. In other examples, the user may provide stimulation field vector input 144 via keypad 24, e.g., by entering the coordinates of a stimulation field vector beginning point 146 and a stimulation field vector end point 148, or selecting stimulation field vector input 144 from a plurality of stored vector inputs that are presented to the user via display 22, or by rotating, using an appropriate control, a default or starting vector to a desired orientation. In either example, if the user only provides the stimulation field vector beginning point 146 and end point 148, processor 70 may connect the beginning point 146 and end point 148 and display the resulting stimulation field vector input 144.

Although a single vector input 144 is shown in example user interfaces described herein, e.g., with respect to FIGS. 9A-10B, in other examples, the user may input more than one stimulation field vector. In some examples, the two or more stimulation field vector inputs may share, for example, a starting point or an end point.

Processor 70 determines an electrode configuration based on the stimulation field vector input 144. In some examples, processor 70 may present the resulting electrode configuration via an electrode configuration screen 150 presented by display 22, as shown in FIG. 9B. In the example illustrated in FIG. 9B, an electrode array includes a first lead body 152 and a second lead body 154. First lead body 152 includes four electrodes 156a, 156b, 156c, 156d (collectively "electrodes 156") and second lead body 154 includes four electrodes 158a, 158b, 158c, 158d (collectively "electrodes 158"). In order to determine the electrode configuration that produces a stimulation field corresponding to stimulation field vector input 144, processor 70 may select electrode 156d as an anode electrode, as indicated by plus sign 157, and electrode 158a as a cathode electrode, as indicated by minus sign 159. The resulting stimulation field direction extends in the direction indicated by arrow 155, which is approximately the same as stimulation field vector input 144.

In some examples, the stimulation field direction may be limited by the electrode configurations that may be possible using the implanted lead and device. For example, in FIG. 9B, only a finite number of stimulation field orientations may be achieved using the four electrodes 156 and 158 coupled to first lead body 152 and second lead body 154. That is, the electrode configurations are limited to those including less than eight electrodes, and those including electrodes at the positions at which electrodes 156 and 158 are implanted. In some examples, a user may input the stimulation field vector (e.g., stimulation field vector 144, and processor 70 (or processor 32 or 50) may determine an electrode configuration which produces a stimulation field direction that approximates the orientation of the user-inputted vector 144.

In other examples, IMD 14 may provide unipolar stimulation, and an electrode array may include one or more electrodes coupled to a lead body, and a housing of IMD 14 or an electrode coupled to the housing. Processor 70 may determine an electrode configuration based on the stimulation field vector input provided by a user. For example, processor 70 may select an electrode coupled to the lead body as a cathode electrode and the housing of IMD 14 as an anode electrode. The stimulation field direction produced by the electrode configuration may be adjusted by configuring a different electrode coupled to the lead body as the cathode electrode.

In other examples, IMD 14 may provide stimulation via a three-dimensional electrode array, such as electrodes coupled to at least three leads, electrodes coupled to two surfaces of a housing of IMD 14, or the like. In examples such as these, the stimulation field vector may be defined in three dimensions, and processor 70 may determine an electrode configuration to produce a stimulation field direction corresponding to the orientation of the user-inputted vector.

Figure 10A:
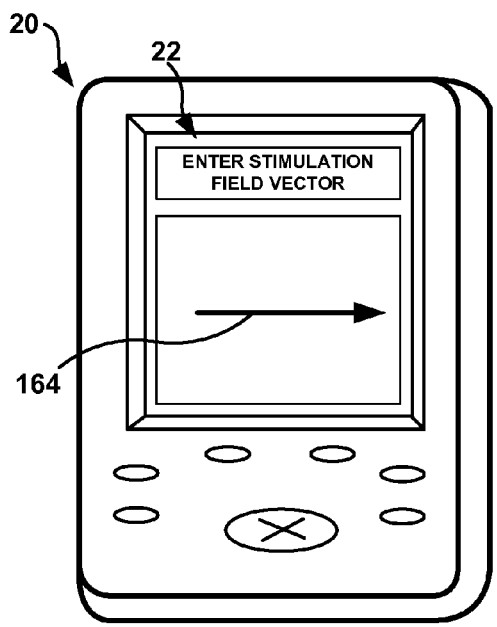
FIGS. 10A and 10B illustrate other example user interfaces that may be displayed by a programmer for receiving a stimulation field vector input and presenting an electrode configuration determined based on the stimulation field vector input.
Figure 10B:
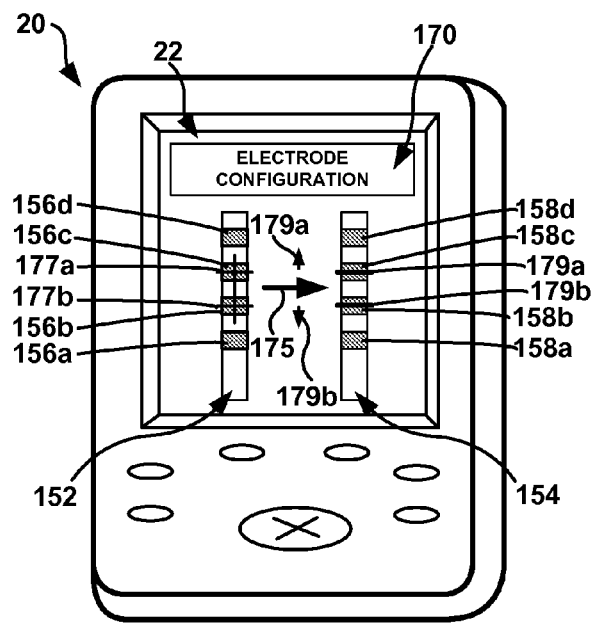

In the example illustrated in FIGS. 9A and 9B, a stimulation field corresponding to the stimulation field vector input 144 is produced using a first electrode 156d and a second electrode 158a, which comprise an anode electrode and a cathode electrode, respectively. However, in other examples, the stimulation field may be produced using more than two electrodes. For example, as shown in FIGS. 10A and 10B, a user may provide stimulation field vector input 164 and processor 70 may determine the electrode configuration corresponding to stimulation field vector input 164 by configuring two electrodes 156b, 156c coupled to first lead body 152 as anode electrodes, as indicated by plus signs 177a and 177b, and configuring two electrodes 158b, 158c coupled to second lead body 154 as cathode electrodes, as indicated by minus signs 179a and 179b. The resulting stimulation direction, indicated by arrow 175, extends in approximately the same direction as stimulation field vector input 164.

The example of user interface screen 170 shown in FIG. 10B also includes an up arrow 179a and a down arrow 179b, which the user may interact with in order to further adjust the electrode configuration to move the stimulation field substantially along a longitudinal axis of leads 152, 154. For example, display 22 may be a touch screen, and when the user presses a portion of display 22 corresponding to up arrow 179a, processor 70 may change the electrode configuration to shift the stimulation field along a longitudinal axis of lead bodies 152, 154 (e.g., toward electrodes 156d, 158d). For example, processor 70 may select electrodes 156d and 158d as active electrodes of the electrode configuration and deselect electrodes 156b, 158b, thereby effectively shifting the stimulation field up, in a direction away from electrodes 156a, 158a. In other examples, the user may select up arrow 179a by manipulating a cursor using a mouse, or by actuating an arrow key in keypad 24.

As another example, when a user presses a portion of display 22 corresponding to down arrow 179b or otherwise selects down arrow 179b, processor 70 may shift the stimulation field along the longitudinal axis of lead bodies 152, 154, e.g., toward electrodes 156a, 158a. For example, processor 70 may select electrodes 156a and 158a as active electrodes of the electrode configuration and deselect electrodes 156c, 158c, thereby effectively shifting the stimulation field down, in a direction away from electrodes 156d, 158d. In some examples, processor 70 may both add electrodes to the electrode configuration and remove electrodes from the electrode configuration to shift the stimulation field vertically up or down the electrode array. Additionally, in other examples, the electrode array may include a complex electrode array that enables the stimulation field to be shifted in other directions, such as laterally, or diagonally, or may be shifted in more than two opposing directions (e.g., vertically, laterally, and, in some cases, rotationally).

User interface screen 170 may also permit the user to rotate stimulation field vector input 175 within the user interface presented by programmer 20. The stimulation field vector input 175 may be rotated to, for example, adjust a third dimension of the inputted stimulation field vector.

As previously indicated, in some examples, a stimulation field vector input 144 (FIG. 9A), 164 (FIG. 10A) may also indicate a desired amplitude or a breadth of stimulation. User interface screens 140, 170 may be configured to enable the user to modify the magnitude of the stimulation vector inputs 144, 164 to indicate a desired amplitude for PNFS or a desired breadth (e.g., width of a stimulation field) for the PNFS. The relative size of the inputted stimulation vectors (e.g., the length or width) displayed within user interfaces 140, 170 may directly correlate to a relative amplitude or breadth of stimulation e.g., from a starting point. Processor 70 may present displays indicating the amplitude or other stimulation parameter values with which the inputted stimulation field vectors 144, 164 correspond to. The user may then adjust the magnitude of stimulation field vector inputs 144, 164 to adjust the amplitude or other stimulation parameter values that may affect breadth (e.g., frequency or pulse width).

For example, the user may increase the length of an inputted stimulation field vector 144 displayed within user interface 140 to increase the amplitude from a starting amplitude, which may be, e.g., about 0 volts to about 10 volts. Each incremental length change of the stimulation field vector may correspond to an incremental increase of the stimulation amplitude. As another example, the user may increase the width or the girth (in three dimensions) of the inputted stimulation field vector 144 in order to increase the breadth of a desired PNFS field from a starting point, e.g., a selected stimulation field size, which may be presented on a display of programmer 20. Each incremental width or girth change of the stimulation field vector may correspond to an incremental increase of the stimulation breadth.

In some examples, as described above, processor 70 may receive other inputs from the user which further define the stimulation field and influence the electrode configuration. For example, as shown in FIGS. 11A-11D, processor 70 may display user interface screens via user interface 72 (e.g., display 22) that allow a user to provide input indicating a stimulation breadth ("stimulation breadth input"), which corresponds to a linear dimension of the stimulation field generated by IMD 14 within the region of patient 11 in which patient perceives pain. The stimulation breadth may be measured along any suitable linear direction along the stimulation field. In some cases, the breadth of the stimulation field may generally reflect size of the stimulation field or the amount of tissue (e.g., a volume or cross-sectional area) within patient 11 that the stimulation field covers.

In the example shown in FIGS. 11A-11D, processor 70 presents user interface screen 180 that prompts a user to enter stimulation field vector input 184. Processor 70 may then display user interface screen 190 (FIG. 11B) that prompts a user to provide input to adjust a stimulation breadth, if desired. Processor 70 may interpret the stimulation breadth input as indicating a distance between the first electrode and the second electrode of a selected electrode combination. For example, a wide stimulation breadth may indicate a relatively large distance between at least one anode and at least one cathode of the electrode configuration selected based on stimulation field vector input 184, and a narrow stimulation breadth may indicate a relatively small distance between at least one anode and at least one cathode of the electrode configuration.

In the example illustrated in FIG. 11B, user interface screen 190 includes slider 192 that allows a user to adjust the stimulation breadth between a first end 194 indicating a relatively narrow stimulation breadth, and a second end 196 indicating a relatively wide stimulation breadth. In particular, the user may slide bar 198 between narrow stimulation breadth end 194 and wide stimulation breadth end 196. In some examples, slider 192 may include a finite number of predetermined positions at which bar 198 may be positioned, where each finite position may correspond to selection of electrode pairs within an electrode array. In other examples, the user may slide bar 198 substantially along any desired position along slider 192, and processor 70 may determine an electrode configuration that produces a stimulation breadth that is similar to the stimulation breadth indicated by the position of bar 198. Screen 190 may also include a cancel button 191, which the user may select when the user decides to not enter a stimulation breadth input, and an apply button 193, which the user may select to apply the stimulation breadth input.

While FIG. 11B illustrates adjusting the stimulation breadth using a slider 192 and bar 198, in other examples, different user interface elements may be used to adjust the stimulation breadth. For example, the user may select a stimulation breadth from a drop-down list, a list with check boxes, an array of icons representing different stimulation breadths, a bar graph, or another visual indication of the stimulation breadth, such as a pair of lines that move closer or further apart to represent the stimulation breadth. As previously indicated, stimulation breadth may also be adjusted using the size of the displayed stimulation vector input 184 (FIG. 11A). For example, the width (or girth) of the displayed stimulation vector input 184 may be a modifiable parameter, and the user may increase breadth by increasing the width of the displayed vector input 184 or decrease breadth by decreasing the width of the displayed vector input 184.

Figure 11C:
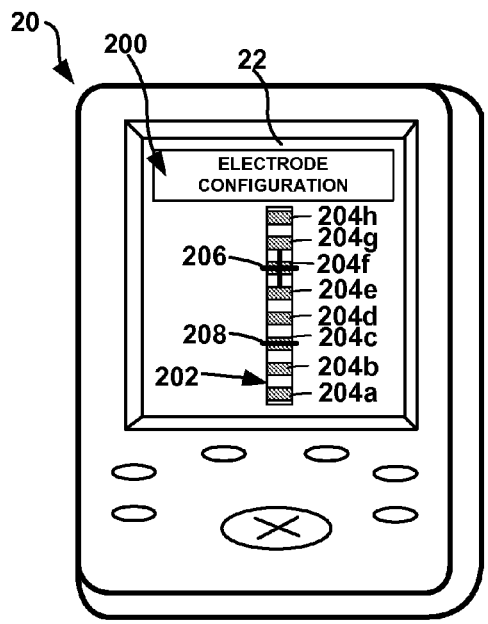

FIG. 11C illustrates an example user interface screen 200 presented on display 22 of clinician programmer 20, where screen 20 that displays an example electrode configuration determined by processor 70 based on the stimulation field vector input 184 and the stimulation breadth input provided by the user, as indicated by the position of bar 198 along slider 192. In the example of FIG. 11C, the electrode array includes a single lead body 202, which includes eight electrodes 204a-204h. Processor 70 has determined that selecting electrode 204f as a cathode electrode, indicated by plus sign 206, and electrode 204c as an anode electrode, indicated by minus sign 208, produces a stimulation field having both the stimulation direction indicated by stimulation field vector input 184 and the user-selected stimulation breadth indicated by the stimulation breadth input.

In other examples, IMD 14 may provide unipolar stimulation, and an electrode array may include at least one electrode coupled to a lead body and a housing of IMD 14 or an electrode coupled to the housing. Processor 70 may determine an electrode configuration based on the stimulation breadth input. For example, the unipolar electrode configuration may include an electrode coupled to the lead body configured as a cathode electrode. The stimulation breadth may be adjusted by selecting an electrode closer to or further from the housing of IMD 14 as the cathode electrode of the unipolar electrode configuration. Selecting the cathode electrode further from the IMD 14 housing may increase the stimulation breadth, whereas selecting the cathode electrode closer to the IMD 14 housing may decrease the stimulation breadth.

While not shown in FIG. 11C, in some examples, user interface screen 200 or another user interface screen may present options for the user to adjust the position of the electrodes along the lead body 202, as described with respect to FIGS. 10A and 10B. Further, in some examples, the electrode array may include electrodes coupled to a respective one of more than one lead, and may include greater or fewer than eight electrodes coupled to each lead. In examples such as these, processor 70 may determine an electrode configuration including a first electrode coupled to a first lead body and a second electrode coupled to a second lead body in response to receiving stimulation field vector input 184 and stimulation breadth input.

Figure 11D:
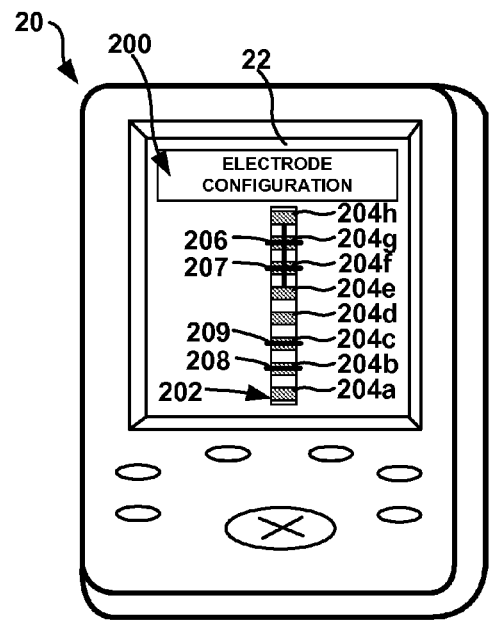

Additionally, as illustrated in FIG. 11D, the electrode configuration to produce the indicated stimulation breadth may include more than two electrodes selected from electrodes 204. For example, the electrode configuration may include four electrodes 204g, 204f, 204b, and 204c, which are configured as a first cathode 206, a second cathode 207, a first anode 208, and a second anode 209, respectively. In some examples, a first electrode pair comprising the first cathode 206 and first anode 208, and a second electrode pair comprising the second cathode 207 and second anode 209 may be configured to provide substantially simultaneous or interleaved stimulation pulses with different intensities. The use of more than one electrode pair or electrode subconfiguration within the selected electrode configuration may be useful for broadening a stimulation field.

For example, the first cathode 206 and first anode 208 may produce a stimulation pulse with about 10% of the total stimulation intensity, and the second cathode 207 and second anode 209 may substantially simultaneously produce a stimulation pulse with about 90% of the total stimulation intensity. This may result in a stimulation breadth that is incrementally wider than the stimulation breadth produced by the electrode configuration of FIG. 11C, but narrower than a stimulation breadth produced by an electrode configuration in which electrode 204g is configured as the only cathode electrode and electrode 204b is configured as the only anode electrode. Other stimulation percentages are also contemplated, as well as including more than two cathodes and/or more than two anodes over which the stimulation pulse intensity is distributed.

Figure 12A:
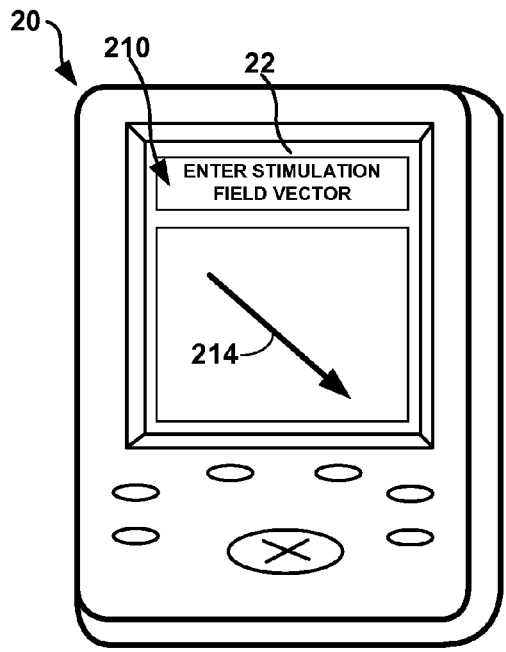
FIGS. 12A-12C illustrate example user interfaces that may be displayed by a programmer for receiving input indicating a stimulation field vector and a stimulation focus, and displaying an electrode configuration determined based on the input.
Figure 12B:
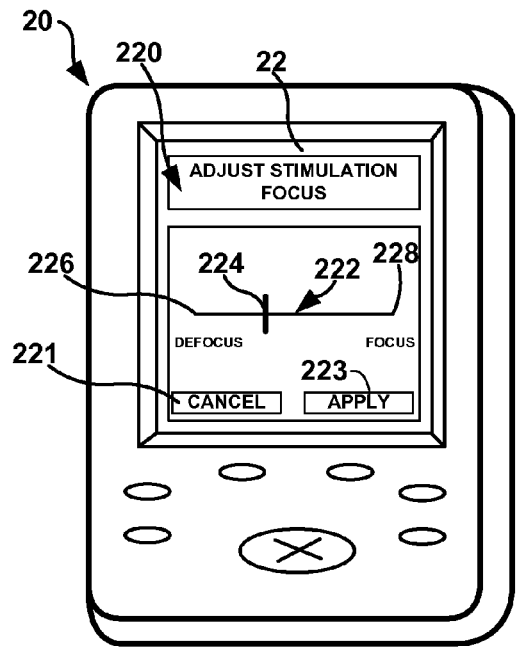
Figure 12C:
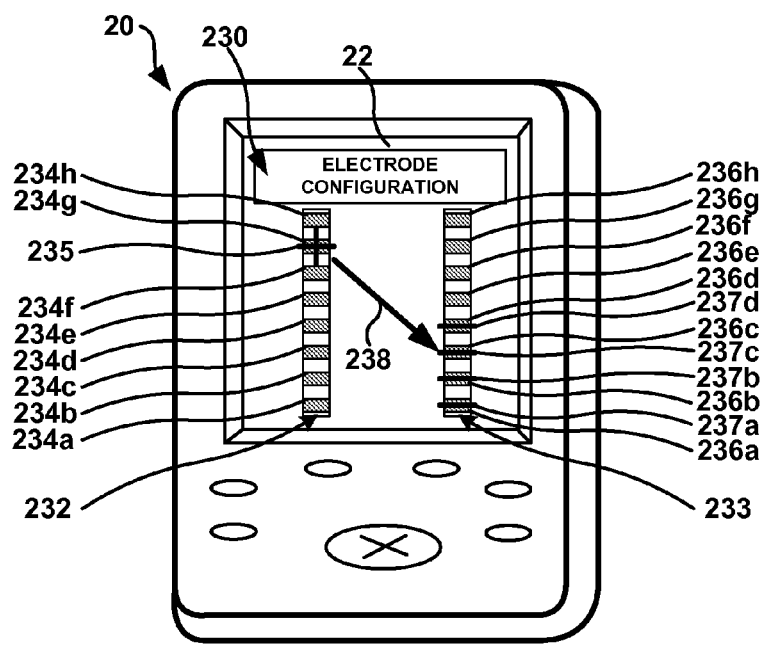

FIGS. 12A-12C illustrate example user interface screens presented by processor 70 that allow a user to provide input indicating a degree of a focus of a PNFS field generated by IMD 14 within patient. A degree of the focus of the PNFS field may range from a relatively focused field (a small focus) that may create a small, symmetrical field shape, to a relatively unfocused field (a larger stimulation focus) that may create a larger oblong or ovoid shape. In some cases, a PNFS field may be less focused than a stimulation field generated for spinal cord stimulation, which generally seeks to recruit small fibers within the spinal cord.

In some examples, the stimulation focus input may be provided in addition to the stimulation field vector input. For example, after receiving a stimulation field vector input 214 from a user, which may be inputted via user interface screen 210, which may be similar to user interface screen 170 of FIG. 9A, processor 70 may present user interface screen 220 (FIG. 12B) that prompts a user to provide input indicating a stimulation focus of the stimulation field indicated by the stimulation field vector input 214. The stimulation focus input may indicate a number of electrodes that are configured as cathode electrodes, a number of electrodes that are configured as anode electrodes, or both. In the illustrated example, processor 70 modifies the number of electrodes configured as cathodes in response to receiving stimulation focus input from the user.

As shown in FIG. 12B, user interface screen 220 may include slider 222, along which a bar 224 may be positioned to indicate the stimulation focus input. The bar 224 may be moved from a first end 226 of slider 222, which corresponds to a relatively defocused stimulation field, to a second end 228, which corresponds to a relatively focused stimulation field compared to the first end 226. In some examples, slider 222 may comprises a finite number of predetermined locations at which bar 224 may be positioned, and each location may correspond to a certain number of cathode electrodes. The predetermined locations and associated number of cathodes may be determined by, for example, the clinician or a manufacturer or distributor of programmer 20. In other examples, the user may select any position for bar 224 along slider 222, and processor 70 may determine an electrode configuration that produces a stimulation focus that corresponds to the stimulation focus input indicated by the position of bar 224. In the example shown in FIG. 12B, screen 220 may also include a cancel button 221, which the user may select when the user decides not to enter a stimulation focus input, and an apply button 223, which the user may select to apply the stimulation focus input to the electrode configuration.

While FIG. 12B illustrates adjusting the stimulation focus using a slider 222 and bar 224, in other examples, other user interface elements may be used to adjust the stimulation focus. For example, the user may select a stimulation focus input from a drop-down list, a list with check boxes, an array of icons representing different stimulation focus inputs, a bar graph, or another visual indication of the stimulation focus, such as a circle that changes size to represent the stimulation focus.

Processor 70 may determine an electrode configuration for producing a stimulation field direction, indicated by arrow 238 (FIG. 12C), based on the stimulation field vector input 214 and the stimulation focus input indicated by the position of bar 224 along slider 222. Processor 70 may display the determined electrode configuration on a user interface screen 230, as illustrated in FIG. 12C. In the example illustrated in FIG. 12C, the electrode array of available electrodes for determining the electrode combination includes a first lead body 232 and a second lead body 233, each of which include eight electrodes 234a-h and 236a-h, respectively. Processor 70 has determined that selecting electrode 234g as an anode electrode, indicated by plus sign 235, and electrodes 236a-d as cathode electrodes, indicated by minus signs 237a-d, produces a stimulation field having the field characteristics indicated by stimulation field vector input 214 and the stimulation focus input. In examples in which the user indicates a more focused stimulation field, processor 70 may determine an electrode configuration comprising fewer cathode electrodes, such as for example, including two cathode electrodes 236b and 236c. Conversely, in examples in which the user indicates a less focused stimulation field, processor 70 may determine an electrode configuration including more cathode electrodes, more anode electrodes, or both.

In other examples, IMD 14 may provide unipolar stimulation, and an electrode array may include at least one electrode coupled to a lead body and a housing of IMD 14 or an electrode coupled to the housing. Processor 70 may determine an electrode configuration based on the stimulation focus input, where the electrode configuration includes one or more electrode coupled to the lead body configured as a cathode electrode. The stimulation focus may be adjusted by selecting the number of cathode electrodes. For example, by selecting a greater number of electrodes on the lead body as cathode electrodes, the degree of stimulation focus may decrease. Selecting a fewer number of electrodes on the lead body as cathode electrodes may increase the stimulation focus.

Figure 13A:
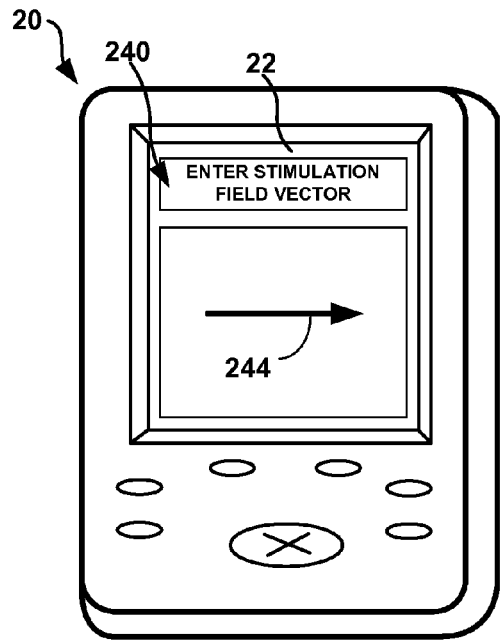
FIGS. 13A-13C illustrate example user interfaces that may be displayed by a programmer for receiving input indicating a stimulation field vector and a stimulation depth, and displaying an electrode configuration determined based on the input.
Figure 13B:
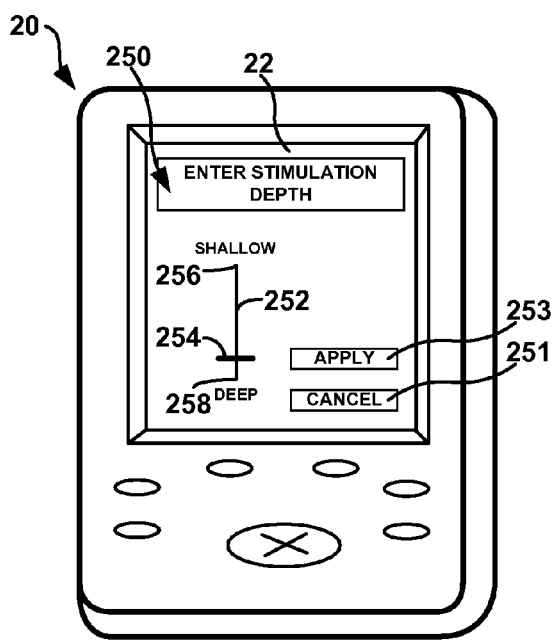
Figure 13C:
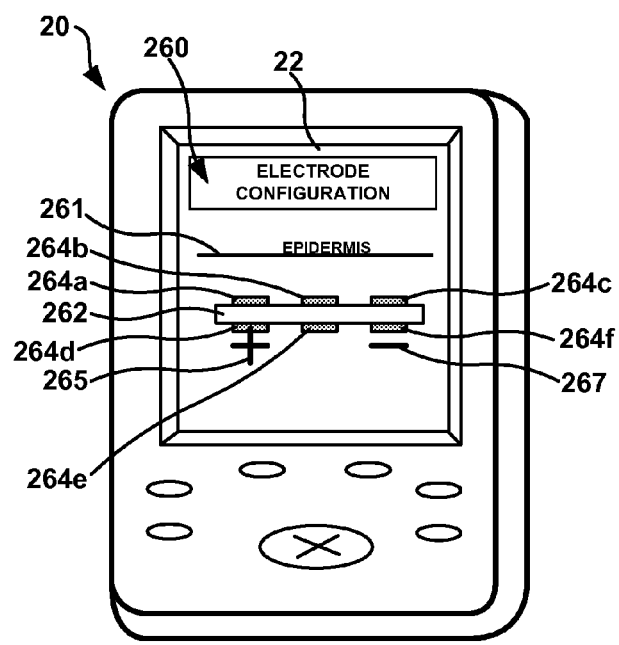

FIGS. 13A-13C illustrate example user interface screens that may be presented by processor 70 that allow a user, such as a clinician, to enter a stimulation depth input in addition to a stimulation field vector input. As shown in FIG. 13A, processor 70 may present user interface screen 240 to prompt the user to enter a stimulation field vector input 244. Once processor 70 receives stimulation field vector input 244, processor 70 may display user interface screen 250 that prompts a user to indicate a desired depth of the stimulation field within patient 11 relative to a reference point. For example, the stimulation depth may indicate a depth below the surface of an epidermis of patient 11 in the region in which IMD 14 delivers electrical stimulation.

In the illustrated example, user interface screen 250 includes a slider 252, along which a bar 254 may be positioned to indicate a desired depth of a stimulation field for PNFS relative to a reference point of patient 11, such as an outer surface of the epidermis of patient 11. A user may interact with user interface 72 (FIG. 4) to position bar 254 along slider 252, where a first end 256 of slider 252 indicates a shallow stimulation depth relative to the reference point of patient 11 (e.g., an epidermis) and a second end 258 of slider 252 indicates a deep stimulation depth relative to the reference point of patient 11. In some examples, bar 254 may be positioned at a finite number of predetermined locations along slider 252, and each location may indicate a depth of a PNFS field. In other examples, the user may position bar 254 at any location along slider 252, and processor 70 may determine an electrode configuration that produces stimulation field having a stimulation depth based on the position of bar 254 along slider 252. In the example shown in FIG. 13B, screen 250 includes a cancel button 251, which the user may select when the user decides not to enter a stimulation depth, and an apply button 253, which the user may select to apply the stimulation depth input.

While FIG. 13B illustrates adjusting the stimulation depth using a slider 252 and bar 254, in other examples, other user interface elements may be used to adjust the stimulation depth. For example, the user may select a stimulation depth from a drop-down list, a list with check boxes, an array of icons representing different stimulation depths, a bar graph, or another visual indication of the stimulation depth. As another examples, processor may present a medical image of patient 11 via user interface screen 240, 250, which enables the user to visualize the direction of stimulation indicated by stimulation field vector input 244 relative to one or more anatomical landmarks, tissue variations, or nerves. In addition, the medical image may also be useful to guide the user in selecting the depth of stimulation relative to an actual image of the patient's anatomical structure within region 12 for the delivery of PNFS. This may provide a more robust stimulation depth adjustment user interface. As previously indicated, examples of medical images that may be presented via a display of programmer 20 include, but are not limited to, fluoroscopic images, x-ray images, CT images, MRI, and DTI.

Once processor 70 receives the stimulation field vector input 244 and the stimulation depth input as indicated by the position of bar 254 along slider 252, processor 70 may determine an electrode configuration based on the stimulation field vector input 244 and the stimulation depth input, and display the determined electrode configuration, as shown in user interface screen 260 of FIG. 13C. In the illustrated example, the electrode array includes a three dimensional array of six electrodes 264a-264f coupled to a housing of IMD 262, which is implanted in the region in which patient 11 experiences pain. In other examples, the electrode array may include a three-dimensional electrode arrangement coupled to one or more lead bodies or housing of IMD 14. Electrodes 264a, 264b, and 264c are coupled on a surface of IMD 262 which is located more proximate to the surface of the epidermis of patient 11, indicated by line 261, and electrodes 264d, 264e, and 264f are coupled to an opposite surface of the IMD housing, which is further from the surface of the epidermis of patient 11. In the example shown in FIG. 13C, processor 70 has determined that selecting electrode 264d as an anode electrode, indicated by plus sign 265, and electrode 264f as a cathode electrode, indicated by minus sign 267, may be used to generate the stimulation field having the characteristics indicated by stimulation field vector input 244 and the stimulation depth input.

In other examples, IMD 14 may provide unipolar stimulation, and an electrode array may include one or more electrode coupled to a lead body and a housing of IMD 14 or an electrode coupled to the housing. Processor 70 may determine an electrode configuration based on the stimulation depth input, where the electrode configuration includes a cathode electrode coupled to the lead body. The stimulation depth may be adjusted by selecting different electrodes of the lead body as a cathode electrode. In some cases, selecting a different electrode of the lead body as a cathode electrode may effectively rotate the direction of PNFS stimulation within the stimulation field.

While the above examples have described processor 70 receiving a stimulation vector input and input specifying another characteristic of a stimulation field for delivery of PNFS, such as a movement of the electrode configuration, a stimulation breadth input, a stimulation focus input, and a stimulation depth input, in other examples, processor 70 may prompt a user to enter more than one stimulation field characteristic input in addition to the stimulation vector input. For example, processor 70 may prompt a user to enter a stimulation field vector input, a stimulation breadth input, and a stimulation focus input, and may determine an electrode configuration based on all three inputs. In other examples, processor 70 may prompt a user to enter a stimulation field vector input, a stimulation breadth input, and a stimulation depth input, and may determine an electrode configuration based on all three inputs. In other examples, processor 70 may prompt a user to enter a stimulation field vector input, a stimulation focus input, and a stimulation depth input, and may determine an electrode configuration based on all three inputs. In yet other examples, processor 70 may prompt a user to enter a stimulation field vector input, a stimulation focus input, a stimulation focus input, and a stimulation depth input, and may determine an electrode configuration based on all four inputs.

As described above, in some examples, the PNFS programming techniques may also include selecting at least one region from a plurality of regions in which patient 11 experiences pain and entering a therapy input defining an aspect of PNFS for the at least one region. Each of the plurality of regions may include at least two electrodes implanted therein for delivering PNFS to the region. In some examples, each region may include an electrode array, which may include at least two electrodes coupled to at least one lead or medical device housing. For example, an electrode array may include at least one electrode coupled to each of at least two lead bodies, or may include at least two electrodes coupled to a common lead body, as described above.

Figure 14:
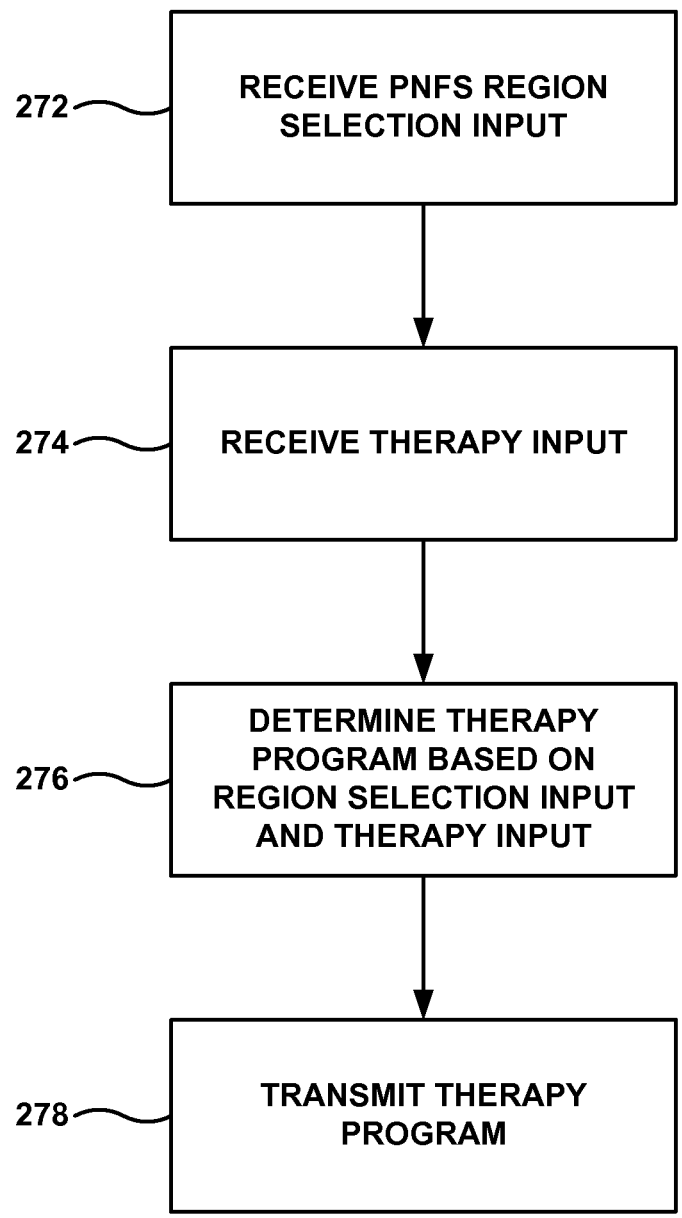
FIG. 14 is a flow diagram illustrating an example technique for programming a medical device to deliver PNFS to a region in which a patient experiences pain.
Figure 15:
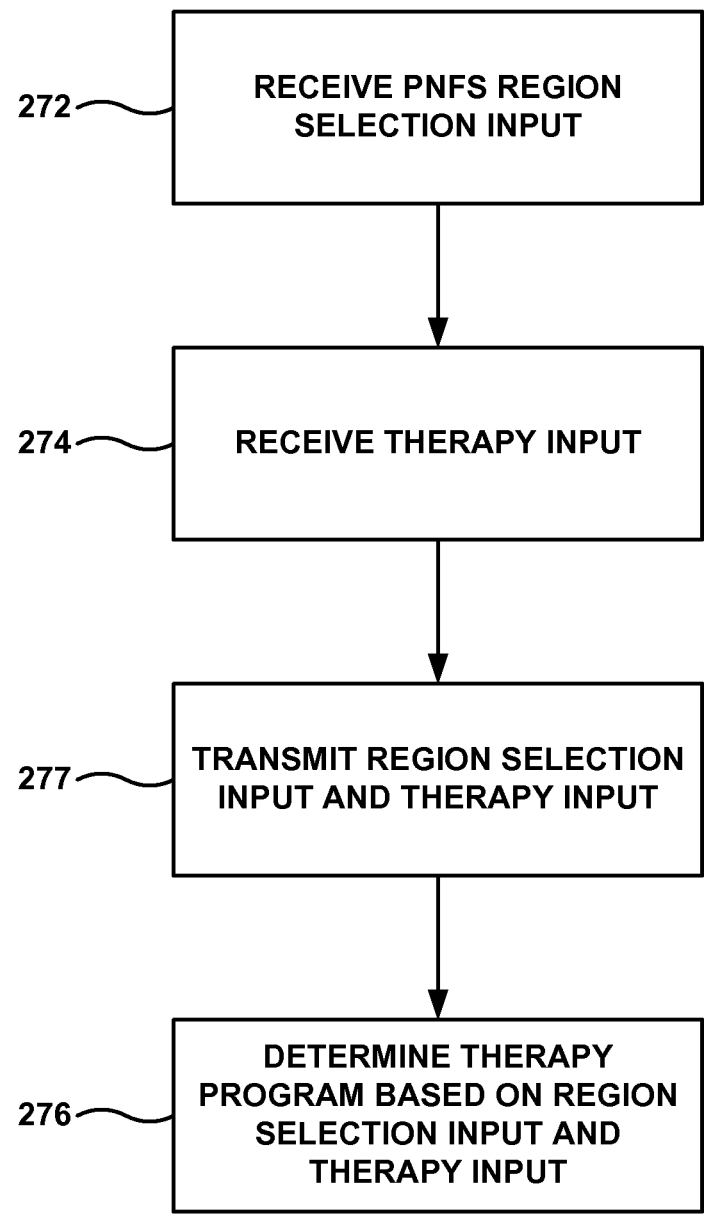
FIG. 15 is a flow diagram illustrating another example technique for programming a medical device to deliver PNFS to a region in which a patient experiences pain.

FIG. 14 is a flow diagram illustrating an example technique for delivering PNFS to at least one region in a body of a patient in which the patient experiences pain, where the region is selected by a user, which may be, e.g., patient 11 or a clinician. While the techniques shown in FIGS. 14 and 15 are described with reference to processor 70 and user interface 72 of clinician programmer 20, in other examples, another device may be used to receive the input selecting a therapy region and input specifying an aspect of the therapy delivery. For example, in some cases, processor 50 and user interface 52 of patient programmer 18 may receive the described inputs. In some examples, processor 70 of clinician programmer 20, processor 50 of patient programmer 18, or processor 32 of IMD 14 may receive the various therapy inputs described below and may determine a PNFS program based on the therapy input.

Processor 70 may receive a region selection input selecting at least one region from a plurality of regions of a body of patient 11 in which patient 11 experiences pain (272). At least two electrodes may be implanted within each of the regions available for selection by patient 11. The plurality of regions may include, for example, various regions of the back, the back of the head, the neck or shoulders, above the eyebrow, and either over the eye or under the eye, or a limb, and PNFS may be delivered to treat failed back surgery syndrome (FBSS), cervical pain (shoulder and neck pain), facial pain, headaches, supra-orbital pain, inguinal and pelvic pain, chest and intercostal pain, mixed pain (nociceptive and neuropathic), visceral pain, neuralgia, peroneal pain, phantom limb pain, and arthritis.

In some examples, processor 70 may present (via user interface 72) a predetermined list of regions for selection by patient 11. The available regions for delivery of PNFS that patient 11 (or another user) may select from may be presented as a list of regions (e.g., presented via text or symptoms), and the user may select the desired therapy regions from the list. In other examples, processor 70 may present a representation of a body of patient 11 (which may be a generic representation), and the user may select the regions of the body in which patient 11 feels pain. The preselected regions presented in the list may be selected based on an image of patient 11 showing the actual implanted electrodes (e.g., the actual lead 16 location within patient 11).

Processor 70 may also receive a therapy input defining an aspect of PNFS for the selected region(s) (274). For example, the therapy input may comprise enabling or disabling PNFS for the selected region(s), adjusting a relative intensity of PNFS for at least two selected regions, adjusting a balance of PNFS between at least two regions, indicating a desired shift of PNFS from a first region to a second region, or adjusting an extent to which a first stimulation field produced by delivering PNFS to a first region overlaps a second stimulation field produced by delivering PNFS to a second region. Each of these therapy inputs are described in further detail below. Other therapy inputs defining other aspects of PNFS are contemplated.

After receiving therapy input (274), processor 70 determines a therapy program that defines the therapy parameter values for the PNFS delivered to the selected region(s) based on the therapy input and the region selection input (276). In examples in which IMD 14 delivers electrical stimulation pulses, the therapy program includes respective values for stimulation parameters such as a voltage or current pulse amplitude, pulse width, a pulse rate, and an electrode configuration, according to which IMD 14 delivers PNFS to the region. Each of the above-listed therapy inputs may indicate a change in at least one of the therapy parameter values, as described in further detail below. In some examples determining a therapy program may comprise selecting a therapy program from a list of therapy programs stored in memory 74 of programmer 20 based on the therapy input, while in other examples, processor 70 may generate a therapy program based on the therapy input.

After determining the therapy program (276) based on the region selection input and the therapy input, processor 70 may transmit the determined therapy program (278) to IMD 14 via the respective telemetry modules 80, 36. In some examples, processor 70 transmits the therapy parameter values of the therapy program. In other examples, IMD 14 stores a list of therapy programs that are associated with indicators, such as alphanumeric or symbolic indicators. Accordingly, in some examples, processor 70 transmits the therapy program to IMD 14 by transmitting the indication of the selected therapy program, and processor 32 of IMD 14 may select the corresponding therapy program from the memory 41 of IMD 14. Processor 32 of IMD 14 may receive the therapy program and may control stimulation generator 38 to provide PNFS according to the therapy program. In some embodiments, processor 70 may also present the therapy parameter values for the determined therapy program via display 22.

In other examples, as illustrated in FIG. 15 processor 70 receives the region selection input (272) via user interface 72, receives the therapy input (274) via user interface 72 (or user interface 52), and then transmits the region selection input and the therapy input (277), e.g., to of IMD 14 via respective telemetry modules 80, 36. Processor 32 of IMD 14 may receive the region selection input and the therapy input from processor 70 of clinician programmer 20 and determine a therapy program for providing PNFS to the at least one region indicated by the region selection input based on the therapy input (276). In some examples, processor 32 of IMD 14 determines a therapy program by selecting a therapy program from a list of therapy programs stored in memory 41 of IMD 14 (FIG. 2) based on the therapy input, while in other examples, processor 32 generates a new therapy program based on the therapy input. In some embodiments, processor 32 transmits the determined therapy program to processor 70 of clinician programmer 20 via the respective telemetry modules 36, 80. Processor 70 may store the therapy program for later evaluation by a clinician, and, in some cases, processor 70 may display values of the therapy parameters for the determined therapy program via display 22.

FIGS. 16A-16G are conceptual illustrations of example user interface screens that may prompt a user, such as a clinician or patient, to enter a region selection input and a therapy input. The user interface screens illustrated in FIGS. 16A-16G may be graphical user interfaces presented by processor 70 of clinician programmer 20 via user interface 72, or by a processor of another device. Accordingly, while the user interface screens in FIGS. 16A-16G are described with reference to processor 70, user interface 72, and display 22 of clinician programmer 20, in other examples, processor 50 of patient programmer 18 may display the user interface screens via user interface 52 and display 28 of patient programmer 18. In some examples, processor 70 of clinician programmer 20, processor 50 of patient programmer 18, or processor 32 of IMD 14 may receive the various therapy inputs described below and may determine a therapy program based on the therapy inputs(s).

In some examples, display 22 includes a touch screen display, and the user may interact with display 22 to provide the region selection input and the therapy input. In some examples, the user may use a stylus or another pointing device to interact with the touch screen. In other examples, the user may interact with keypad 24, a mouse, or another equivalent input device to enter the region selection input and the therapy input, and processor 70 may update display 22 accordingly.

Figure 16A:
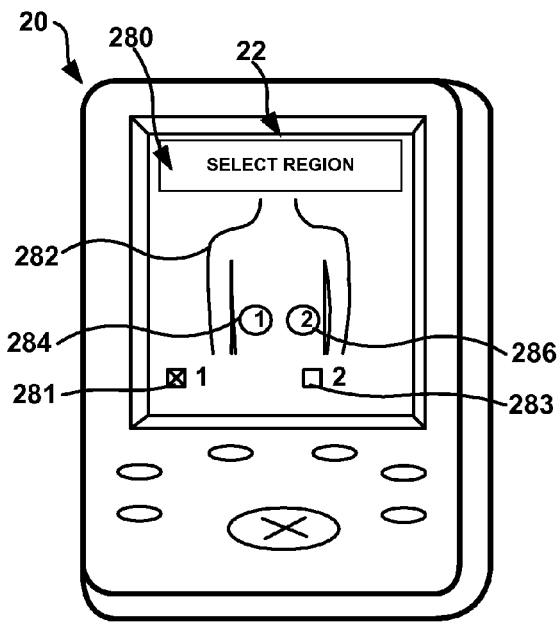
FIGS. 16A-16G illustrate example user interfaces that may be displayed by a programmer for receiving a therapy region selection input and a therapy input.

FIG. 16A illustrates an example user interface screen 280 presented by processor 70 of clinician programmer 20 via display 22, whereby screen 280 provides an interface that allows a user to enter a region selection input. Region selection user interface screen 280 includes a representation of a body 282 of patient 11, with a first region 284 (region "1" in FIG. 16A) and a second region 286 (region "2" in FIG. 16A) overlying the body 282. In some examples, the representation of body 282 is general and may not be specific to patient 11. In other examples, the representation of body 282 is specific to patient 11 and may, for example, include medical images of region 12 of patient to which PNFS is delivered. As previously indicated, the medical images may include, for example, x-ray images, fluoroscopic images, CT images, MRI, and DTI.

First region 284 and second region 286 indicate regions of the patient's body in which patient 11 experiences pain and regions to which IMD 14 may deliver PNFS via an electrode or electrode array. Accordingly, in some examples, at least two electrodes are implanted within the regions of the patient's body corresponding to regions 284, 286 shown in FIG. 16A. In the illustrated example, first region 284 and second region 286 comprise regions in a left lower back and right lower back of patient 11, respectively. As described above, in other examples, other regions may include other regions of the back, the back of the head, above the eyebrow, and either over the eye or under the eye, a limb, and the like. Additionally, some examples may include more than two therapy regions.

Region selection user interface screen 280 may also include a first check box 281 that corresponds to first region 284 and a second check box 283 that corresponds to second region 286. A user selects at least one of the first region 284 and second region 286 by selecting the respective checkbox 281, 283, e.g., using a stylus to press the checkbox 281 or 283, or draw an "X" in the checkbox 281 or 283. In other examples, screen 280 may not include check boxes 281 and 283, and may instead include buttons, a drop-down list, a radio button, or the like, which allow the user to select at least one of first region 284 and second region 286. A radio button may include, for example, a graphical user interface element that allows a user to select from a predefined set of options. In some examples, the user may directly select the region "1" or region "2" indications in order to select the region for PNFS delivery, and processor 70 may highlight the region or otherwise distinguish the selected region(s) from the other available regions for selection.

Figure 16B:
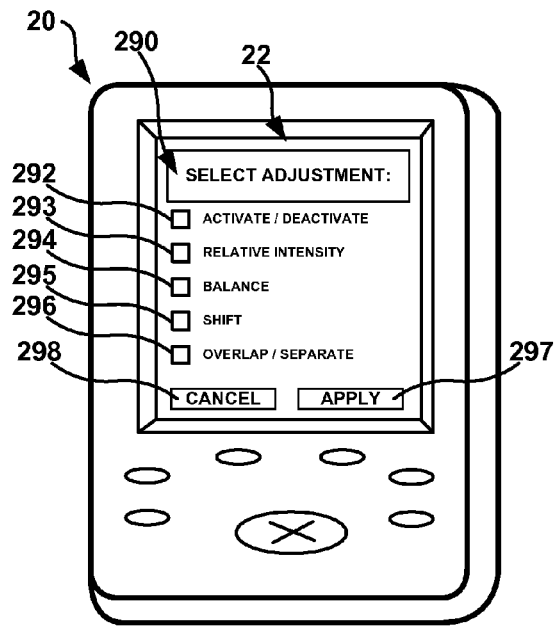

As shown in FIG. 16B, after the user has selected one or more regions 284, 286 for PNFS delivery, processor 70 may display a therapy adjustment user interface screen 290, which prompts the user to enter at least one type of therapy adjustment for the selected region(s). The therapy adjustment user interface screen 290 may present a list of therapy adjustment actions via any suitable technique. In the example shown in FIG. 16B, screen 290 includes a textual list of therapy adjustment actions, and the user may select the checkbox 292-296 corresponding to the desired action. For example, selecting checkbox 292 may change the status of PNFS at the selected region(s), such as activating or deactivating PNFS to the selected region(s). Selecting checkbox 293 may indicate that the user wishes to adjust a relative intensity of PNFS between a selected region and at least one other region, while selecting checkbox 294 may indicate that the user wishes to adjust the balance of PNFS between a selected region and at least one other region. Selecting checkbox 295 may indicate that the user wishes to shift PNFS from a selected region to another region, and selecting checkbox 296 may indicate that the user wishes to adjust the extent to which a first stimulation field produced by delivering PNFS in a selected region overlaps a second stimulation field produced by delivering PNFS in a second region.

In other examples, user interface screen 290 may include buttons, a drop-down list, radio buttons, or the like, which allow the user to select at least one type of therapy adjustment. Once the user selects those adjustments which the user wishes to make, the user may select the apply button 297, and, if applicable, processor 70 may display at least one user interface screen that prompts the user to provide more information to make the desired adjustment(s). If the user decides not to make any adjustments to the delivery of PNFS to the selected regions, the user may select cancel button 298.

In some examples, the user may select more than one therapy adjustment and processor 70 may present user interface screens to allow the user to enter therapy inputs serially for each selected therapy adjustment. For example, the user may select checkbox 293, indicating a relative intensity therapy adjustment and checkbox 296, indicating an overlap/separate therapy adjustment, and processor 70 may present user interface screen 300 (FIG. 16C) followed by user interface screen 340 (FIG. 16D) to allow the user to adjust both the relative intensity and extent to which a first stimulation field produced by delivering PNFS to a first region overlaps a second stimulation field produced by delivering PNFS to a second region.

Processor 70 may prohibit the user from selecting two or more of the therapy adjustment actions that are not compatible, such as deactivating therapy (checkbox 292) and increasing a relative intensity of PNFS (checkbox 294). In some examples, if the user attempts to select to therapy adjustment actions that are inconsistent, processor 70 generates a notification to the user that the combination of therapy adjustment actions is not permitted. In other examples, upon selecting a therapy adjustment action, processor 70 removes the inconsistent therapy adjustment actions as selectable options, such as by graying out the inconsistent therapy adjustment actions or otherwise visually indicating the action is unavailable.

Certain types of therapy adjustments may require the user to select a first therapy region and a second therapy region, or at least two therapy regions. For example, in order for the user to adjust a relative intensity of PNFS, the user must select at least two therapy regions. Accordingly, in some examples, when the user selects a single region (e.g., first region 284) on screen 280 and selects an adjustment on screen 290 which requires the selection of more than one region, processor 70 may display screen 280 and prompt the user to select at least one other region (e.g., second region 286).

Figure 16C:
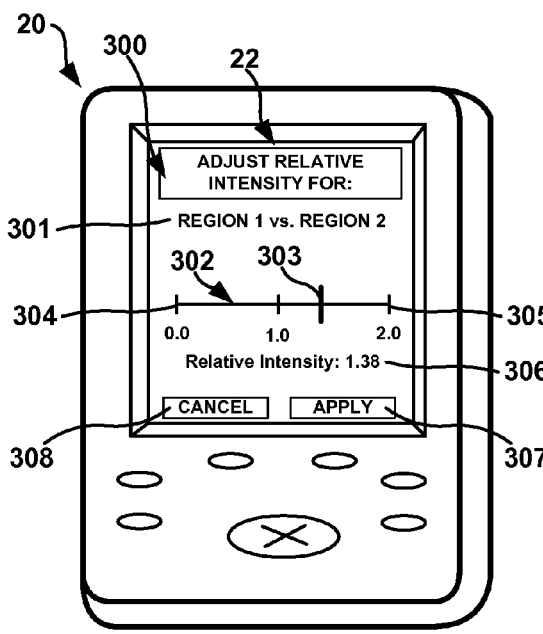

FIG. 16C illustrates an example user interface screen 300 that may be presented to a user by processor 70 via display 22. Upon selecting checkbox 293 of user interface screen 290 (FIG. 16B), processor 70 may present user interface screen 300, which provides an interface for receiving a therapy input adjusting the relative intensity of PNFS between first therapy region 284 (region 1) and second therapy region 286 (region 2), as indicated by text 301. Intensity of stimulation may be a function of, for example, any one or more of the voltage or current amplitude value of the stimulation signal, frequency of stimulation signals, signal duration (e.g., pulse width in the case of stimulation pulses), signal burst pattern, and the like. The intensity of stimulation may, for example, affect the volume of tissue that is activated by the PNFS. Thus, the user may increase the voltage amplitude causing a larger volume of nervous tissue within a pain region to be activated.

In the illustrated example, screen 300 comprises a slider 302 along with a bar 303 that may be positioned along slider 302 to indicate the relative intensity of stimulation between the first and second regions 284, 286. Slider 302 allows a user to input a single command to adjust the relative intensity of stimulation between the first and second regions 284, 286, instead of requiring the user to independently adjust the intensity of stimulation delivered to first region 284 and second region 286 to effectively adjust a relative intensity of stimulation. Slider 302 extends between a first end 304 and a second end 305. First end 304 indicates a relative intensity of 0.0, or that PNFS is not delivered to first therapy region 284. Second end 305 indicates a relative intensity of 2.0, or that PNFS delivered to first therapy region 284 is approximately twice as intense as PNFS delivered to second therapy region 286. In other examples, first end 304 and second end 305 may indicate different relative intensities, such as 0.5 and 5.0, respectively, or other appropriate values. In the illustrated example, screen 300 also includes a numerical indication 306 of the relative intensity indicated by the position of bar 303 along slider 302. In some examples, the user may directly enter a numerical value for the relative intensity and the position of bar 303 along slider 302 will adjust accordingly. Numerical indication 306 may be, for example, a ratio of the stimulation intensity between first region 284 and second region 286.

In other examples, screen 300 may not include a slider 302 and bar 303 and may instead include other user interface elements with which the user may select a relative intensity of PNFS for at least two regions. For example, screen 300 may comprise checkboxes, radio buttons, a drop-down list, icons, a text entry field, or the like, which allow the user to select or adjust the relative intensity of PNFS for at least two regions.

In the example shown in FIG. 16C, screen 300 further includes a cancel button 308, which the user may select when the user decides to not adjust the relative intensity of PNFS, and an apply button 307, which the user may select to apply the relative intensity adjustment to the PNFS therapy.

IMD 14 may deliver PNFS to region 284 and second region 286 according to different therapy programs. Adjusting the relative intensity of PNFS between the at least two selected regions may comprise adjusting therapy parameter values of at least one of the therapy programs defining the PNFS to first and second regions 284, 286. For example, upon receiving input from the user increasing the intensity of PNFS delivered to first region 284 relative to second region 286, processor 70 may increase the voltage or current pulse amplitude value of the therapy program defining PNFS delivered to the region 284, or may decrease the voltage or current pulse amplitude value of the therapy program defining PNFS delivered to second region 286. In other examples, processor 70 may adjust the relative intensity of PNFS to first region 284 by adjusting a pulse width value or pulse rate value of the therapy program defining PNFS delivered to the region 284, or adjusting a pulse width value or pulse rate value of the therapy program defining PNFS delivered to second region 286.

Figure 16D:
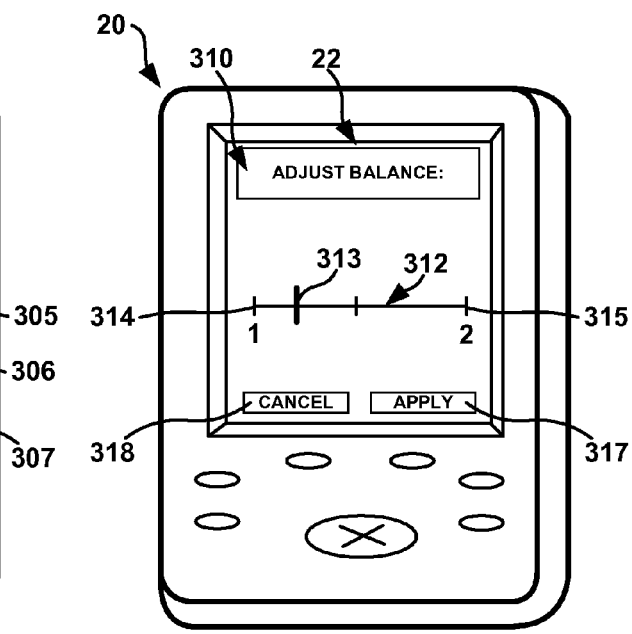

FIG. 16D illustrates a user interface screen 310 that provides an interface with which a user may provide a therapy input indicating a balance of PNFS stimulation between at least two selected regions. While first region 284 and second region 286 are referred to in the description of FIG. 16D, in other examples, user interface screen 310 may be used to provide therapy input indicating a balance of PNFS between other selected regions, which may include two or more selected regions. In some examples, user interface screen 310 may be presented by processor 70 via display 22 of clinician programmer 20.

Screen 310 includes a slider 312 extending from a first end 314 and a second end 315. A bar 313 may be positioned along slider 312 to indicate the balance of stimulation desired by the user. Slider 312 allows a user to input a single command to adjust the balance of stimulation between the first and second regions 284, 286 instead of requiring the user to independently adjust the intensity or duration of stimulation delivered to first region 284 and second region 286 to effectively adjust a balance of stimulation. Positioning bar 313 at first end 314 of slider 312 may indicate PNFS is delivered first region 284 and no stimulation is delivered to second region 286. Positioning bar 313 at second end 315 of slider 312 may indicate PNFS is delivered to second region 286 and not to first region 284. In some examples, screen 310 may prohibit the user from balancing the delivery of PNFS such that PNFS is delivered to one region 284 or 286 and not to the other selected region, such that a minimal amount of PNFS is delivered to all selected regions.

In the illustrated example, the position of bar 313 indicates the balance of PNFS that is biased towards region 1 (region 284), such that a greater amount of PNFS is delivered to region 1 than to region 2 (region 286). In some examples, the amount of PNFS delivered to a region may be a PNFS intensity, or a time period over which PNFS is delivered. Adjusting a balance of PNFS delivered to at least two regions, then, may comprise adjusting a balance of the intensity with which PNFS is delivered to each of the at least two regions or adjusting a balance of the amount of time that PNFS is delivered to each of the at least two regions, which may also affect the intensity.

In some examples, the total intensity of PNFS delivered to the at least two selected regions may be maintained at an approximately constant value as the balance of PNFS between the at least two selected regions is adjusted, such that patient 11 receives a constant intensity of PNFS, regardless of whether the PNFS is delivered to one region, two regions or more. In other examples, adjusting the balance of PNFS may increase the amount of PNFS delivered to at least one region, may decrease the amount of PNFS delivered to at least one region, or both, while not maintaining an approximately constant total delivered intensity level.

Figure 16E:
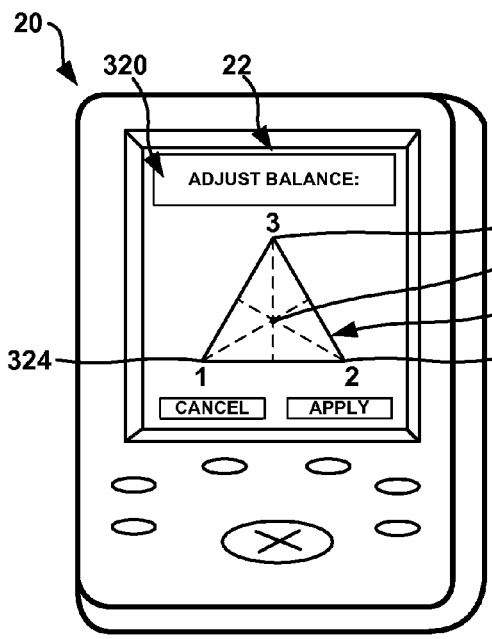

In some examples, the user may select more than two regions in which pain is felt and to which PNFS may be delivered, and processor 70 may present a user interface screen that includes user interface elements that allow the user to balance the stimulation between the more than two regions. For example, as shown in FIG. 16E, processor 70 may present user interface screen 320 via display 22, which may include a triangular element 322 where a first vertex 324 corresponds to a first region, a second vertex 325 corresponds to a second region, and a third vertex 326 corresponds to a third region. Screen 320 also includes a pointer 323 that the user may manipulate to indicate the balance of PNFS between the first, second, and third regions. In the example of FIG. 16E, pointer 323 is located equidistant from first vertex 324, second vertex 325, and third vertex 326, which may indicate a relatively balanced delivery of PNFS between the first, second, and third regions. The user may move pointer 323 along the lines within triangular element 322 in order to shift the balance of stimulation intensity between the three regions (indicated by "1," "2," and "3" in screen 320). For example, the user may move pointer 323 toward Region 3 in order to increase the intensity of stimulation delivered to Region 3 relative to Regions 1 and 2.

In examples in which more than three regions are selected, processor 70 may display other screens including user interface elements that allow a user to balance PNFS between the more than three regions. In other examples, screen 320 may include icons, drop-down lists, checkboxes, buttons, or the like, which allow the user to input the balance of PNFS between the two or more selected target regions within patient 11 for delivery of PNFS.

Additionally, in some examples, a plurality of regions in which patient 11 experiences pain may be divided into two or more region groups, where each region group includes one or more regions. For example, the plurality of regions may be divided into a "left back" group and a "right back" group. PNFS therapy may then be balanced between the two groups instead of the individual regions or a relative intensity of PNFS therapy between the two groups may be adjusted. Other region groups may include, for example, an "upper back" group, a "lower back" group, or other groups according to locations within the body of patient 11.

Figure 16F:
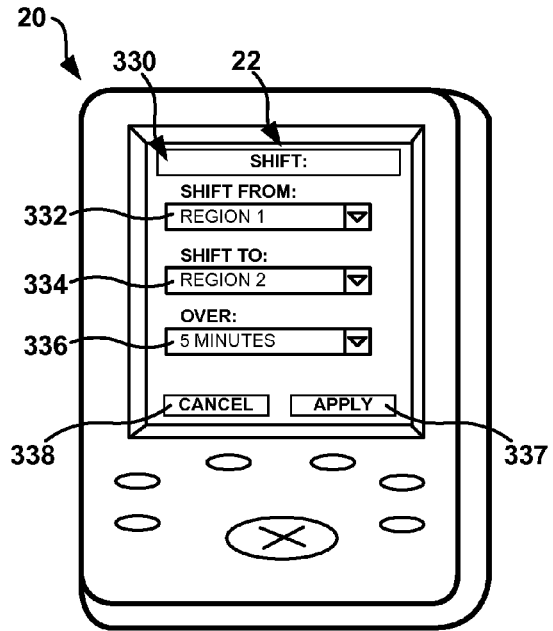

FIG. 16F illustrates an example user interface screen 330 that provides an interface for receiving therapy input from a user that indicates a desired shift of PNFS from a first region to a second region. In some examples, processor 70 of clinician programmer 20 may present user interface screen 330 via display 22. A user may interact with user interface screen 330 in order to shift PNFS from a first region to a second region, such that minimal or no PNFS is delivered to the first region upon the shift of PNFS. In some examples, PNFS may also be delivered to a third region, whereby PNFS delivery to the third region is relatively unaffected by the therapy input indicating the shift in PNFS.

User interface screen 330 includes a first drop-down list 332, which allows the user to select the region within patient 11 from which PNFS is to be shifted away. In the illustrated example, first drop-down list 332 indicates that the user has selected region 1 as the region from which PNFS is to be shifted, which may be, e.g., region 284 in FIG. 16A. A second drop-down list 334 presents a list of regions from which the user may select a region to which PNFS is shifted. In the illustrated example, second drop-down list 334 indicates that the user has selected region 2 (e.g., region 286 in FIG. 16A) as the region to which PNFS is to be shifted.

A third drop-down list 336 allows the user to select a time period over which the shift will occur. For example, the time shift may be relatively rapid, e.g., occurring over a time period of less than about 5 seconds. In other examples the time shift may be relatively gradual, e.g., occurring over a time period of greater than about 2 minutes. In other examples, the time shift may be intermediate, e.g., occurring over a time period of greater than about 5 seconds, but less than about 2 minutes. In the illustrated example, the third drop-down list 336 indicates that the user has selected a time period of five minutes over which the shift of PNFS from Region 1 to Region 2 is to occur. Once the user has entered the desired regions and desired time period for implementing the shift, the user may select apply button 337 to apply the therapy input. If the user decides to not shift PNFS at this time, the user may select cancel button 338, and processor 70 will not apply the indicated PNFS shift.

Upon receiving the therapy input indicating a shift from one region to another, e.g., after the user selects the apply button 337, processor 70 of clinician programmer 22 may transmit the therapy input from the user to IMD 14 via the respective telemetry modules 80, 36. In some examples, processor 32 of IMD 14 may shift therapy delivery between Region 1 and Region 2 by deactivating therapy delivery according to a first therapy program to Region 1, and simultaneously activating therapy delivery according to a second therapy program that is different than the first therapy program to Region 2. The first and second therapy programs may define different electrode configurations because different electrodes may be implanted within Regions 1 and 2. That is, a different subset of electrodes of an electrode array may be implanted within Region 1 compared to Region 2, although some of the electrodes of the subsets associated with Regions 1 and 2 may overlap.

Processor 70 of clinician programmer 22 or processor 32 of IMD 14 may select the first and second therapy programs. For example, the first therapy program may be associated with Region 1 and the second therapy program may be associated with Region 2 in memory 41 of IMD 14 or memory 74 of clinician programmer 22. At least one of the processors 32, 70 may apply a look-up function to the stored information to determine which therapy program is associated with the therapy regions selected by patient 11.

The activation and deactivation of PNFS to Regions 1 and 2, respectively, may be immediate or gradual. For example, processor 32 of IMD 14 may provide instructions that cause stimulation generator 38 (FIG. 2) to time-interleave stimulation energy between the electrode combinations associated with Regions 1 and 2, as described in commonly-assigned U.S. patent application Ser. No. 11/401,100 by Steven Goetz et al., entitled, "SHIFTING BETWEEN ELECTRODE COMBINATIONS IN ELECTRICAL STIMULATION DEVICE," and filed on Apr. 10, 2006, the entire content of which is incorporated herein by reference. In the time-interleave shifting example, the amplitudes of the electrode combinations of the first and second therapy program are ramped downward and upward, respectively, in incremental steps until the amplitude of the electrode combination of the second therapy program associated with Region 2 reaches a target amplitude. The incremental steps may be different between ramping downward or ramping upward. The incremental steps in amplitude can be of a fixed size or may vary, e.g., according to an exponential, logarithmic or other algorithmic change. When the second electrode combination reaches its target amplitude, or possibly before, the delivery of PNFS via the first electrode combination associated with Region 2 may be stopped.

In some examples, if stimulation generator 38 of IMD 14 shifts the delivery of PNFS energy between two programs, regardless of whether the PNFS is shifted between two or more therapy regions within patient 11, stimulation generator 38 (FIG. 2) of IMD 14 may time-interleave the therapy delivery according to the therapy programs using the techniques described above with respect to U.S. patent application Ser. No. 11/401,100 to Goetz et al.

In other examples of user interface screen 330, screen 330 may not include first, second, and third drop-down lists 332, 334, 336, and may instead include other user interface elements that allow the user to indicate the regions from which and to which the PNFS is to be shifted and the time period over which the shift is to occur. For example, screen 330 may include icons, text entry fields, or the like, which allow the user to input the PNFS shift information. Further, in other examples, user interface screen 330 may not present the patient with an option of a time period for implementing the shift of PNFS delivery from one selected region to another. Instead, processor 70 may select a clinician-specified time period for shifting PNFS delivery from one therapy region in which patient 11 feels pain to another therapy region in which patient 11 feels pain.

Figure 16G:
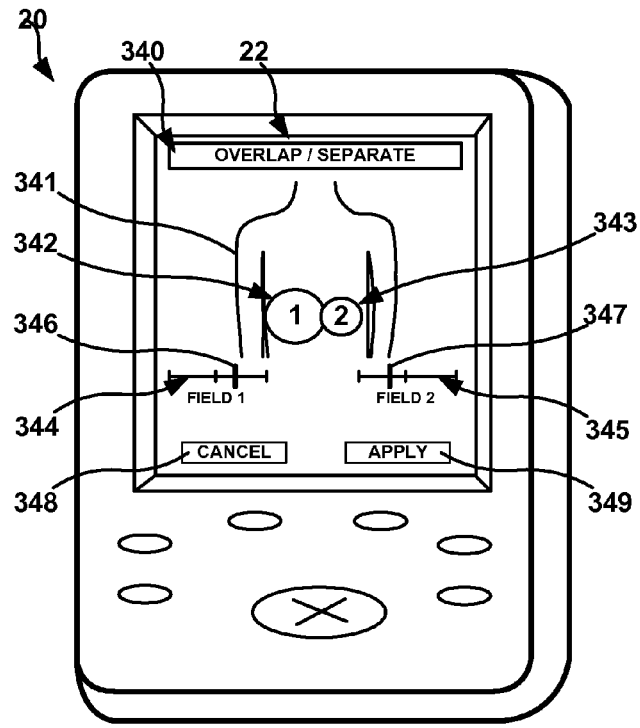

FIG. 16G illustrates an example user interface screen 340 that a user may interact with to provide therapy input indicating an extent to which a first stimulation field produced by delivering PNFS to a first region overlaps a second stimulation field produced by delivering PNFS to a second region. In some examples, user interface screen 340 may be presented to a user by processor 70 of clinician programmer 20 via display 22. In the illustrated example, screen 140 includes a representation of a body 341 of patient 11, which may be similar to the representation of body 282 shown in FIG. 16A. Screen 340 also includes a representation of a first stimulation field 342 produced by PNFS delivered to a first region in which patient 11 experiences pain, and a representation of a second stimulation field 343 produced by PNFS delivered to a second region in which patient 11 experiences pain.

In the example shown in FIG. 16G, user interface screen 340 further includes a first slider 344 and a second slider 345, which allow the user to adjust the size of first stimulation field 342 and second stimulation field 343, respectively, by adjusting the positions of bar 346 and bar 347 on sliders 344, 345, respectively. A first end and second end of each of the sliders 344, 345 may correspond to the size of stimulation fields 342, 343. For example, in FIG. 16G, bar 346 is positioned along the right half of slider 344, which corresponds to a relatively large first stimulation field 342 and bar 347 is positioned along the left half of slider 345, which indicates that second stimulation field 343 is smaller relative to first stimulation field 342. By adjusting the positions of bar 346 and bar 347, the sizes of first stimulation field 342 and second stimulation field 343 may be adjusted, and the extend to which the fields 342, 343 overlap or are separated may be adjusted.

Upon receiving therapy input adjusting the size of first stimulation field 342 and second stimulation field 343 via user interface screen 340, processor 70 may adjust the therapy programs that define the first and second stimulation fields 342, 343, respectively. The therapy programs may include electrode configurations for generating the first stimulation field 342 and second stimulation field 343. In some examples, after the user provides input indicating a smaller stimulation field 342 is desirable, processor 70 may adjust the electrode configuration in Region 1 to decrease a relative distance between at least one anode electrode and at least one cathode electrode of the electrode combination of the respective therapy program for Region 1, which may result in a smaller stimulation field 342. Alternatively, additional electrodes may be selected. In addition to or instead of modifying the electrode configuration of the therapy program for Region 1, processor 70 may increase the intensity of stimulation, e.g., by increasing at least one of the voltage or current amplitude value of the stimulation signal defined by the therapy program, the frequency of stimulation signals defined by the therapy program, signal duration (e.g., pulse width in the case of stimulation pulses) defined by the therapy program.

Conversely, upon receiving input from the user indicating a larger first stimulation field 342 is desirable, processor 70 may adjust the electrode configuration in Region 1 to increase a relative distance between at least one anode electrode and at least one cathode electrode, which may result in a larger stimulation field 342. Alternatively, additional electrodes may be selected. In addition to or instead of modifying the electrode configuration of the therapy program for Region 1, processor 70 may increase the intensity of stimulation to increase the size of stimulation field 342, e.g., by increase at least one of the voltage or current amplitude value of the stimulation signal defined by the therapy program, the frequency of stimulation signals defined by the therapy program, signal duration (e.g., pulse width in the case of stimulation pulses) defined by the therapy program. In the described examples, the modified therapy program may be stored within memory 41 of IMD 14 and/or within another device, such as clinician programmer 20. Processor 70 may adjust an electrode configuration for each selected region similarly for similar inputs.

In the illustrated example, first stimulation field 342 and second stimulation field 343 overlap. If the user provides a therapy input indicating the size of either stimulation field 342 or 343 should be increased, e.g., by moving either of bar 346 or bar 347 to the right side of the respective sliders 344, 345, the extent of overlap between stimulation fields 342, 343 will increase. Conversely, if the user decreases the size of either stimulation field 342, 343, e.g., by moving either of bar 346 or bar 347 to the left side of the respective sliders 344, 345, the extent of overlap between stimulation fields 342, 343 may decrease. In some cases, the user may modify the size of stimulation fields 342, 343 until the fields 342, 343 no longer overlap. The relative sizes of fields 342, 343 displayed in FIG. 16G may be represented qualitatively (e.g., graphically) or quantitatively (e.g., via a calibration procedure).

In other embodiments, screen 340 may include other user interface elements that allow the user to adjust the sizes of first stimulation field 342 and second stimulation field 343 within the screen 340. For example, processor 70 may allow the user to select a stimulation field (e.g., stimulation field 342) with a cursor manipulated by a mouse or with a stylus and drag the cursor or stylus to move the outer boundaries of the stimulation field, thereby adjusting the size of the stimulation field. In other examples, screen 340 may include a drop-down list, icons, checkboxes, radio buttons, other buttons, or the like, which allow the user to adjust the size of a selected stimulation field and the extent to which at least two stimulation fields overlap. Although FIG. 16G illustrates two stimulation fields 342, 343, in other examples, user interface screen 340 may provide interface elements for selecting one region or more than two regions and adjusting the size of the stimulation fields produced by PNFS in each region and the extent to which the stimulation fields overlap.

In another aspect, the disclosure is directed to techniques with which a user, such as patient 11, may control PNFS delivery by IMD 14. In some examples, patient 11 may select the type of therapeutic effect of the PNFS desired at a given point in time. Enabling patient 11 to select the therapeutic effect of the PNFS delivery by IMD 14 provides patient 11 some control over the PNFS therapy.

Figure 17:
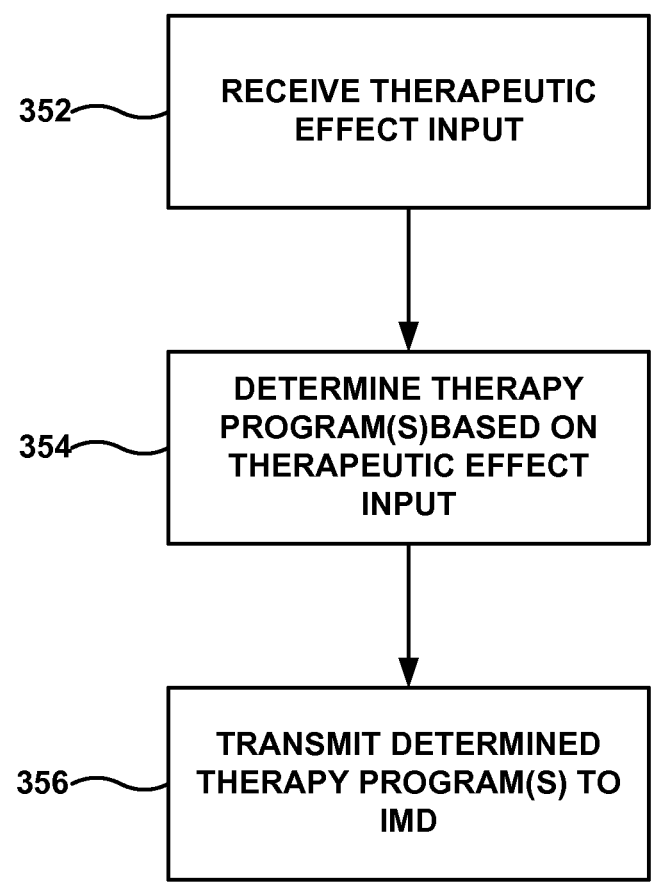
FIG. 17 is a flow diagram illustrating an example technique for using a programmer to program a medical device to deliver PNFS based on a desired therapeutic effect input.

FIG. 17 is a flow diagram of an example technique for receiving input from a user, such as patient 11, selecting a therapeutic effect and controlling IMD 14 to delivery PNFS via the selected therapeutic effect. Different stimulation parameter values may have a different physiological effect on patient 11 because the different parameter values may recruit different neurons within the neural tissue of patient 11, and, therefore, may be perceived differently by patient 11. For example, a relatively high PNFS frequency (e.g., greater than or equal to about 30 Hertz (Hz), but may be determined by a clinician on a patient-specific basis) may engage nerve pathways, thereby causing patient 11 to experience paresthesia in the dermatome where the electrodes are placed, whereas a relatively low PNFS frequency (e.g., less than about 30 Hz, but may be determined by a clinician on a patient-specific basis) may affect the sensory system or muscle tissue. For example, PNFS may activate muscle tissue or reduce pain through stimulating the production of endogenous endorphins at the lower frequency levels (e.g., 30 Hz or less, but may be determined by a clinician on a patient-specific basis). Accordingly, processor 50 of patient programmer 18 may select a therapy program that defines a stimulation frequency that is associated with the desired therapeutic effect inputted by the user.

As shown in FIG. 17, processor 50 of patient programmer 18 may receive a desired therapeutic effect input (352) from patient 11 via a user interface 52 of patient programmer 18. While patient programmer 18 and its functional components are primarily referred to in the description of FIGS. 17-19B, in other examples, another computing device, such as clinician programmer 20, may receive input from a user selecting a desired therapeutic effect. Further, in each of the techniques described with respect to FIGS. 17-19B, input selecting a therapeutic effect may be received from a user other than patient 11, such as a clinician.

Patient 11 may not possess the skill or knowledge to adjust the therapy parameter values to achieve a particular therapeutic effect, or even recognize the therapeutic effect of predetermined programs stored in a memory 54, 41 of patient programmer 18 or IMD 14. Accordingly, in some examples, processor 50 of patient programmer 18 may present a user interface that provides patient 11 with a list of predetermined stimulation effects that are each associated with one or more therapy programs. In some examples, patient 11 may indicate via user interface 52 of patient programmer 18 which of the listed therapeutic effects are desired, and processor 50 of patient programmer 18 or processor 32 of IMD 14 may determine a therapy program based on the therapeutic effect input (354). In some examples, patient 11 may indicate more than one desired therapeutic effect.

As examples of therapeutic effects, to produce a muscle effect, such as muscle relaxation, processor 50 may determine a therapy program comprising a very low stimulation pulse frequency. For example, the stimulation pulse frequency may be less than about 10 Hz. However, the stimulation pulse frequency or range of frequencies which produce a muscle effect may vary from patient to patient, and may be, but need not be, determined by a clinician on a patient-specific basis via in-clinic testing or another calibration procedure. As another example, to reduce pain through stimulating the production of endogenous endorphins, processor 50 may determine a therapy program comprising a stimulation pulse frequency in a range of about 10 Hz to about 30 Hz. Once again, the stimulation pulse frequency or range of frequencies which stimulate the production of endogenous endorphins may vary from patient to patient, and may be, but need not be, determined by a clinician on a per-patient basis via in-clinic testing or another calibration procedure.

As yet another example, to produce paresthesia, processor 50 may determine a therapy program comprising a stimulation pulse frequency greater than about 30 Hz. Again, the stimulation pulse frequency or range of frequencies which produce paresthesia may vary from patient to patient, and may be, but need not be, determined by a clinician on a per-patient basis via in-clinic testing or another calibration procedure. In some examples, processor 50 may select from therapy programs 58 stored in memory 54 of patient programmer 18 (FIG. 3), which may be selected by a clinician. In other examples, processor 50 may generate a therapy program based on the therapeutic effect input.

In some examples, patient 11 indicates more than one desired therapeutic effect via inputting information into programmer 18, and processor 50 determines one or more therapy programs that IMD 14 may deliver therapy in accordance with in order to achieve each of the therapeutic effects indicated by patient 11 (354). IMD 14 may deliver the PNFS therapy according to the multiple selected programs simultaneously or on a time-interleaved basis, either in an overlapping or non-overlapping manner. For example, patient 11 may indicate that both paresthesia and muscle relaxation are desired therapeutic effects (352). In response, processor 50 may determine a first therapy program that includes a stimulation frequency of about 10 Hz, which activates muscle tissue within the region of tissue in which patient 11 feels pain, and a second therapy program that defines a stimulation frequency of about 30 Hz, which produce paresthesia.

In addition to determining a stimulation frequency, processor 50 may also determine other therapy parameters of the PNFS program based on the therapeutic effect input. For example, processor 50 may determine a voltage or current amplitude, pulse width, and electrode configuration. In examples in which patient 11 indicates more than one therapeutic effect, the other therapy parameter values of the therapy programs associated with the selected therapeutic effects (e.g., current or voltage amplitude and signal duration) may differ from each other or may be the same.

In some examples, PNFS delivered to produce the desired therapeutic effect(s) may be delivered continuously. In other examples, PNFS may be delivered intermittently or on a time-limited basis. For example, IMD 14 may deliver PNFS for a limited duration of time, and the therapeutic effect may persist after the cessation of the PNFS. In some examples, the processor 50 (or processor 32 or 70) may control the duration PNFS, or a clinician or patient 11 may select the length of PNFS delivery. For example, patient 11 may request a "bolus" or "dose" of stimulation therapy. In some examples, the clinician may set limits on the delivery of stimulation, such as limiting the amount of PNFS in a day or the frequency of PNFS. These limits may prevent accommodation of tissue in the region to the effects of PNFS, or may increase the efficacy of the therapy.

Patient 11 may adapt to PNFS over time. That is, a certain level of electrical stimulation provided to region 12 may be less effective over time. This phenomenon may be referred to as "adaptation" or "accommodation." As a result, any beneficial effects to patient 11 from PNFS may decrease over time. While the electrical stimulation levels (e.g., amplitude of the electrical stimulation signal) may be increased to overcome such adaptation, the increase in stimulation levels may consume more power, and may eventually reach undesirable or harmful levels of stimulation. Delivering therapy to patient 11 according to different therapy programs and limiting the amount of PNFS delivered to patient 11 may help reduce the rate of accommodation to the PNFS.

In some cases, memory 54 of patient programmer 18 (FIG. 3) may store a plurality of therapy programs that are each associated with an expected therapeutic effect. The therapy programs and associated therapeutic effects may be selected based on information specific to patient 11 (e.g., based on testing a plurality of therapy programs on patient 11 and determining the therapeutic effect) or based on information general to two or more patients. In some examples, processor 50 may determine the one or more therapy programs based on the therapeutic effect input from patient 11 or another user by reference a look-up table within memory 54. Processor 50 may identify the desired therapeutic effect inputted by the user within the look-up table (or another data structure) and select one or more therapy programs associated with the desired therapeutic effect within the look-up table.

After determining the one or more therapy programs based on the therapeutic effect input, processor 50 may transmit the one or more therapy programs to IMD 14 via the respective telemetry modules 60, 36 (356). Processor 32 of IMD 14 may receive the one or more therapy programs from patient programmer 18 and control stimulation generator 38 to provide PNFS according to the one or more received therapy programs.

Figure 18:
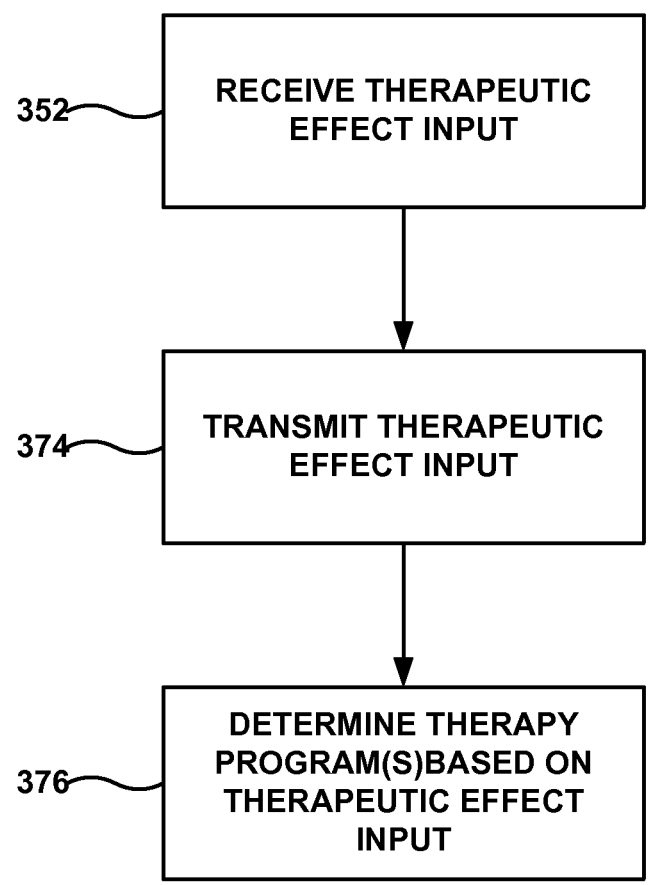
FIG. 18 is a flow diagram illustrating another example technique for using a programmer to program a medical device to deliver PNFS based on a desired therapeutic effect input.

In other examples, as illustrated in FIG. 18, processor 50 may receive the therapeutic effect input from a user (352), and transmit the therapeutic effect input (374) to IMD 14. Processor 32 of IMD 14 may receives the therapeutic effect input and determine a therapy program for providing PNFS to the region in which patient 11 experiences pain and achieve the indicated therapeutic effect (376).

Figure 19A:
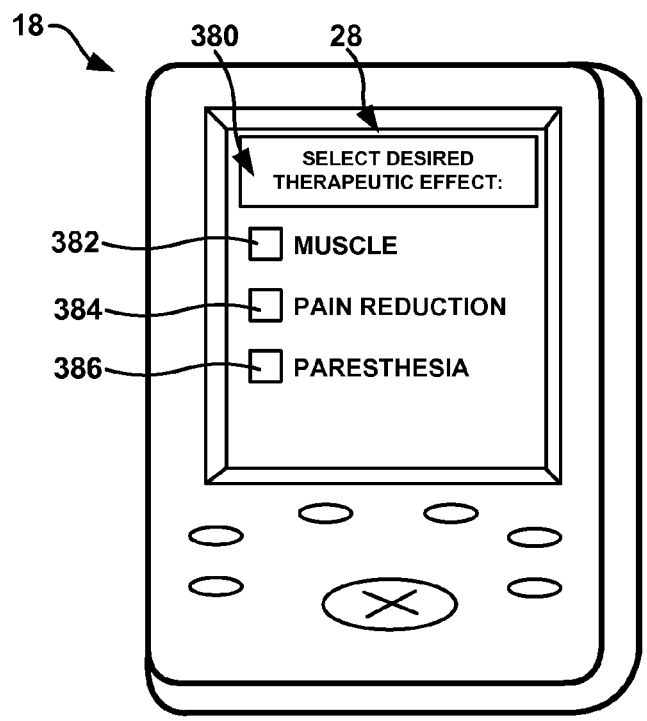
FIGS. 19A and 19B illustrate example user interfaces that may be displayed by a programmer for receiving a desired therapeutic effect input.
Figure 19B:
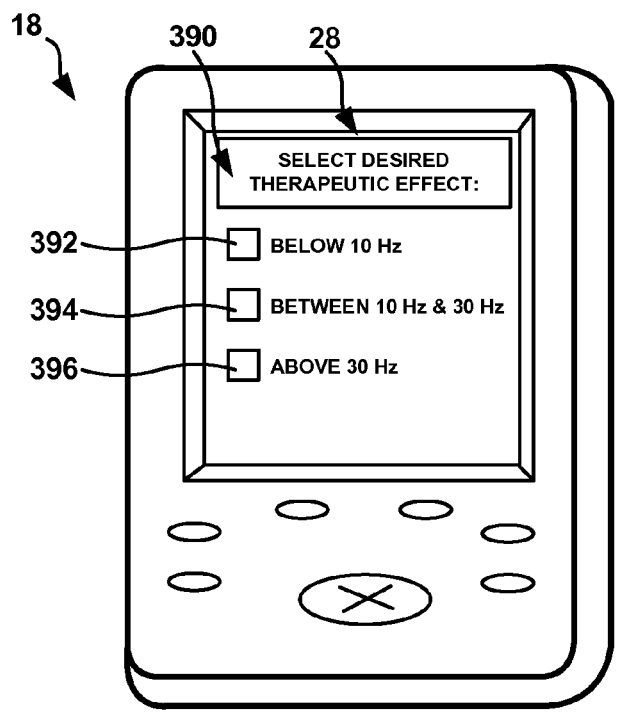

FIGS. 19A and 19B illustrate example user interface screens that a user may interact with to provide input indicating a desired therapeutic effect. The user interface screens shown in FIGS. 19A and 19B may be presented by processor 50 of patient programmer 18 via display 28 or by another processor (e.g., processor 70 of programmer 20) via a display of its respective device. FIG. 19A illustrates an example user interface screen 380 that prompts patient 11 to provide a therapeutic effect input by selecting a therapeutic effect for patient 11 from the PNFs therapy that the user wishes to achieve. In the example shown in FIG. 19A, user interface screen 380 includes a muscle checkbox 382, which the user may select to indicate a therapeutic effect involving muscle stimulation is desirable. Screen 380 also includes a pain reduction checkbox 384, which the user may select to indicate that pain reduction through stimulation of the production of endogenous endorphins is a desirable therapeutic effect. Screen 380 also includes paresthesia checkbox 386, which the user may select to indicate paresthesia is a desired therapeutic effect. In some examples, patient 11 may select more than one checkbox 382, 384, 386, indicating that patient 11 desires IMD 14 to deliver therapy to achieve more than one stimulation effect.

As described above, processor 50 of patient programmer 18 may determine a therapy program based on the desired therapeutic effect input. For example, when patient 11 selects checkbox 382, processor 50 may determine a therapy program defining a stimulation frequency of less than, e.g., about 10 Hz. As another example, when patient 11 selects checkbox 384, processor 50 may determine a therapy program defining a stimulation pulse frequency of, e.g., about 10 Hz to about 30 Hz. As yet another example, when patient 11 selects checkbox 386, processor 50 may determine a therapy program defining a stimulation pulse frequency of greater than, e.g., about 30 Hz. As described above, when patient 11 selects more than one checkbox 382, 384, 386, processor 50 may select a respective therapy program that corresponds to each selected therapeutic effect, and IMD 14 may deliver PNFS therapy including according to the multiple therapy programs (e.g., on an interleaved or alternating basis).

In other examples, screen 380 may include a drop-down list, icons, radio buttons, other buttons, or the like, which allow patient 11 to provide input indicating a desired therapeutic effect. As previously indicated, the frequency ranges for achieving the different therapeutic effects may be specific to patient 11 or may be non-specific to patient 11, e.g., based on known relationships between different frequency ranges and therapeutic effects.

FIG. 19B illustrates another example user interface screen 390 that processor 50 of patient programmer 18 may present via display 28. User interface screen 390 allows patient 11 to directly select the stimulation frequency range with which patient 11 desires IMD 14 to deliver PNFS, thereby indicating a desired therapeutic effect. In the illustrated example, first checkbox 392 indicates a stimulation pulse frequency of below about 10 Hz, which may correspond to a desired therapeutic effect of muscle activation. Second checkbox 394 indicates a stimulation pulse frequency of between about 10 Hz and about 30 Hz, which may correspond to a desired therapeutic effect of pain reduction via production of endogenous endorphins. Third checkbox 396 indicates a stimulation pulse frequency of above (or greater than) about 30 Hz, which may correspond to a desired therapeutic effect of paresthesia.

In other examples, screen 390 may include greater or fewer stimulation frequency ranges for selection by patient 11 or another user, or may allow the user to indicate a particular a stimulation frequency, rather than selecting a stimulation frequency range. In some examples, patient 11 may select more than one checkbox 392, 394, 396 to indicate that more than one therapeutic effect is desirable. In other examples, screen 390 may include a drop-down list, icons, checkboxes, radio buttons, other buttons, or the like, which allow the patient 11 to indicate the stimulation frequency.

In some examples, each of the programming techniques described above may be utilized together. For example, a clinician may select at least one region from a plurality of regions in which patient 11 experiences pain, enter a stimulation field vector input to indicate a stimulation field in that region, and adjust a relative intensity of the PNFS delivered to the at least one region with respect to PNFS delivered to another region. As another example, patient 11 may enter a stimulation field vector input to indicate a stimulation field in a region in which patient 11 experiences pain, and then provide a therapeutic effect input to select the effect which the patient 11 desired in the region. Other combinations of the programming techniques are envisioned, and fall within the scope of the following claims.

Figure 20:
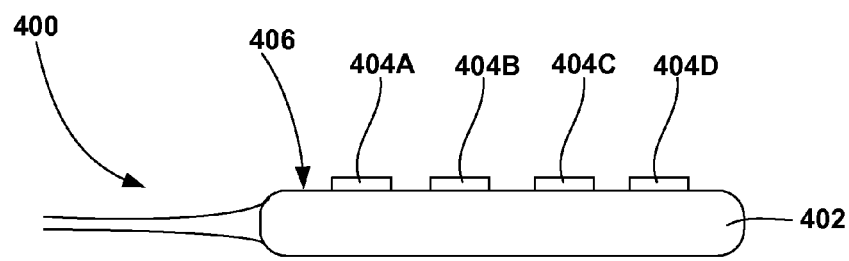
FIG. 20 is a conceptual illustration of an example electrode array including four electrodes coupled to a common lead body.
Figure 21:
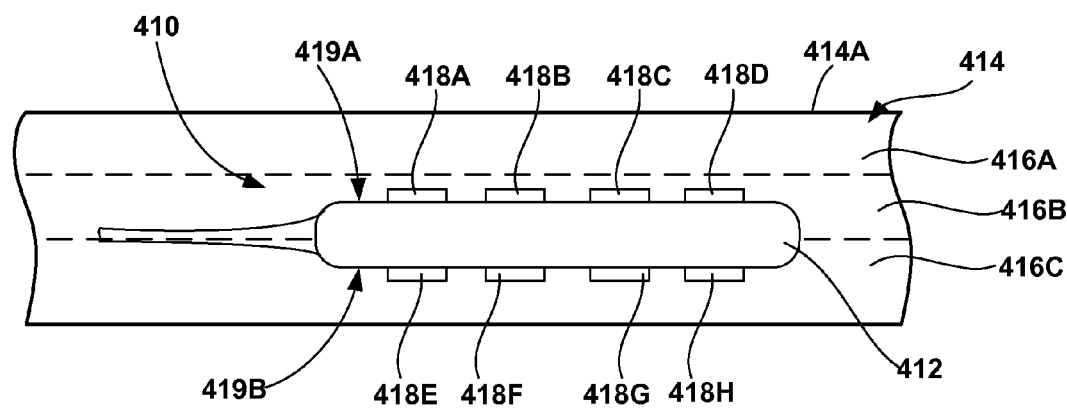
FIG. 21 is a conceptual illustration of an example electrode array including four electrodes coupled to a first surface of a lead body and four electrodes coupled to a second surface of a lead body.
Figure 22:
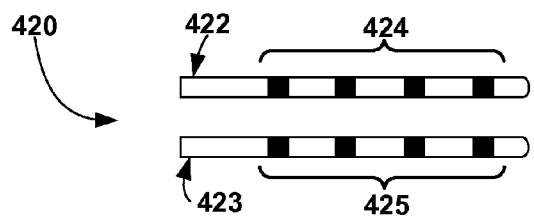
FIG. 22 is a conceptual illustration of an example electrode array including four electrodes coupled to a first lead body and four electrodes coupled to a second lead body.

FIGS. 20-22 are schematic diagrams illustrating example electrode arrays that may be used to provide PNFS therapy. The electrode arrays shown in FIGS. 20-22 may be electrically connected to IMD 14 or another device including a signal generator. FIG. 20 illustrates an example electrode array 400 including four electrodes 404A, 404B, 404C, and 404D (collectively "electrodes 404") coupled to a surface 406 of a common lead body 402. In the illustrated example, lead body 402 comprises a double-sided paddle lead. Electrodes 404 are coupled to a single surface 406 in FIG. 20, but in other examples, such as the paddle-type lead illustrated in FIG. 21, electrodes 404 may be coupled to more than one surface of lead body 402. Electrode array 400 may be implanted in a region in which a patient (e.g., patient 11) experiences pain to provide PNFS therapy. A proximal end (not shown) of lead body 402 may be electrically coupled to an IMD (e.g., IMD 14), which provides stimulation pulses or stimulation waveforms to at least one of the electrodes 404 via conductors (not shown) in the lead body 402.

FIG. 21 is a schematic diagram illustrating an example electrode array 410 including eight electrodes 418A-418H coupled to a common lead body 412. Electrodes 418A-418H are positioned on first and second surfaces 419A and 419B (collectively "surfaces 419") of lead body 412. In FIG. 21, the first and second surfaces 419A, 419B are opposing, substantially parallel, top and bottom surfaces of lead body 412. Lead body 412 has a substantially flat, paddle-like shape, e.g., has a substantially oblong or rectangular cross-sectional shape. In other examples, lead body 412 may have other shapes.

As shown in FIG. 21, electrodes 418A-418D are positioned on top surface 419A of lead body 412 and electrodes 418E-418H are positioned on the bottom surface 419B of lead body 412. Electrodes 418A-418H (collectively "electrodes 418") may extend above surfaces 419, may be recessed relative to the surfaces 419, or may be co-planar with surfaces 419. Electrodes 418 may be electrically insulated from each other.

In the illustrated example of FIG. 21, lead body 412 includes eight electrodes, i.e., electrodes 418, positioned on the top and bottom surfaces 419A, 419B of lead body 412 for purposes of illustration. However, lead body 412 may include a fewer or a greater number of electrodes. A dual sided paddle lead, as shown in FIG. 21, having numerous electrodes may be particularly advantageous because the number of electrode possible combinations increases with the number of electrodes carried by the lead. In other words, providing a large number of electrode combinations increases the likelihood of discovering an electrode combination that achieves a high clinical efficacy with minimal side effects and favorable power consumption characteristics.

Electrodes 418 are arranged in a linear array along substantially the entire length of the top and bottom surfaces 419 of lead body 412. However, the invention is not limited as such. Rather, electrodes 418 may also be arranged in a two-dimensional array or any other regularly or irregularly spaced pattern, and may be distributed in discrete groups or "clusters," or be distributed substantially evenly over substantially the entirety of surfaces 419. In any case, each of electrodes 418 may be electrically coupled to an IMD (not shown), such as IMD 14, via a separate electrical conductor (not shown). The electrical conductors may reside in lead body 412, where they may be electrically insulated and protected from body fluids.

An IMD may select one or more of electrodes 418 for electrode configurations to deliver PNFS to a patient, e.g., using the techniques described above. With respect to FIG. 21, electrodes 418 carried by lead body 412 deliver PNFS to tissue 414 (schematically shown in FIG. 21). In particular, electrodes 418A-418D may deliver PNFS to tissue 416A, which is shallower than lead body 412 relative to epidermis surface 414A, and electrodes 418E-418H may deliver PNFS to tissue 416C, which is located more deep than lead body 412 relative to epidermis surface 414A. For example, lead body 412 may be implanted between deep dermal tissue layer 416B and subcutaneous tissue layer 416C, and may stimulate nerves and/or tissue in both deep dermal tissue layer 416B and subcutaneous tissue layer 416C, as well as tissue within inter-dermal tissue layer 416A.

In other examples, lead body 412 may be implanted within or between any of the intra-dermal, deep dermal, or subcutaneous tissue, or within any tissue or tissue layer of a patient. The thickness of lead body 412, e.g., the relative distance between electrodes 418A-418D and electrodes 418E-418H, may be varied or selected depending on various design parameters, such as the tissues or layers for which stimulation is desired, as well as the anticipated proximity of lead body 412 to such tissues or layers. Further, the depth of different layers of tissue of the patient may vary depending on the anatomy of the patient, e.g., layers of tissue of an obese patient may be thicker than those of a slender patient.

In other examples in which lead body 412 is implanted within a particular tissue layer, such as deep dermal layer 416B, the thickness of lead body 412 may also affect the degree of PNFS delivered to that layer of tissue. For example, if the thickness of lead body 412 is sufficiently large, tissue 416B may not be substantially stimulated. However, the thickness of lead body 412 may be sufficiently small such that electrodes 418 of lead body 412 provide some PNFS to tissue 416B. As a result, in some examples, lead body 412 may be configured to stimulate substantially distinct layers of tissue. In general, multiple leads at differently dermal layers might be used to control depth of PNFS, or a single lead may be implanted at an angle and electrodes of the single lead may be selected in order to control depth of PNFS FIG. 22 is a schematic diagram illustrating another example electrode array 420, which includes four electrodes 424 coupled to a first lead body 422 and four electrodes 425 coupled to a second lead body 423, which is separate from first lead body 422.

The electrode arrays illustrated in FIGS. 20-22 are examples, and other electrode arrays are contemplated. For example, an electrode array may include a bifurcated lead with electrodes coupled to each branch of the lead. As another example, an electrode array may include one or more lead coupled to a lead and a housing of an IMD, or an electrode coupled to the housing of the IMD. Further, an electrode array may include one or more electrodes coupled a housing of an IMD.

The disclosure also contemplates computer-readable media comprising instructions to cause a processor to perform any of the functions and techniques described herein. The computer-readable media may take the form of any volatile, non-volatile, magnetic, optical, or electrical media, such as a RAM, ROM, NVRAM, EEPROM, flash memory, or any other digital media. A programmer, such as patient programmer 18 or clinician programmer 20, may also contain a more portable removable memory type to enable easy data transfer or offline data analysis.

The techniques described in this disclosure, including those attributed to IMD 14, clinician programmer 20, patient programmer 18, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 32 of IMD 14, processor 50 of patient programmer 18, and/or processor 70 of clinician programmer 20, any one or more parts of the techniques described herein may be implemented by a processor of one of IMD 14, patient programmer 18, clinician programmer 20, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
   receiving, by a processor, a stimulation field vector input from a user via a user interface, wherein the stimulation field vector input indicates a direction of peripheral nerve field electrical stimulation within a stimulation field that provides peripheral nerve field electrical stimulation in a region of a body of a patient in which the patient experiences pain, and wherein the stimulation field vector input comprises a vector beginning point and a vector end point;
   receiving, by the processor, a stimulation breadth input from the user that indicates a breadth of the stimulation field;
   receiving, by the processor, a stimulation depth input from the user that indicates a depth of the stimulation field relative to a reference point of the patient; and
   determining, by the processor, an electrode configuration for generating the stimulation field based on the stimulation field vector input, the stimulation breadth input, and the stimulation depth input, wherein determining the electrode configuration comprises:
     selecting, by the processor, a first active electrode from a three-dimensional electrode array implanted in the region of the body of the patient based on the vector beginning point,
     selecting, by the processor, of a second active electrode from the three-dimensional electrode array based on the vector end point, the stimulation breadth input, and the stimulation depth input, and
     selecting, by the processor, polarities of the first and second active electrodes.

2. The method of claim 1, wherein the first active electrode comprises an anode electrode and the second active electrode comprises a cathode electrode, and determining the electrode configuration comprises determining an arrangement of the cathode electrode and the anode electrode within the electrode array.

3. The method of claim 1, wherein the three-dimensional electrode array comprises at least one of electrodes coupled to a common lead body, electrodes coupled to a respective one of at least two lead bodies or electrodes coupled to a housing of an implantable medical device.

4. The method of claim 1, further comprising transmitting at least one of the electrode configuration or the stimulation field vector input to an implantable medical device.

5. The method of claim 1, wherein determining the electrode configuration comprises determining a distance between the first and second active electrodes based on the stimulation breadth input.

6. The method of claim 1, further comprising receiving, by the processor, a stimulation focus input from the user that indicates a size of a stimulation focus of the stimulation field, wherein determining the electrode configuration comprises determining the electrode configuration based on the stimulation field vector input, the stimulation breadth input, the stimulation depth input, and the stimulation focus input.

7. The method of claim 6, wherein determining the electrode configuration comprises determining a number of cathode electrodes based on the stimulation focus input.

8. The method of claim 1, further comprising controlling a medical device to deliver electrical stimulation to the region according to the electrode configuration.

9. The method of claim 1, further comprising presenting the electrode configuration to the user on a display.

10. The method of claim 1, further comprising determining at least one of a stimulation amplitude or a breadth of stimulation based on a magnitude of the stimulation field vector input.

11. A system comprising:
    a user interface; and
    a processor that:
      receives a stimulation field vector input from a user via the user interface, wherein the stimulation field vector input comprises a vector beginning point and a vector end point and indicates a direction of peripheral nerve field electrical stimulation in a stimulation field that provides peripheral nerve field electrical stimulation in a region of a body of a patient in which the patient experiences pain;
      receives a stimulation breadth input from the user via the user interface, the stimulation breadth input indicating a breadth of the stimulation field;
      receives a stimulation depth input from the user via the user interface, the stimulation depth input indicating a depth of the stimulation field relative to a reference point of the patient; and
      determines an electrode configuration for generating the stimulation field based on the stimulation field vector input, the stimulation breadth input, and the stimulation depth input, wherein the processor determines the electrode configuration by at least:
        selecting a first active electrode from a three-dimensional electrode array implanted in the region of the body of the patient based on the vector beginning point,
        selecting a second active electrode from the three-dimensional electrode array based on the vector end point, the stimulation breadth input, and the stimulation depth input, and selecting polarities of the first and second active electrodes.

12. The system of claim 11, wherein the first electrode comprises an anode electrode and the second electrode comprises a cathode electrode, and wherein the processor determines an arrangement of the cathode electrode and the anode electrode within the electrode array.

13. The system of claim 11, further comprising a programmer, wherein the programmer comprises the user interface and the processor.

14. The system of claim 13, wherein the programmer further comprises a telemetry module that transmits at least one of the electrode configuration or the stimulation field vector input to an implantable medical device.

15. The system of claim 11, further comprising a programmer and an implantable medical device, wherein the programmer comprises the user interface and the implantable medical device comprises the processor.

16. The system of claim 11, wherein the three-dimensional electrode array comprises at least one of electrodes coupled to a common lead, electrodes coupled to a respective one of at least two lead bodies or electrodes coupled to a housing of an implantable medical device.

17. The system of claim 11, wherein the user interface comprises a touch screen configured to receive the stimulation field vector input from the user.

18. The system of claim 11, wherein the user interface comprises a display, and wherein the processor presents the electrode configuration to the user via the display.

19. The system of claim 11, wherein the processor receives a stimulation focus input from the user that indicates a size of a stimulation focus of the stimulation field and determines the electrode configuration based on the stimulation field vector input, the stimulation breadth input, the stimulation depth input, and the stimulation focus input.

20. The system of claim 11, wherein the processor determines at least one of a stimulation amplitude or a breadth of stimulation based on a magnitude of the stimulation field vector input.

21. A system comprising:
means for receiving a stimulation field vector input from a user via a user interface, wherein the stimulation field vector input indicates a direction of peripheral nerve field electrical stimulation within a stimulation field that provides peripheral nerve field electrical stimulation in a region of a body of a patient in which the patient experiences pain, and wherein the stimulation field vector input comprises a vector beginning point and a vector end point;

means for receiving a stimulation breadth input from the user that indicates a breadth of the stimulation field;

means for receiving a stimulation depth input from the user that indicates a depth of the stimulation field relative to a reference point of the patient; and means for determining an electrode configuration for generating the stimulation field based on the stimulation field vector input, wherein the means for determining determines the electrode configuration by at least:

selecting a first active electrode from a three-dimensional electrode array implanted in the region of the body of the patient based on the vector beginning point, selecting a second active electrode from the three-dimensional electrode array based on the vector end point, the stimulation breadth input, and the stimulation depth input, and selecting polarities of the first and second active electrodes.

22. The system of claim 21, wherein the first active electrode comprises an anode electrode and the second active electrode comprises a cathode electrode, and wherein the means for determining determines an arrangement of the cathode electrode and the anode electrode within the three-dimensional electrode array.

23. A non-transitory computer-readable medium comprising instructions that cause a processor to:
receive a stimulation field vector input from a user, wherein the stimulation field vector input indicates a direction of peripheral nerve field electrical stimulation within a stimulation field that provides peripheral nerve field electrical stimulation in a region of a body of a patient in which the patient experiences pain, and wherein the stimulation field vector input comprises a vector beginning point and a vector end point;

receive a stimulation breadth input from the user that indicates a breadth of the stimulation field;

receive a stimulation depth input from the user that indicates a depth of the stimulation field relative to a reference point of the patient; and determine an electrode configuration for generating the stimulation field in the region based on the stimulation field vector input, wherein the instructions cause the processor to determine the electrode configuration by at least:

selecting a first active electrode from a three-dimensional electrode array implanted in the region of the body of the patient based on the vector beginning point, selecting a second active electrode from the three-dimensional electrode array based on the vector end point, the stimulation breadth input, and the stimulation depth input, and selecting polarities of the first and second active electrodes.

24. The method of claim 1, wherein the stimulation depth input defines a desired depth relative to an epidermis of a patient.

25. The system of claim 11, wherein the stimulation depth input defines a desired depth relative to an epidermis of a patient.

26. The system of claim 21, wherein the stimulation depth input defines a desired depth relative to an epidermis of a patient.

27. The non-transitory computer-readable medium of claim 23, wherein the stimulation depth input defines a desired depth relative to an epidermis of a patient.

* * * * *